US011083801B2

(12) United States Patent
Laterza et al.

(10) Patent No.: US 11,083,801 B2
(45) Date of Patent: *Aug. 10, 2021

(54) FACTOR VIII MUTATION REPAIR AND TOLERANCE INDUCTION

(71) Applicants: Haplomics, Inc., Manhattan Beach, CA (US); The Regents of the University of California, Oakland, CA (US); THE UNITED STATES GOVERNMENT AS REPRESENTED BY THE DEPARTMENT OF VETERANS AFFAIRS, Washington, DC (US)

(72) Inventors: Vincent Laterza, Atlanta, GA (US); Tommy E. Howard, Brownsville, TX (US)

(73) Assignees: Haplomics, Inc., Manhattan Beach, CA (US); The Regents of the University of California, Oakland, CA (US); The United States Government Represented by the Departrment of Veteran Affairs, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/396,326

(22) Filed: Apr. 26, 2019

(65) Prior Publication Data

US 2019/0351073 A1 Nov. 21, 2019

Related U.S. Application Data

(63) Continuation of application No. 14/649,910, filed as application No. PCT/US2013/073751 on Dec. 6, 2013, now Pat. No. 10,272,163.

(60) Provisional application No. 61/888,424, filed on Oct. 8, 2013, provisional application No. 61/734,678, filed on Dec. 7, 2012.

(51) Int. Cl.
*A61K 48/00* (2006.01)
*C07K 14/755* (2006.01)
*C12N 15/90* (2006.01)
*C12N 9/22* (2006.01)
*A61K 38/00* (2006.01)

(52) U.S. Cl.
CPC ........ *A61K 48/0066* (2013.01); *C07K 14/755* (2013.01); *C12N 9/22* (2013.01); *C12N 15/90* (2013.01); *A61K 38/00* (2013.01); *C12N 2830/42* (2013.01)

(58) Field of Classification Search
CPC ................................................ A61K 48/0066
See application file for complete search history.

(56) References Cited

U.S. PATENT DOCUMENTS

| 4,981,957 | A | 1/1991 | Lebieu et al. |
|---|---|---|---|
| 5,118,800 | A | 6/1992 | Smith et al. |
| 5,149,637 | A | 9/1992 | Scandella et al. |
| 5,154,785 | A | 10/1992 | Tabata et al. |
| 5,319,080 | A | 6/1994 | Leumann |
| 5,359,044 | A | 10/1994 | Cook et al. |
| 5,364,771 | A | 11/1994 | Lollar et al. |
| 5,393,878 | A | 2/1995 | Leumann |
| 5,446,137 | A | 8/1995 | Maag et al. |
| 5,466,786 | A | 11/1995 | Buhr et al. |
| 5,519,134 | A | 5/1996 | Acevedo et al. |
| 5,567,811 | A | 10/1996 | Misiura |
| 5,576,427 | A | 11/1996 | Cook et al. |
| 5,583,209 | A | 12/1996 | Lollar et al. |
| 5,591,722 | A | 1/1997 | Montgomery et al. |
| 5,597,909 | A | 1/1997 | Urdea et al. |
| 5,610,300 | A | 3/1997 | Altmann et al. |
| 5,627,053 | A | 5/1997 | Usman et al. |
| 5,639,873 | A | 6/1997 | Barascut et al. |
| 5,646,265 | A | 7/1997 | McGee |
| 5,658,873 | A | 8/1997 | Bertsch-Frank et al. |
| 5,659,017 | A | 8/1997 | Bhattacharya et al. |
| 5,663,060 | A | 9/1997 | Lollar et al. |
| 5,670,633 | A | 9/1997 | Cook et al. |

(Continued)

FOREIGN PATENT DOCUMENTS

| BR | 112015013311 A2 | 11/2017 |
|---|---|---|
| CA | 2951882 A1 | 12/2015 |

(Continued)

OTHER PUBLICATIONS

Wu et al. (2016, Nature Scientific Reports, pp. 1-11) (Year: 2016).*
Turner et al. (2015, PLoS One, pp. 1-28) (Year: 2015).*
Represse et al. (2007, J. Thrombosis and Haemostasis, vol. 5, pp. 1469-1476) (Year: 2007).*
Batty et al. (2019, Human Molecular Genetics, vol. 28(R1), pp. R95-R101) (Year: 2019).*
Jinkurtar et al. (2011, Challenges in Delivery of Therapeutic Genomics and Proteomics, Elsevier, Chapter 2, pp. 46-54) (Year: 2011).*

(Continued)

*Primary Examiner* — Thaian N. Ton
*Assistant Examiner* — David A Montanari
(74) *Attorney, Agent, or Firm* — Denise L. Mayfield; Dykema Gossett PLLC

(57) ABSTRACT

Methods of treating hemophilia A in a subject with an F8 gene mutation, wherein the F8 gene is repaired and the resultant repaired gene, upon expression, confers improved coagulation functionality to the encoded FVIII protein of the subject compared to the non-repaired F8 gene. The invention also includes methods of inducing immune tolerance to a FVIII replacement product ((r)FVIII) in a subject having a FVIII deficiency, wherein the F8 gene mutation is repaired and the repaired gene, upon expression, provides for the induction of immune tolerance to an administered replacement FVIII protein product. The invention also includes isolated nucleic acids, vectors, recombinant viruses, cells, and pharmaceutical compositions to repair the F8 gene.

14 Claims, 13 Drawing Sheets

Specification includes a Sequence Listing.

(56) References Cited

U.S. PATENT DOCUMENTS

| | | | |
|---|---|---|---|
| 5,700,920 | A | 12/1997 | Altmann et al. |
| 5,744,446 | A | 4/1998 | Lollar et al. |
| 5,859,204 | A | 1/1999 | Lollar |
| 5,888,974 | A | 3/1999 | Lollar et al. |
| 6,180,371 | B1 | 1/2001 | Lollar |
| 6,261,834 | B1 | 7/2001 | Srivastava |
| 6,376,463 | B1 | 4/2002 | Lollar |
| 6,458,563 | B1 | 10/2002 | Lollar |
| 6,517,830 | B1 | 2/2003 | Lollar et al. |
| 6,759,216 | B1 | 7/2004 | Lollar |
| 6,770,744 | B2 | 8/2004 | Lollar |
| 6,852,537 | B2 | 2/2005 | Hebbel et al. |
| 7,037,658 | B2 | 5/2006 | Ginsburg et al. |
| 7,517,522 | B2 | 11/2009 | Ginsburg et al. |
| 7,829,306 | B2 | 11/2010 | Matsuyama et al. |
| 10,272,163 | B2 | 4/2019 | Laterza et al. |
| 2004/0096456 | A1 | 5/2004 | Conti-Fine |
| 2005/0256304 | A1 | 11/2005 | Jones |
| 2006/0228758 | A1 | 10/2006 | Muchhal et al. |
| 2009/0317375 | A1 | 12/2009 | Wagner et al. |
| 2010/0168018 | A1 | 7/2010 | Pikal et al. |
| 2010/0256062 | A1 | 10/2010 | Howard et al. |
| 2011/0177107 | A1 | 7/2011 | Howard |
| 2012/0149115 | A1 | 6/2012 | Kim et al. |
| 2012/0297494 | A1 | 11/2012 | Howard et al. |
| 2015/0023959 | A1 | 1/2015 | Chhabra et al. |
| 2015/0196017 | A1 | 7/2015 | Howard et al. |
| 2015/0197552 | A1 | 7/2015 | Howard et al. |
| 2015/0216944 | A1 | 8/2015 | Howard et al. |
| 2016/0038570 | A1 | 2/2016 | Howard et al. |
| 2016/0038575 | A1 | 2/2016 | Howard et al. |
| 2016/0045575 | A1 | 2/2016 | Howard et al. |
| 2016/0168593 | A1 | 6/2016 | Cost et al. |

FOREIGN PATENT DOCUMENTS

| | | |
|---|---|---|
| EP | 0302968 A1 | 2/1989 |
| EP | 292803 A4 | 7/2016 |
| EP | 3155098 A4 | 1/2018 |
| WO | 1993/003367 A1 | 2/1993 |
| WO | 1997/003195 A1 | 1/1997 |
| WO | 1998/052976 A1 | 11/1998 |
| WO | 2000017375 A2 | 3/2000 |
| WO | 2004037977 A2 | 5/2004 |
| WO | 2006063031 A2 | 6/2006 |
| WO | 2011046568 A1 | 4/2011 |
| WO | 2011088391 A2 | 7/2011 |
| WO | 2012051343 A1 | 4/2012 |
| WO | 2012058480 A1 | 5/2012 |
| WO | 2014089541 A1 | 6/2014 |
| WO | 2014145524 A2 | 9/2014 |
| WO | 2014186585 A2 | 11/2014 |
| WO | 2015054439 A1 | 4/2015 |
| WO | 2015148454 A1 | 10/2015 |
| WO | 2015191899 A9 | 12/2015 |
| WO | 2017112895 A1 | 6/2017 |

OTHER PUBLICATIONS

Gottfried et al. (2013, Extracellular and Intracellular Barriers to Non-Viral Gene Transfer, Intech, Chapter 4, pp. 75-88) (Year: 2013).*
Morfini et al., 2007, Haemophilia, vol. 13, pp. 606-612 (Year: 2007).*
Coppola et al. (2009, J. Thrombosis and Haemostasis, vol. 7, pp. 1809-1815 (Year: 2009).*
CDC Mutation List FVIII—315 pages (Year: 2014).*
PCT/US2005/044229, International Search Report and Written Opinion dated Sep. 30, 2008, 10 pages.
PCT/US2005/044229, International Preliminary Report on Patentability dated Mar. 3, 2009. 6 pages.
PCT/US2009/061075, International Search Report and Written Opinion dated Aug. 5, 2010, 11 pages.
PCT/US2009/061075, International Preliminary Report on Patentability dated Apr. 17, 2012, 7 pages.
PCT/US2011/021394, International Search Report and Written Opinion dated Jul. 15, 2011, 24 pages.
PCT/US2011/021394, International Preliminary Report on Patentability dated Jul. 15, 2012, 17 pages.
PCT/US2013/073751, International Search Report and Written Opinion dated Nov. 20, 2014, 13 pages.
PCT/US2013/073751, International Preliminary Report on Patentability dated Jun. 9, 2015, 9 pages.
PCT/US2014/030314, International Search Report dated Oct. 24, 2014, 5 pages.
PCT/US2014/030314, Written Opinion dated Oct. 24, 2014, 7 pages.
PCT/US2014/030314, International Preliminary Report on Patentability dated Sep. 15, 2015, 8 pages.
PCT/US2014/059787, International Search Report and Written Opinion dated Apr. 10, 2015, 12 pages.
PCT/US2014/059787, International Preliminary Report on Patentability dated Apr. 12, 2016, 8 pages.
PCT/US2015/035399, International Search Report and Written Opinion dated Aug. 27, 2015, 17 pages.
PCT/US2015/035399, International Preliminary Report on Patentability dated Dec. 15, 2016, 13 pages.
PCT/US2016/068402, International Search Report and Written Opinion dated Apr. 13, 2017, 12 pages.
Antonarakis, Stylianos E., et al. "Factor VIII gene inversions in severe hemophilia A: results of an international consortium study." Blood (1995); 86.6: 2206-2212.
Astermark, Jan et al. "Polymorphisms in the TNFA gene and the risk of inhibitor development in patients with hemophilia A." Blood (2006); 108, 12: 3739-3745.
Bangnall, Richard D., et al. "Recurrent inversion breaking intron 1 of the factor VIII gene is a frequent cause of severe hemophilia A." Blood (2002); 99,1: 168-174.
Ballas, Samir K. "Complications of sickle cell anemia in adults: Guidelines for effective management." Cleveland Clinic Journal of Medicine (1999); 48.66(1): 48-58.
Banerji, Julian, et al. "A lymphocyte-specific cellular enhancer is located downstream of the joining region in immunoglobulin heavy chain genes." Cell (1983); 33.3: 729-740.
Barbosa, Maria DFS, et al. "Clinical link between MHC class II haplotype and interferon-beta (IFN-β) immunogenicity." Clininical Immunology (2006): 118.1: 42-50.
Bi, L., et al. "Targeted disruption of the mouse factor VIII gene produces a model of haemophilia A." Nature Genetics (1995); 10.1: 119-121.
Bongers, T.N., et al. "Lower levels of ADAMTS13 are associated with cardiovascular disease in young patients." Atherosclerosis (2009); 207.1: 250-254.
DeGroot, Anne S., et al. "Prediction of immunogenicity: in silico paradigms, ex vivo and in vivo correlates." Current Opinion in Pharmacology (2008), 8.5: 620-626.
DeGroot, Anne S., et al. "Reducing risk, improving outcomes: bioengineering less immunogenic protein therapeutics." Clinical Immunology (2009): 131.2: 189-201.
DeGroot and Moise, "Prediction of immunogenicity for therapeutic proteins: State of the art." Current Opinion in Drug Discovery & Development (2007); 10(3): 332-340.
Elenitoba-Johnson, Kojo SJ, et al. "Solution-based scanning for single-base alterations using a double-stranded DNA binding dye and flourescence-melting profiles." The American Journal of Pathology (2001); 159.3, 845-853.
Elmahmoudi, Hejer, et al. "Factor VIII haplotypes frequencies in Tunisian hemophilicas A." Diagnostic Pathology (2011), 6.1: 54, pp. 1-4.
EP Application No. 13860153.9, Extended European Search Report dated Jun. 13, 2016, 10 pages.
EP Application No. 14765535.1, Extended European Search Report dated Oct. 27, 2016, 11 pages.
EP Application No. 14765535.1, Partial European Search Report dated Jul. 7, 2016, 5 pages.

(56) References Cited

OTHER PUBLICATIONS

Frazer, Kelly A., et al. "A second generation human haplotype map of over 3.1 million SNPs." Nature (2007); 449.7164: 851-861.
Fulcher, Carol A., et al. "Localization of human factor FVIII inhibtor epitopes to two polypeptide fragments." Proceedings of the National Academy of Sciences (1985); 82.22: 7728-7732.
GenBank Assession No. U00684.1 dated Nov. 30, 1993 [downloaded May 3, 2017], 2 pages.
Ghosh, Kanjaksha, et al. "Immune response to FVIII in hemophilia A: an overview of risk factors." Clinical Reviews in Allegry & Immunology (2009): 37.2: 58-66.
Goudemand, Jenny. "Parmaco-economic aspects of inhibitor treatment." European Journal of Haematology (1998), 61.S63, 24-27.
Graw, Jochen, et al. "Haemophilia A: from mutation analysis to new therapies." Nature Reviews Genetics (2005); 6.6: 488-501.
Gundry et al., Amplicon Melting Analysis with Labeled Primers: A Closed-Tube Method for Differentiating Homozygotes and Heterozygotes, Clin. Chem., 49(3):396-406 (2003).
Hay, C.R.M., et al. "The Diagnosis and Management of Factor VIII and IX Inhibitors [colon] A Guideline From the UK Heaemophilia Centre Doctors {APOS] Organization (UKHCDO)." British Journal of Haematology (2000); 111.1: 78-90.
Higuchi, Miyoko, et al. "Molecular characterization of mild-to-moderate hemophilia A: detection of the mutation in 25 to 29 patients by denaturing gradient gel electrophoresis." Proceedings of the National Academy of Sciences (1991); 88.16: 7405-7409.
Higuchi, Miyoko, et al. "Molecular characterization of severe hemophilia A suggests that about half the mutations are not within the coding regions and splice junctions of the factor VIII gene." Proceedings of the National Academy of Sciences (1991); 88.16: 7405-7409.
Hillery, Cheryl A. et al. "Increased adhesion of erythrocytes to components of the extracellular matrix: isolation and characterization of a red blood cell lipid that binds thrombospondin and laminin." Blood (1996); 87.11: 4879-4886.
Hillery, Cheryl A., et al. "The carboxy-terminal cell-binding domain of thrombospondin is essential for sickle red blood cell adhesion." Blood (1999); 94.1: 302-309.
Howard, Tom et al. "African-Americans Express Multiple Haplotypic Forms of the Wildtype Factor VIII (FVIII) Protein: A Possible Role for Pharmacogenetics in FVIII Inhibitor Development?." Blood (2004); 104.11: 384-384 (Abstract).
Howard, Tom E., et al. "Allelically Mismatched Replacement Therapy Due to Common African-Restricted Haplotypes of the Factor (F) VIII Protein May Underlie the Increased Incidence of FVIII Inhibitors Observed in Hemophilia-A Patients of African-Descent." Blood (2006); 108.11: 765-765 (Abstract).
Howard, Tom E., et al. "The Pharmacogenetics and Inhibitor Risk (PIR) Study: establishing the spectrum of factor (F) VIII gene (F8) mutations in African-American hemophilia A patients." Blood (2005); 106.11: 3207-3207 (Abstract).
Jacquemin, Marc: et al. "CD4+ T-cell clones specific for wild-type factor VIII: a molecular mechaism responsible for a higher incidence of inhibitor formation in mild/moderate hemophilia A." Blood (2003); 101.4: 1351-1358.
Kasschau, M.R., et al. "Adhesion of sickle neutrophils and erythrocytes to fibronectin." Blood (1996); 87.2: 771-780.
Kaul, D.K., et al. "Sickle erythrocyte-endothelial interacations in microcirculation: the role of von Willebrand factor implications for vasoocclusion." Blood (1993): 81.9: 2429-2438.
Kemball-Cook, Geoffrey, Edward GD Tuddenham, and Adam I. Wacey. "The factor VIII factor structure and mutation resourse site: HAMSTeRS version 4." Nucleic Acids Research (1998); 26.1: 216-219.
Koren et al., "Clinic validation of the "in silica" prediction of immunogenicity of a human recombinant therapeutic protein." Clinical Immunology (2007): 124(1): 26-32.
Kreuz, Wolfhart, et al. "Epidemiology of inhibitors and current treatment strategies." Haematologica (2003); 88(6): EREP04-EREP04 (Abstract).

Lay, Marla J., et al. "Real-time fluorescence genotyping of factor V Leiden during rapid-cycle PCR." Clinical Chemistry (1997); 43.12: 2262-2267.
Lazarski, Christopher A., et al. "The kinetic stability of MHC class II: peptide complexes is a key parameter that dictates immunodominance." Immunity (2005); 23:1: 29-40.
Lee, Sheritha P., et al. "Sickle Cell Adhesion to Laminin: Potential Role for the α5 Chain." Blood (1998); 92.8: 2951-2958.
Liew, Michael, et al. "Genotyping of single-nucleotide polymorphisms by high-resolution melting of small amplicons." Clinical Chemistry (2004); 50.7: 1156-1164.
Lin, Yi, et al. "Use of blood outgrowth endothelial cells for gene therapy for hemophilia A." Blood (2002); 99.2: 457-462.
Lipsky, Robert H., et al. "DNA melting anaylsis for detection of single nucelotide polymorphisms." Clinical Chemistry (2001); 47.4: 635-644.
Lollar, Pete, et al. "Inhibition of human factor VIIIa by anti-A2 subunit antibodies." Journal of Clinical Investigation (1994); 93.6: 2497-2504.
Lotta, Lucas A., et al. "ADAMTS13 mutations and polymorphisms in congenital thrombotic thrombocytopenic purpura." Human Mutation (2010); 31.1: 11-19.
Marfaing-Koka, A., et al. "Decreased protein S activity in sickle cell disease." Nouv. Rev. Fr. Hamatal, (1993); 35.4; 425-430.
Meyer, Diogo, et al. "Signatures of demographic history and natural selection in the human major histocompatibility complex loci." Genetics (2006); 173.4: 2121-2142.
Meyer, Sara C., et al. "The ADAMTS13 Gene as the immunological Culprit in Acute Acquired TTP-First Evidence of Genetic Out-Breeding Depression in Humans." Blood (2007); 110.11: 277-277.
Nielsen, Peter E., et al. "Sequence-selective recognition of DNA by strand displacement with a thymine-substituted polyamide." Science (1991); 254.5037: 1497-1500.
Oldenburg and Pavlova, "Genetic risk factors for inhibitors to factors VIII and IX." Haemophilia (2006); 12.s6: 15-22.
Powell, Jerry S., et al. "Phase 1 trial of FVIII gene transfer for severe hemophilia A using a retroviral construct administered by peripheral intravenous infusion." Blood (2003); 102.6: 2038-2045.
Ragot, T., et al. "Replication-defective recombinant adenovirus expressing the Epstein-Barr virus (EBV) envelope glycoprotein gp340/220 induces protective immunity against EBV-induced lymphomas in the cottontop tamarin." Journal of General Virology (1993); 74.3: 501-507.
Rocino, A., et al. "Immune tolerance induction in haemophilia A patients with high-responding inhibitors to factor VIII: experience at a single institution." Haemophilia (2001); 7.1: 33-38.
Rocino and De Biasi. "Successful immune tolerance treatment with monoclonal or recombinant factor VIII concentrates in high responding inhibitor patients." Vox Sanguinis (1999); 77.Suppl. 1:65-69.
Scandella, Dorothea, et al. "Epitope mapping human factor VIII inhibitor anitbodies by deletion analysis of factor VIII fragments expressed in *Escherichia coli*." Proceedings of the National Academy of Sciences (1985); 85.16: 6152-6156 (and correction).
Scandella, Dorothea, et al. "A recombinant factor VII A2 domain polypeptide quantitatively neutralizes human inhibitor antibodies that bind to A2." Blood (1993); 82.6: 1767-1775.
Scandella, D., et al. "A soluble recombinant factor VIII fragment containing the A2 domain binds to some human anti-factor VIII antibodies that are not detected by immunoblotting." Thrombosis and Haemostatsis (1992); 67.6: 665-671.
Steere, Allen C., et al. "Antibiotic-refractory Lyme arthritis is associated with HLA-DR molecules that bind a Borrelia burgdorferi peptide." Journal of Experimental Medicine (2006); 203.4; 961-971.
Sugihara, Keiko, et al. "Thrombospondin mediates adherence of CD36+ sickle reticulocytes to endothelial cells." Blood (1992); 80.10: 2634-2642.
Sun, Ning, et al. "Recent advances in targeted genome engineering in mammalian systems." Biotechnology Journal (2012); 7.9: 1074-1087.

(56) References Cited

OTHER PUBLICATIONS

Toole, John J., et al. "A large region (approximately equal to 95 kDa) of human factor VIII is dispensable for in vitro procoagulant activity." Proceedings of the National Academy of Sciences (1986); 83.16: 5939-5942.
Tuddenham, Edward GD, et al. "Haemophilia A: database of nucleotide substitutions, deletions, insertions and rearrangements of the factor VIII gene." Nucleic Acids Research (1994); 22.22: 4851-4868.
UniProt Submission FA8_HUMAN titled. Coagulation factor VIII. Mar. 6, 2013; p. 1, 22-23, 39, 40 pages.
Van De Water, Neil S. et al. "Amplification of a 29.7 kg region of the factor VIII grnr using the expand PCR system." Biochemica (1996); 2: 11-12.
Venter, J. Craig, et al. "The sequences of the human genome." Science (2001); 291.5507: 1304-1351.
Viel, Kevin R., et al. "A sequence variation scan of the coagulation factor VIII (FVIII) structural gene and associations with plasma FVIII activity levels." Blood (2007); 109.9: 3713-3724.
Viel, Kevin R., et al. "Inhibitors of factor VIII in black patients with hemophilia." New England Journal of Medicine (2009); 360.16: 1618-1627.
Walsh, "Biopharmaceutical benchmarks", Nat. Biotechnol. (2010); 28(9): 917-924.
Wang, Peng, et al. "A systematic assessment of MHC class II peptide binding predictions and evaluation of a consesus approach." PLoS Comput Biol (2008); 4.4: e1000048.
Ware, J. et al. "Epitope mapping a human factor VIII inhibitor antibodies by site-directed mutagenesis of a factor VIII polypeptide." Blood Coagulation & Fibrinolysis (1992), 3.6: 703-716.
Wautier, J. L., et al. "Fibrinogen, a modulator of erythrocyte adhesion to vascular endothelium." J Lab Clin Med (1983); 101.6: 911-920.
Wick, T. M., et al. "Unusually large von Willebrand factor multimers increase adhesion of sickle erythrocytes to human endothelial cells under controlled flow." Journal of Clinical Investigation (1987); 80.3: 905-910.
Wittwer, Carl T., et al. "High-resolution genotyping by amplicon melting analysis using LCGreen." Clinical Chemistry (2003); 49.6: 853-860.
Zou, Jizhong, et al. "Oxidase-deficient neutrophils from X-linked chronic granulomatous disease iPS cells: functional correction by zinc finger nuclease-mediated safe harbor targeting." Blood (2011); 117.21: 5561-5572.
Edwards, et al. "Characterization of Coding Synonymous and Non-Synonymous Variants in ADAMTS13 Using Ex Vivo and In Silico Approaches." PLos One (2012); 7: 1-15.
EP Application No. 15807028.4, Extended European Search Report dated Nov. 30, 2017, 8 pages.
Matsui et al., "Ex Vivo Gene Therapy for Hemophilia A that Enhances Safe Delivery and Sustained In Vivo Factor VIII Expression from Lentivirally Engineered Endothelial Progenitors." Stem Cells (2007), 25(10): 2660-2669.
Park et al., "Targeted inversion and reversion of the blood coagulation factor 8 gene in human iPS cells using TALENs." PNAS (2014); 111 (25): 9253-9258.
Solheim, et al., "Viral safety of solvent/detergent-treated plasma." Transfusion (2000); 40(1): 84-90.
Tsai, Han-Mou, "Pathophysiology of thrombotic thrombocytopenic purpura." International Journal of Hematology (2010); 91(1): 1-19.
Walsh, "Gene therapy Progress and Prospects: Gene therapy for the hemophilias." Gene Therapy (2003); 10:99-1003.
Jinkutar et al, (2011, Challenges in Delivery of Therapeutic and Proteomics, Elsevier, Chapter 2, pp. 46-54).
Wu et al. (2016, Nature Scientific Reports, pp. 1-8).
Turner et al. (2015, PLoS One, pp. 1-28).
Gottfried et al. (2013, Extracellular and Intracellular Barriers to Non-Viral Gene Transfer, Intech, Chapter 4, pp. 75-88).
CDC Mutation List 315 pages.
Represse et al. (2007, J. Thrombosis and Haemostasis, vol. 5, pp. 1469-1476).

\* cited by examiner

SEQUENCE LISTING

```
<160> NUMBER OF SEQ ID NOS: 19

<210> SEQ ID NO 1
<211> LENGTH: 50
<212> TYPE: DNA
<213> ORGANISM: Homo sapiens

<400> SEQUENCE: 1
tactatggga tgagttgcag atggcaagta agacactggg gagattaaat          50

<210> SEQ ID NO 2
<211> LENGTH: 49
<212> TYPE: DNA
<213> ORGANISM: Homo sapiens

<400> SEQUENCE: 2
tggaacctta atggtatgta attagtcatt taaagggaat gcctgaata           49

<210> SEQ ID NO 3
<211> LENGTH: 44
<212> TYPE: DNA
<213> ORGANISM: Homo sapiens

<400> SEQUENCE: 3
ttagtattat agtttctcag attatcacca gtgatactat ggga               44

<210> SEQ ID NO 4
<211> LENGTH: 544
<212> TYPE: PRT
<213> ORGANISM: Artificial Sequence
<220> FEATURE:
<223> OTHER INFORMATION: synthetic construct

<400> SEQUENCE: 4

Leu Thr Pro Asp Gln Val Val Ala Ile Ala Ser Asn His Gly Gly Lys
1               5                   10                  15

Gln Ala Leu Glu Thr Val Gln Arg Leu Leu Pro Val Leu Cys Gln Asp
                20                  25                  30

His Gly Leu Thr Pro Asp Gln Val Val Ala Ile Ala Ser Asn His Gly
            35                  40                  45

Gly Lys Gln Ala Leu Glu Thr Val Gln Arg Leu Leu Pro Val Leu Cys
        50                  55                  60

Gln Asp His Gly Leu Thr Pro Asp Gln Val Val Ala Ile Ala Ser Asn
65                  70                  75                  80

Ile Gly Gly Lys Gln Ala Leu Glu Thr Val Gln Arg Leu Leu Pro Val
                85                  90                  95

Leu Cys Gln Asp His Gly Leu Thr Pro Asp Gln Val Val Ala Ile Ala
                100                 105                 110

Ser Asn Ile Gly Gly Lys Gln Ala Leu Glu Thr Val Gln Arg Leu Leu
```

```
            115                 120                 125
Pro Val Leu Cys Gln Asp His Gly Leu Thr Pro Asp Gln Val Val Ala
            130                 135                 140
Ile Ala Ser His Asp Gly Gly Lys Gln Ala Leu Glu Thr Val Gln Arg
145                 150                 155                 160
Leu Leu Pro Val Leu Cys Gln Asp His Gly Leu Thr Pro Asp Gln Val
                165                 170                 175
Val Ala Ile Ala Ser His Asp Gly Gly Lys Gln Ala Leu Glu Thr Val
            180                 185                 190
Gln Arg Leu Leu Pro Val Leu Cys Gln Asp His Gly Leu Thr Pro Asp
        195                 200                 205
Gln Val Val Ala Ile Ala Ser Asn Gly Gly Lys Gln Ala Leu Glu
    210                 215                 220
Thr Val Gln Arg Leu Leu Pro Val Leu Cys Gln Asp His Gly Leu Thr
225                 230                 235                 240
Pro Asp Gln Val Val Ala Ile Ala Ser Asn Gly Gly Lys Gln Ala
                245                 250                 255
Leu Glu Thr Val Gln Arg Leu Leu Pro Val Leu Cys Gln Asp His Gly
            260                 265                 270
Leu Thr Pro Asp Gln Val Val Ala Ile Ala Ser Asn Ile Gly Gly Lys
        275                 280                 285
Gln Ala Leu Glu Thr Val Gln Arg Leu Leu Pro Val Leu Cys Gln Asp
    290                 295                 300
His Gly Leu Thr Pro Asp Gln Val Val Ala Ile Ala Ser Asn Ile Gly
305                 310                 315                 320
Gly Lys Gln Ala Leu Glu Thr Val Gln Arg Leu Leu Pro Val Leu Cys
                325                 330                 335
Gln Asp His Gly Leu Thr Pro Asp Gln Val Val Ala Ile Ala Ser Asn
            340                 345                 350
Gly Gly Gly Lys Gln Ala Leu Glu Thr Val Gln Arg Leu Leu Pro Val
        355                 360                 365
Leu Cys Gln Asp His Gly Leu Thr Pro Asp Gln Val Val Ala Ile Ala
    370                 375                 380
Ser Asn His Gly Gly Lys Gln Ala Leu Glu Thr Val Gln Arg Leu Leu
385                 390                 395                 400
Pro Val Leu Cys Gln Asp His Gly Leu Thr Pro Asp Gln Val Val Ala
                405                 410                 415
Ile Ala Ser Asn His Gly Gly Lys Gln Ala Leu Glu Thr Val Gln Arg
            420                 425                 430
Leu Leu Pro Val Leu Cys Gln Asp His Gly Leu Thr Pro Asp Gln Val
        435                 440                 445
Val Ala Ile Ala Ser Asn Gly Gly Lys Gln Ala Leu Glu Thr Val
    450                 455                 460
Gln Arg Leu Leu Pro Val Leu Cys Gln Asp His Gly Leu Thr Pro Asp
465                 470                 475                 480
Gln Val Val Ala Ile Ala Ser Asn Ile Gly Gly Lys Gln Ala Leu Glu
                485                 490                 495
Thr Val Gln Arg Leu Leu Pro Val Leu Cys Gln Asp His Gly Leu Thr
            500                 505                 510
Pro Asp Gln Val Val Ala Ile Ala Ser Asn Gly Gly Lys Gln Ala
        515                 520                 525
Leu Glu Thr Val Gln Arg Leu Leu Pro Val Leu Cys Gln Asp His Gly
    530                 535                 540
```

<210> SEQ ID NO 5
<211> LENGTH: 1632
<212> TYPE: DNA
<213> ORGANISM: Artificial Sequence
<220> FEATURE:
<223> OTHER INFORMATION: synthetic construct

<400> SEQUENCE: 5

```
ctgactccgg accaagtggt ggctatcgcc agcaaccacg gcggcaagca agcgctcgaa      60
acggtgcagc ggctgttgcc ggtgctgtgc caggaccatg gctgactcc ggaccaagtg     120
gtggctatcg ccagcaacca cggcggcaag caagcgctcg aaacggtgca gcggctgttg     180
ccggtgctgt gccaggacca tgggctgact ccggaccaag tggtggctat cgccagcaac     240
atcggcggca agcaagcgct cgaaacggtg cagcggctgt tgccggtgct gtgccaggac     300
catgggctga ctccggacca agtggtggct atcgccagca catcggcgg caagcaagcg     360
ctcgaaacgg tgcagcggct gttgccggtg ctgtgccagg accatgggct gactccggac     420
caagtggtgg ctatcgccag ccacgatggc ggcaagcaag cgctcgaaac ggtgcagcgg     480
ctgttgccgg tgctgtgcca ggaccatggg ctgactccgg accaagtggt ggctatcgcc     540
agccacgatg gcggcaagca agcgctcgaa acggtgcagc ggctgttgcc ggtgctgtgc     600
caggaccatg gctgactcc ggaccaagtg gtggctatcg ccagcaacgg tggcggcaag     660
caagcgctcg aaacggtgca gcggctgttg ccggtgctgt gccaggacca tgggctgact     720
ccggaccaag tggtggctat cgccagcaac ggtggcggca agcaagcgct cgaaacggtg     780
cagcggctgt tgccggtgct gtgccaggac catgggctga ctccggacca agtggtggct     840
atcgccagca catcggcgg caagcaagcg ctcgaaacgg tgcagcggct gttgccggtg     900
ctgtgccagg accatgggct gactccggac caagtggtgg ctatcgccag caacatcggc     960
ggcaagcaag cgctcgaaac ggtgcagcgg ctgttgccgg tgctgtgcca ggaccatggg    1020
ctgactccgg accaagtggt ggctatcgcc agcaacggtg gcggcaagca agcgctcgaa    1080
acggtgcagc ggctgttgcc ggtgctgtgc caggaccatg gctgactcc ggaccaagtg    1140
gtggctatcg ccagcaacca cggcggcaag caagcgctcg aaacggtgca gcggctgttg    1200
ccggtgctgt gccaggacca tgggctgact ccggaccaag tggtggctat cgccagcaac    1260
cacggcggca agcaagcgct cgaaacggtg cagcggctgt tgccggtgct gtgccaggac    1320
catgggctga ctccggacca agtggtggct atcgccagca acggtggcgg caagcaagcg    1380
ctcgaaacgg tgcagcggct gttgccggtg ctgtgccagg accatgggct gactccggac    1440
caagtggtgg ctatcgccag caacatcggc ggcaagcaag cgctcgaaac ggtgcagcgg    1500
ctgttgccgg tgctgtgcca ggaccatggg ctgactccgg accaagtggt ggctatcgcc    1560
agcaacggtg gcggcaagca agcgctcgaa acggtgcagc ggctgttgcc ggtgctgtgc    1620
caggaccatg gg                                                       1632
```

<210> SEQ ID NO 6
<211> LENGTH: 544
<212> TYPE: PRT
<213> ORGANISM: Artificial Sequence
<220> FEATURE:
<223> OTHER INFORMATION: synthetic construct

<400> SEQUENCE: 6

```
Leu Thr Pro Asp Gln Val Val Ala Ile Ala Ser Asn Gly Gly Gly Lys
 1               5                  10                  15
```

```
Gln Ala Leu Glu Thr Val Gln Arg Leu Leu Pro Val Leu Cys Gln Asp
                20                  25                  30

His Gly Leu Thr Pro Asp Gln Val Val Ala Ile Ala Ser Asn Gly Gly
            35                  40                  45

Gly Lys Gln Ala Leu Glu Thr Val Gln Arg Leu Leu Pro Val Leu Cys
 50                  55                  60

Gln Asp His Gly Leu Thr Pro Asp Gln Val Val Ala Ile Ala Ser His
 65                  70                  75                  80

Asp Gly Gly Lys Gln Ala Leu Glu Thr Val Gln Arg Leu Leu Pro Val
                85                  90                  95

Leu Cys Gln Asp His Gly Leu Thr Pro Asp Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
        130                 135                 140

Ile Ala Ser His Asp Gly Gly Lys Gln Ala Leu Glu Thr Val Gln Arg
145                 150                 155                 160

Leu Leu Pro Val Leu Cys Gln Asp His Gly Leu Thr Pro Asp Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Asp His Gly Leu Thr Pro Asp
        195                 200                 205

Gln Val Val Ala Ile Ala Ser Asn Gly Gly Gly Lys Gln Ala Leu Glu
        210                 215                 220

Thr Val Gln Arg Leu Leu Pro Val Leu Cys Gln Asp His Gly Leu Thr
225                 230                 235                 240

Pro Asp Gln Val Val Ala Ile Ala Ser Asn Ile Gly Gly Lys Gln Ala
                245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Ser His Asp Gly Gly Lys
        275                 280                 285

Gln Ala Leu Glu Thr Val Gln Arg Leu Leu Pro Val Leu Cys Gln Asp
        290                 295                 300

His Gly Leu Thr Pro Asp Gln Val Val Ala Ile Ala Ser Asn His Gly
305                 310                 315                 320

Gly Lys Gln Ala Leu Glu Thr Val Gln Arg Leu Leu Pro Val Leu Cys
                325                 330                 335

Gln Asp His Gly Leu Thr Pro Asp Gln Val Val Ala Ile Ala Ser Asn
            340                 345                 350

His Gly Gly Lys Gln Ala Leu Glu Thr Val Gln Arg Leu Leu Pro Val
        355                 360                 365

Leu Cys Gln Asp His Gly Leu Thr Pro Asp Gln Val Val Ala Ile Ala
        370                 375                 380

Ser Asn Ile Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                405                 410                 415

Ile Ala Ser His Asp Gly Gly Lys Gln Ala Leu Glu Thr Val Gln Arg
            420                 425                 430
```

```
Leu Leu Pro Val Leu Cys Gln Asp His Gly Leu Thr Pro Asp Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Asp His Gly Leu Thr Pro Asp
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Asp His Gly Leu Thr
            500                 505                 510

Pro Asp Gln Val Val Ala Ile Ala Ser Asn Ile Gly Gly Lys Gln Ala
        515                 520                 525

Leu Glu Thr Val Gln Arg Leu Leu Pro Val Leu Cys Gln Asp His Gly
    530                 535                 540

<210> SEQ ID NO 7
<211> LENGTH: 1632
<212> TYPE: DNA
<213> ORGANISM: Artificial Sequence
<220> FEATURE:
<223> OTHER INFORMATION: synthetic construct

<400> SEQUENCE: 7
ctgactccgg accaagtggt ggctatcgcc agcaacatcg gcggcaagca agcgctcgaa      60
acggtgcagc ggctgttgcc ggtgctgtgc caggaccatg gctgactcc ggaccaagtg     120 gtggctatcg ccagcaacgg tggcggcaag caagcgctcg aaacggtgca gcggctgttg    180
ccggtgctgt gccaggacca tgggctgact ccggaccaag tggtggctat cgccagcaac    240
ggtggcggca agcaagcgct cgaaacggtg cagcggctgt tgccggtgct gtgccaggac    300
catgggctga ctccggacca gtggtggct atcgccagcc acgatggcgg caagcaagcg    360
ctcgaaacgg tgcagcggct gttgccggtg ctgtgccagg accatgggct gactccggac    420
caagtggtgg ctatcgccag caacatcggc ggcaagcaag cgctcgaaac ggtgcagcgg    480
ctgttgccgg tgctgtgcca ggaccatggg ctgactccgg accaagtggt ggctatcgcc    540
agcaaccacg cggcaagca agcgctcgaa acggtgcagc ggctgttgcc ggtgctgtgc    600
caggaccatg gctgactcc ggaccaagtg gtggctatcg ccagcaacca cggcggcaag    660
caagcgctcg aaacggtgca gcggctgttg ccggtgctgt gccaggacca tgggctgact    720
ccggaccaag tggtggctat cgccagccac gatggcggca agcaagcgct cgaaacggtg    780
cagcggctgt tgccggtgct gtgccaggac catgggctga ctccggacca gtggtggct    840 atcgccagca acatcggcgg caagcaagcg ctcgaaacgg tgcagcggct gttgccggtg    900
ctgtgccagg accatgggct gactccggac caagtggtgg ctatcgccag caacggtggc    960
ggcaagcaag cgctcgaaac ggtgcagcgg ctgttgccgg tgctgtgcca ggaccatggg   1020
ctgactccgg accaagtggt ggctatcgcc agcaacggtg gcggcaagca agcgctcgaa   1080
acggtgcagc ggctgttgcc ggtgctgtgc caggaccatg gctgactcc ggaccaagtg   1140 gtggctatcg ccagccacga tggcggcaag caagcgctcg aaacggtgca gcggctgttg   1200
ccggtgctgt gccaggacca tgggctgact ccggaccaag tggtggctat cgccagccac   1260
gatggcggca agcaagcgct cgaaacggtg cagcggctgt tgccggtgct gtgccaggac   1320
catgggctga ctccggacca gtggtggct atcgccagcc acgatggcgg caagcaagcg   1380
ctcgaaacgg tgcagcggct gttgccggtg ctgtgccagg accatgggct gactccggac   1440
```

```
caagtggtgg ctatcgccag caacggtggc ggcaagcaag cgctcgaaac ggtgcagcgg    1500
ctgttgccgg tgctgtgcca ggaccatggg ctgactccgg accaagtggt ggctatcgcc    1560
agcaacggtg gcggcaagca agcgctcgaa acggtgcagc ggctgttgcc ggtgctgtgc    1620
caggaccatg gg                                                        1632
```

<210> SEQ ID NO 8
<211> LENGTH: 544
<212> TYPE: PRT
<213> ORGANISM: Artificial Sequence
<220> FEATURE:
<223> OTHER INFORMATION: synthetic construct

<400> SEQUENCE: 8

```
Leu Thr Pro Asp Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly Leu Thr Pro Asp Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Asp His Gly Leu Thr Pro Asp Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Asp His Gly Leu Thr Pro Asp Gln Val Val Ala Ile Ala
            100                 105                 110

Ser Asn Ile Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Asp His Gly Leu Thr Pro Asp Gln Val
                165                 170                 175

Val Ala Ile Ala Ser Asn His Gly Gly Lys Gln Ala Leu Glu Thr Val
            180                 185                 190

Gln Arg Leu Leu Pro Val Leu Cys Gln Asp His Gly Leu Thr Pro Asp
        195                 200                 205

Gln Val Val Ala Ile Ala Ser Asn His Gly Gly Lys Gln Ala Leu Glu
    210                 215                 220

Thr Val Gln Arg Leu Leu Pro Val Leu Cys Gln Asp His Gly Leu Thr
225                 230                 235                 240

Pro Asp Gln Val Val Ala Ile Ala Ser Asn His Gly Gly Lys Gln Ala
                245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Ser Asn Ile Gly Gly Lys
        275                 280                 285

Gln Ala Leu Glu Thr Val Gln Arg Leu Leu Pro Val Leu Cys Gln Asp
    290                 295                 300

His Gly Leu Thr Pro Asp Gln Val Val Ala Ile Ala Ser Asn Gly Gly
305                 310                 315                 320

Gly Lys Gln Ala Leu Glu Thr Val Gln Arg Leu Leu Pro Val Leu Cys
```

|     | 325 |     |     |     | 330 |     |     |     | 335 |     |     |
| --- | --- | --- | --- | --- | --- | --- | --- | --- | --- | --- | --- |

Gln Asp His Gly Leu Thr Pro Asp Gln Val Ala Ile Ala Ser Asn
           340                    345               350

His Gly Gly Lys Gln Ala Leu Glu Thr Val Gln Arg Leu Leu Pro Val
        355                   360               365

Leu Cys Gln Asp His Gly Leu Thr Pro Asp Gln Val Ala Ile Ala
370                 375                 380

Ser Asn Ile Gly Gly Lys Gln Ala Leu Glu Thr Val Gln Arg Leu Leu
385                 390               395              400

Pro Val Leu Cys Gln Asp His Gly Leu Thr Pro Asp Gln Val Ala
           405                  410              415

Ile Ala Ser Asn His Gly Gly Lys Gln Ala Leu Glu Thr Val Gln Arg
        420                 425               430

Leu Leu Pro Val Leu Cys Gln Asp His Gly Leu Thr Pro Asp Gln Val
           435                  440             445

Val Ala Ile Ala Ser Asn Gly Gly Gly Lys Gln Ala Leu Glu Thr Val
        450                 455               460

Gln Arg Leu Leu Pro Val Leu Cys Gln Asp His Gly Leu Thr Pro Asp
465                 470               475              480

Gln Val Val Ala Ile Ala Ser Asn Gly Gly Gly Lys Gln Ala Leu Glu
               485               490               495

Thr Val Gln Arg Leu Leu Pro Val Leu Cys Gln Asp His Gly Leu Thr
        500                 505               510

Pro Asp Gln Val Val Ala Ile Ala Ser Asn His Gly Gly Lys Gln Ala
           515                  520             525

Leu Glu Thr Val Gln Arg Leu Leu Pro Val Leu Cys Gln Asp His Gly
        530                 535               540

<210> SEQ ID NO 9
<211> LENGTH: 1632
<212> TYPE: DNA
<213> ORGANISM: Artificial Sequence
<220> FEATURE:
<223> OTHER INFORMATION: synthetic construct

<400> SEQUENCE: 9

```
ctgactccgg accaagtggt ggctatcgcc agcaacatcg gcggcaagca agcgctcgaa      60
acggtgcagc ggctgttgcc ggtgctgtgc caggaccatg gctgactccc ggaccaagtg     120
gtggctatcg ccagccacga tggcggcaag caagcgctcg aaacggtgca gcggctgttg     180
ccggtgctgt gccaggacca tgggctgact ccggaccaag tggtggctat cgccagcaac     240
ggtggcggca agcaagcgct cgaaacggtg cagcggctgt tgccggtgct gtgccaggac     300
catgggctga ctccggacca agtggtggct atcgccagca acatcggcgg caagcaagcg     360
ctcgaaacgg tgcagcggct gttgccggtg ctgtgccagg accatgggct gactccggac     420
caagtggtgg ctatcgccag caacggtggc ggcaagcaag cgctcgaaac ggtgcagcgg     480
ctgttgccgg tgctgtgcca ggaccatggg ctgactccgg accaagtggt ggctatcgcc     540
agcaaccacg gcggcaagca agcgctcgaa acggtgcagc ggctgttgcc ggtgctgtgc     600
caggaccatg ggctgactcc ggaccaagtg gtggctatcg ccagcaacca cggcggcaag     660
caagcgctcg aaacggtgca gcggctgttg ccggtgctgt gccaggacca tgggctgact     720
ccggaccaag tggtggctat cgccagcaac acggcggca agcaagcgct cgaaacggtg     780
cagcggctgt tgccggtgct gtgccaggac catgggctga ctccggacca agtggtggct     840
```

| | |
|---|---|
| atcgccagca acatcggcgg caagcaagcg ctcgaaacgg tgcagcggct gttgccggtg | 900 |
| ctgtgccagg accatgggct gactccggac caagtggtgg ctatcgccag caacggtggc | 960 |
| ggcaagcaag cgctcgaaac ggtgcagcgg ctgttgccgg tgctgtgcca ggaccatggg | 1020 |
| ctgactccgg accaagtggt ggctatcgcc agcaaccacg gcggcaagca agcgctcgaa | 1080 |
| acggtgcagc ggctgttgcc ggtgctgtgc caggaccatg gctgactcc ggaccaagtg | 1140 |
| gtggctatcg ccagcaacat cggcggcaag caagcgctcg aaacggtgca gcggctgttg | 1200 |
| ccggtgctgt gccaggacca tgggctgact ccggaccaag tggtggctat cgccagcaac | 1260 |
| cacggcggca agcaagcgct cgaaacggtg cagcggctgt tgccggtgct gtgccaggac | 1320 |
| catgggctga ctccggacca agtggtggct atcgccagca acggtggcgg caagcaagcg | 1380 |
| ctcgaaacgg tgcagcggct gttgccggtg ctgtgccagg accatgggct gactccggac | 1440 |
| caagtggtgg ctatcgccag caacggtggc ggcaagcaag cgctcgaaac ggtgcagcgg | 1500 |
| ctgttgccgg tgctgtgcca ggaccatggg ctgactccgg accaagtggt ggctatcgcc | 1560 |
| agcaaccacg gcggcaagca agcgctcgaa acggtgcagc ggctgttgcc ggtgctgtgc | 1620 |
| caggaccatg gg | 1632 |

<210> SEQ ID NO 10
<211> LENGTH: 544
<212> TYPE: PRT
<213> ORGANISM: Artificial Sequence
<220> FEATURE:
<223> OTHER INFORMATION: synthetic construct

<400> SEQUENCE: 10

```
Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly Leu Thr Pro Asp Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Asp His Gly Leu Thr Pro Asp Gln Val Val Ala Ile Ala Ser Asn
65                  70                  75                  80

Ile Gly Gly Lys Gln Ala Leu Glu Thr Val Gln Arg Leu Leu Pro Val
                85                  90                  95

Leu Cys Gln Asp His Gly Leu Thr Pro Asp Gln Val Val Ala Ile Ala
            100                 105                 110

Ser Asn Ile Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Asp His Gly Leu Thr Pro Asp Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Asp His Gly Leu Thr Pro Asp
        195                 200                 205

Gln Val Val Ala Ile Ala Ser Asn Gly Gly Gly Lys Gln Ala Leu Glu
    210                 215                 220
```

Thr Val Gln Arg Leu Leu Pro Val Leu Cys Gln Asp His Gly Leu Thr
225                 230                 235                 240

Pro Asp Gln Val Val Ala Ile Ala Ser His Asp Gly Gly Lys Gln Ala
            245                 250                 255

Leu Glu Thr Val Gln Arg Leu Leu Pro Val Leu Cys Gln Asp His Gly
        260                 265                 270

Leu Thr Pro Asp Gln Val Val Ala Ile Ala Ser His Asp Gly Gly Lys
    275                 280                 285

Gln Ala Leu Glu Thr Val Gln Arg Leu Leu Pro Val Leu Cys Gln Asp
290                 295                 300

His Gly Leu Thr Pro Asp Gln Val Val Ala Ile Ala Ser His Asp Gly
305                 310                 315                 320

Gly Lys Gln Ala Leu Glu Thr Val Gln Arg Leu Leu Pro Val Leu Cys
            325                 330                 335

Gln Asp His Gly Leu Thr Pro Asp Gln Val Val Ala Ile Ala Ser His
        340                 345                 350

Asp Gly Gly Lys Gln Ala Leu Glu Thr Val Gln Arg Leu Leu Pro Val
    355                 360                 365

Leu Cys Gln Asp His Gly Leu Thr Pro Asp Gln Val Val Ala Ile Ala
370                 375                 380

Ser Asn Ile Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
            405                 410                 415

Ile Ala Ser Asn His Gly Gly Lys Gln Ala Leu Glu Thr Val Gln Arg
        420                 425                 430

Leu Leu Pro Val Leu Cys Gln Asp His Gly Leu Thr Pro Asp Gln Val
    435                 440                 445

Val Ala Ile Ala Ser Asn Gly Gly Gly Lys Gln Ala Leu Glu Thr Val
450                 455                 460

Gln Arg Leu Leu Pro Val Leu Cys Gln Asp His Gly Leu Thr Pro Asp
465                 470                 475                 480

Gln Val Val Ala Ile Ala Ser Asn His Gly Gly Lys Gln Ala Leu Glu
            485                 490                 495

Thr Val Gln Arg Leu Leu Pro Val Leu Cys Gln Asp His Gly Leu Thr
        500                 505                 510

Pro Asp Gln Val Val Ala Ile Ala Ser Asn Gly Gly Gly Lys Gln Ala
    515                 520                 525

Leu Glu Thr Val Gln Arg Leu Leu Pro Val Leu Cys Gln Asp His Gly
530                 535                 540

<210> SEQ ID NO 11
<211> LENGTH: 1632
<212> TYPE: DNA
<213> ORGANISM: Artificial Sequence
<220> FEATURE:
<223> OTHER INFORMATION: synthetic construct

<400> SEQUENCE: 11
ctgactccgg accaagtggt ggctatcgcc agcaacggtg gcggcaagca agcgctcgaa      60
acggtgcagc ggctgttgcc ggtgctgtgc caggaccatg gctgactccg gaccaagtg     120 gtggctatcg ccagcaacgg tgcggcaag caagcgctcg aaacggtgca gcggctgttg     180
ccggtgctgt gccaggacca tgggctgact ccggaccaag tggtggctat cgccagcaac     240

```
atcggcggca agcaagcgct cgaaacggtg cagcggctgt tgccggtgct gtgccaggac      300
catgggctga ctccggacca agtggtggct atcgccagca acatcggcgg caagcaagcg      360
ctcgaaacgg tgcagcggct gttgccggtg ctgtgccagg accatgggct gactccggac      420
caagtggtgg ctatcgccag caacggtggc ggcaagcaag cgctcgaaac ggtgcagcgg      480
ctgttgccgg tgctgtgcca ggaccatggg ctgactccgg accaagtggt ggctatcgcc      540
agccacgatg gcggcaagca agcgctcgaa acggtgcagc ggctgttgcc ggtgctgtgc      600
caggaccatg gctgactcc ggaccaagtg gtggctatcg ccagcaacgg tggcggcaag      660
caagcgctcg aaacggtgca gcggctgttg ccggtgctgt gccaggacca tgggctgact      720
ccggaccaag tggtggctat cgccagccac gatggcggca agcaagcgct cgaaacggtg      780
cagcggctgt tgccggtgct gtgccaggac catgggctga ctccggacca agtggtggct      840
atcgccagcc acgatggcgg caagcaagcg ctcgaaacgg tgcagcggct gttgccggtg      900
ctgtgccagg accatgggct gactccggac caagtggtgg ctatcgccag ccacgatggc      960
ggcaagcaag cgctcgaaac ggtgcagcgg ctgttgccgg tgctgtgcca ggaccatggg     1020
ctgactccgg accaagtggt ggctatcgcc agccacgatg gcggcaagca agcgctcgaa     1080
acggtgcagc ggctgttgcc ggtgctgtgc caggaccatg gctgactcc ggaccaagtg     1140 gtggctatcg ccagcaacat cggcggcaag caagcgctcg aaacggtgca gcggctgttg     1200
ccggtgctgt gccaggacca tgggctgact ccggaccaag tggtggctat cgccagcaac     1260
cacggcggca agcaagcgct cgaaacggtg cagcggctgt tgccggtgct gtgccaggac     1320
catgggctga ctccggacca agtggtggct atcgccagca acgtggcgg caagcaagcg     1380 ctcgaaacgg tgcagcggct gttgccggtg ctgtgccagg accatgggct gactccggac     1440
caagtggtgg ctatcgccag caaccacggc ggcaagcaag cgctcgaaac ggtgcagcgg     1500
ctgttgccgg tgctgtgcca ggaccatggg ctgactccgg accaagtggt ggctatcgcc     1560
agcaacggtg gcggcaagca agcgctcgaa acggtgcagc ggctgttgcc ggtgctgtgc     1620
caggaccatg gg                                                         1632

<210> SEQ ID NO 12
<211> LENGTH: 7753
<212> TYPE: DNA
<213> ORGANISM: Artificial Sequence
<220> FEATURE:
<223> OTHER INFORMATION: synthetic construct

<400> SEQUENCE: 12
ctgacgcgcc ctgtagcggc gcattaagcg cggcgggtgt ggtggttacg cgcagcgtga       60
ccgctacact tgccagcgcc ctagcgcccg ctcctttcgc tttcttccct tcctttctcg      120
ccacgttcgc cggctttccc cgtcaagctc taaatcgggg gctcccttta gggttccgat      180
ttagtgcttt acggcacctc gaccccaaaa aacttgatta gggtgatggt tcacgtagtg      240
ggccatcgcc ctgatagacg gtttttcgcc ctttgacgtt ggagtccacg ttctttaata      300
gtggactctt gttccaaact ggaacaacac tcaaccctat ctcggtctat tcttttgatt      360
tataagggat tttgccgatt tcggcctatt ggttaaaaaa tgagctgatt taacaaaaat      420
ttaacgcgaa ttttaacaaa atattaacgc ttacaatttc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcgtaata cgactcacta tagggcgaat tggagctcca      660
```

```
ccgcggtggc ggccgctcta gaactagtgg atccccgggg ctgcaggaat tcgatatcaa    720
gcttatcgat accgtcgacc tcgagagcag cactaaattt gtctgggtga gtcagagaag    780
gctaaccagg aaaatagtt  tctgaactaa cacttgaagg aggtgtagca gttcatcact    840
gacagtgatg ttggggtggg tctggtttca ggagagggga ggaaattggc tttggtctga    900
ggctgaggtg tgggcaaagc attagcttat gtgggtccat tagcttatgt gagtccacaa    960
aaggtgtgtg tgtgttttgt gtatgtgtg  tgtgtgtg   tgtgtgtg   tgtgtacgaa   1020 atgggggctc aatgatttgg tagtggtttg gtttgtcaag aagcaggctg ggaactcaat   1080
aagcatcttt ccattcattt ctactgtgta tcccacagct tcacacacac atgcacattt   1140
caacattggt gactgcttca cttgcacacc taaggtaatg atggacacac ctgtagcaat   1200
gtagattctt cctaagctaa taattagttt caggaggtag cacatacatt taaaaatagg   1260
ttaaaataaa gtgttatttt aattggtagg tgatctgtt  ggcaccaatg attattcacg   1320
gcatcaagac ccagggtgcc cgtcagaagt tctccagcct ctacatctct cagtttatca   1380
tcatgtatag tcttgatggg aagaagtggc agacttatcg aggaaattcc actggaacct   1440
taatggtctt ctttggcaat gtggattcat ctgggataaa acacaatatt tttaaccctc   1500
caattattgc tcgatacatc cgtttgcacc caactcatta tagcattcgc agcactcttc   1560
gcatggagtt gatgggctgt gatttaaata gttgcagcat gccattggga atggagagta   1620
aagcaatatc agatgcacag attactgctt catcctactt taccaatatg tttgccacct   1680
ggtctccttc aaaagctcga cttcacctcc aagggaggag taatgcctgg agacctcagg   1740
tgaataatcc aaaagagtgg ctgcaagtgg acttccagaa gacagtgaaa gtcacaggag   1800
taactactca gggagtaaaa tctctgctta ccagcatgta tgtgaaggag ttcctcatct   1860
ccagcagtca agatggccat cagtggactc tcttttttca gaatggcaaa gtaaaggttt   1920 ttcaggggaaa tcaagactcc ttcacacctg tggtgaactc tctagaccca ccgttactga   1980
ctcgctacct tcgaattcac ccccagagtt gggtgcacca gattgccctg aggatggagg   2040
ttctgggctg cgaggcacag gacctctact agccgcggtg aagcttgatg ggtggcatcc   2100
ctgtgacccc tccccagtgc ctctcctggc cctggaagtt gccactccag tgcccaccag   2160
ccttgtccta ataaaattaa gttgcatcat tttgtctgac taggtgtcct tctataatat   2220 tatgggtgg  aggggtgg   tatggagcaa ggggcaagtt gggaagacaa cctgtagggc   2280
ctgcggggtc tattgggaac caagctggag tgcagtggca caatcttggc tcactgcaat   2340
ctccgcctcc tgggttcaag cgattctcct gcctcagcct cccgagttgt gggattcca   2400 ggcatgcatg accaggctca gctaattttt gtttttttgg tagagacggg gtttcaccat   2460
attggccagg ctggtctcca actcctaatc tcaggtgatc tacccacctt ggcctcccaa   2520
attgctggga ttacaggcgt gaaccactgc tcccttccct gtccttctga ttttaaaata   2580
actataccag caggaggacg tccagacaca gcataggcta cctggccatg cccaaccggt   2640
gggacatttg agttgcttgc ttggcactgt cctctcatgc gttgggtcca ctcagtagat   2700
gcctgttgcc tgaatacttt aaagaatttt ggcagatttc agatattgga caaacactct   2760
tagcttccac aaacttaatt ccaaaaaata atttttcact tatgagcaat agagttatta   2820
cggacatatc agcaaaaatg tagtagtgtc aaggctcata gatgatagaa atgaagagat   2880
gctgtattga tagaaatatg tgattcagga ctgtgtggat tgatgattgt gagcttgctt   2940
atggatatcc taggtttgag gttatagtag gacaatcagg ttgaaatgtc cagcaggcag   3000
```

```
taggtgaaag acaagtttag ggggcaaaac catggatgga gatgaagatt catgacttcc      3060
acataaaagg atgggtgaaa ctttgggaat tgatgaattc tctagaggtg agctcaagac      3120
ccttaaaggc ttaaaacctc agcgttattg tctactcttc cctcattttt atgcccacaa      3180
atctggtcaa tcctttattt gcaatgcctc tcacatctct ttcttctgtt tccatttata      3240
ccgctgttgc cacagcccag ggtcccatca cctcacactt gatctattgt attacattcc      3300
taactagtct tcccccgttt ctaatctgtt ctccgataaa agctgcacat cattttcagg      3360
ataatcatca gtcgcctgcc taaaactttt caatgtcttc ccattgtaaa tgagtcttcg      3420
gacctcgcgg gggccgctta agcggtggtt agggtttgtc tgacgcgggg ggaggggggaa      3480 ggaacgaaac actctcattc ggaggcggct cggggtttgg tcttggtggc cacgggcacg      3540
cagaagagcg ccgcgatcct cttaagcacc ccccgccct ccgtggaggc ggggggtttgg    3600 tcggcgggtg gtaactggcg ggccgctgac tcggcgggt cgcgcgcccc agagtgtgac      3660
cttttcggtc tgctcgcaga cccccggggcg gcgccgccgc ggcggcgacg ggctcgctgg      3720
gtcctaggct ccatggggac cgtatacgtg acaggctct ggagcatccg cacgactgcg      3780
gtgatattac cggagaccttt ctgcgggacg agccgggtca cgcggctgac gcggagcgtc      3840
cgttgggcga caaacaccag gacggggcac aggtacacta tcttgtcacc cggaggcgcg      3900
agggactgca ggagcttcag ggagtggcgc agctgcttca tccccgtggc ccgttgctcg      3960
cgtttgctgg cggtgtcccc ggaagaaata tatttgcatg tctttagttc tatgatgaca      4020
caaaccccgc ccagcgtctt gtcattggcg aattcgaaca cgcagatgca gtcggggcgg      4080
cgcggtccca ggtccacttc gcatattaag gtgacgcgtg tggcctcgaa caccgagcga      4140
ccctgcagcg accgcttaa atggcttcgt accctgcca tcaacacgcg tctgcgttcg       4200
accaggctgc gcgttctcgc ggccataaca accgacgtac ggcgttgcgc cctcgccggc      4260
aacaaaaagc cacggaagtc cgcctggagc agaaaatgcc cacgctactg cgggtttata      4320
tagacggtcc ccacgggatg gggaaaacca ccaccacgca actgctggtg gccctgggtt      4380
cgcgcgacga tatcgtctac gtacccgagc cgatgactta ctggcgggtg ttgggggctt      4440
ccgagacaat cgcgaacatc tacaccacac aacaccgcct cgaccagggt gagatatcgg      4500
ccggggacgc ggcggtggta atgacaagcg cccagataac aatgggcatg ccttatgccg      4560
tgaccgacgc cgttctggct cctcatatcg ggggggaggc tgggagctca catgcccgc      4620 cccggccct caccctcatc ttcgaccgcc atccatcgc cgccctcctg tgctacccgg      4680
ccgcgcgata cctattgggc agcatgaccc ccaggccgt gctggcgttc gtggccctca      4740
tcccgccgac cttgcccggc acaaacatcg tgttggggc ccttccggag acagacaca       4800 tcgaccgcct ggccaaacgc cagcgccccg gcgagcggct tgacctggct atgctggccg      4860
cgattcgccg cgtttatggg ctgcttgcca atacggtgcg gtatctgcag ggcggcgggt      4920
cgtggcggga ggattgggga cagctttcgg gggcggccgt gccgcccag ggtgccgagc      4980 cccagagcaa cgcgggccca cgaccccata tcggggacac gttatttacc ctgtttcggg      5040 ccccgagtt gctggcccc aacggcgacc tgtataacgt gttttgcctgg gctttggacg      5100 tcttggccaa acgcctccgt cccatgcatg tctttatcct ggattacgac caatcgcccg      5160
ccggctgccg ggacgccctg ctgcaactta cctccgggat ggtccagacc cacgtcacca      5220
ccccaggctc cataccgacg atctgcgacc tggcgcgcac gtttgccggg agatgggggg      5280
aggctaactg aaacacggaa ggagacaata ccggaaggaa cccgcgctat gacggcaata      5340 aaagacaga ataaaacgca cgggtgttgg gtcgtttgtt cataaacgcg gggttcggtc       5400
```

```
ccagggctgg cactctgtcg atacccacc gagaccccat tgggaccaat acgcccgcgt    5460
ttcttccttt tccccacccc aaccccaag ttcgggtgaa ggcccagggc tcgcagccaa    5520
cgtcggggcg gcaagccctg ccataggta cccagctttt gttcccttta gtgagggtta    5580
attgcgcgct tggcgtaatc atggtcatag ctgtttcctg tgtgaaattg ttatccgctc    5640
acaattccac acaacatacg agccggaagc ataaagtgta agcctgggg tgcctaatga    5700 gtgagctaac tcacattaat tgcgttgcgc tcactgcccg ctttccagtc gggaaacctg    5760
tcgtgccagc tgcattaatg aatcggccaa cgcgcgggga gaggcggttt gcgtattggg    5820
cgctcttccg cttcctcgct cactgactcg ctgcgctcgg tcgttcggct gcggcgagcg    5880
gtatcagctc actcaaaggc ggtaatacgg ttatccacag aatcagggga taacgcagga    5940
aagaacatgt gagcaaaagg ccagcaaaag gccaggaacc gtaaaaaggc cgcgttgctg    6000 gcgttttcc ataggctccg ccccctgac gagcatcaca aaaatcgacg ctcaagtcag    6060
aggtggcgaa acccgacagg actataaaga taccaggcgt ttccccctgg aagctccctc    6120
gtgcgctctc ctgttccgac cctgccgctt accggatacc tgtccgcctt tctcccttcg    6180
ggaagcgtgg cgctttctca tagctcacgc tgtaggtatc tcagttcggt gtaggtcgtt    6240
cgctccaagc tgggctgtgt gcacgaaccc cccgttcagc ccgaccgctg cgccttatcc    6300
ggtaactatc gtcttgagtc aacccggta agacacgact tatcgccact ggcagcagcc    6360
actggtaaca ggattagcag agcgaggtat gtaggcggtg ctacagagtt cttgaagtgg    6420
tggcctaact acggctacac tagaaggaca gtatttggta tctgcgctct gctgaagcca    6480
gttaccttcg gaaaaagagt tggtagctct tgatccggca acaaaccac cgctggtagc    6540 ggtggttttt ttgtttgcaa gcagcagatt acgcgcagaa aaaaaggatc tcaagaagat    6600
cctttgatct tttctacggg gtctgacgct cagtggaacg aaaactcacg ttaagggatt    6660
ttggtcatga gattatcaaa aaggatcttc acctagatcc ttttaaatta aaaatgaagt    6720
tttaaatcaa tctaaagtat atatgagtaa acttggtctg acagttacca atgcttaatc    6780
agtgaggcac ctatctcagc gatctgtcta tttcgttcat ccatagttgc ctgactcccc    6840
gtcgtgtaga taactacgat acgggagggc ttaccatctg gccccagtgc tgcaatgata    6900
ccgcgagacc cacgctcacc ggctccagat ttatcagcaa taaaccagcc agccggaagg    6960
gccgagcgca gaagtggtcc tgcaacttta tccgcctcca tccagtctat taattgttgc    7020
cgggaagcta gagtaagtag ttcgccagtt aatagtttgc gcaacgttgt tgccattgct    7080
acaggcatcg tggtgtcacg ctcgtcgttt ggtatggctt cattcagctc cggttcccaa    7140
cgatcaaggc gagttacatg atcccccatg ttgtgcaaaa aagcggttag ctccttcggt    7200
cctccgatcg ttgtcagaag taagttggcc gcagtgttat cactcatggt tatggcagca    7260
ctgcataatt ctcttactgt catgccatcc gtaagatgct tttctgtgac tggtgagtac    7320
tcaaccaagt cattctgaga atagtgtatg cggcgaccga gttgctcttg cccggcgtca    7380
atacgggata ataccgcgcc acatagcaga actttaaaag tgctcatcat tggaaaacgt    7440
tcttcggggc gaaaactctc aaggatctta ccgctgttga gatccagttc gatgtaaccc    7500
actcgtgcac ccaactgatc ttcagcatct tttactttca ccagcgtttc tgggtgagca    7560
aaaacaggaa ggcaaaatgc cgcaaaaaag ggaataaggg cgacacggaa atgttgaata    7620
ctcatactct tccttttca atattattga agcatttatc agggttattg tctcatgagc    7680
ggatacatat ttgaatgtat ttagaaaaat aaacaaatag gggttccgcg cacatttccc    7740
```
cgaaaagtgc cac                                                             7753

<210> SEQ ID NO 13
<211> LENGTH: 11418
<212> TYPE: DNA
<213> ORGANISM: Artificial Sequence
<220> FEATURE:
<223> OTHER INFORMATION: synthetic construct

<400> SEQUENCE: 13

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggctttccc cgtcaagctc taaatcgggg gctcccttta gggttccgat    180
ttagtgcttt acggcacctc gaccccaaaa aacttgatta gggtgatggt tcacgtagtg    240
ggccatcgcc ctgatagacg gttttcgcc ctttgacgtt ggagtccacg ttctttaata    300
gtggactctt gttccaaact ggaacaacac tcaaccctat ctcggtctat tcttttgatt    360
tataagggat tttgccgatt tcggcctatt ggttaaaaaa tgagctgatt taacaaaaat    420
ttaacgcgaa ttttaacaaa atattaacgc ttacaatttc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat ggagctcca    660
ccgcggtggc ggccgctcta gaactagtgg atccccccggg ctgcaggaat tcgatatcaa    720
gcttatcgat accgtcgacc tcgagaggat tctgagaaga ggagtgacag gactcgcttt    780
atagttttaa attataacta taaattatag tttttaaaac aatagttgcc taacctcatg    840
ttatatgtaa aactacagtt ttaaaaacta taaattcctc atactggcag cagtgtgagg    900
ggcaagggca aaagcagaga gactaacagg ttgctggtta ctcttgctag tgcaagtgaa    960
ttctagaatc ttcgacaaca tccagaactt ctccttgctgc tgccactcag gaagaggggtt   1020
ggagtaggct aggaatagga gcacaaatta aagctcctgt tcactttgac ttctccatcc   1080
ctctcctcct ttccttaaag gttctgatta aagcagactt atgccctac tgctctcaga   1140
agtgaatggg ttaagtttag cagcctccct tttgctactt cagttcttcc tgtggctgct   1200
tcccactgat aaaaggaag caatcctatc ggttactgct tagtgctgag cacatccagt   1260
gggtaaagtt ccttaaaatg ctctgcaaag aaattggac ttttcattaa atcagaaatt   1320
ttactttttt cccctcctgg gagctaaaga tattttagag aagaattaac cttttgcttc   1380
tccagttgaa catttgtagc aataagtcat gcaaatagag ctctccacct gcttctttct   1440
gtgccttttg cgattctgct ttagtgccac cagaagatac tacctgggtg cagtggaact   1500
gtcatgggac tatatgcaaa gtgatctcgg tgagctgcca tttcctccta gagtgccaaa   1560
atcttttcca ttcaacacct cagtcgtgta caaaaagact ctgtttgtag aattcacgga   1620
tcaccttttc aacatcgcta agccaaggcc accctggatg ggtctgctag gtcctaccat   1680
ccaggctgag gtttatgata cagtggtcat tacacttaag aacatggctt cccatcctgt   1740
cagtcttcat gctgttggtg tatcctactg gaaagcttct gagggagctg aatatgatga   1800
tcagaccagt caaagggaga agaagatga taaagtcttc cctggtggaa gccatacata   1860
tgtctggcag gtcctgaaag agaatggtcc aatggcctct gacccactgt gccttaccta   1920
ctcatatctt tctcatgtgg acctggtaaa agacttgaat tcaggcctca ttggagccct   1980
actagtatgt agagaaggga gtctggccaa ggaaaagaca cagaccttgc acaaatttat   2040
```

```
actactttt  gctgtatttg  atgaagggaa  aagttggcac  tcagaaacaa  agaactcctt    2100
gatgcaggat  agggatgctg  catctgctcg  ggcctggcct  aaaatgcaca  cagtcaatgg    2160
ttatgtaaac  aggtctctgc  caggtctgat  tggatgccac  aggaaatcag  tctattggca    2220
tgtgattgga  atgggcacca  ctcctgaagt  gcactcaata  ttcctcgaag  gtcacacatt    2280
tcttgtgagg  aaccatcgcc  aggcgtcctt  ggaaatctcg  ccaataactt  tccttactgc    2340
tcaaacactc  ttgatggacc  ttggacagtt  tctactgttt  tgtcatatct  cttcccacca    2400
acatgatggc  atggaagctt  atgtcaaagt  agacagctgt  ccagaggaac  cccaactacg    2460
aatgaaaaat  aatgaagaag  cggaagacta  tgatgatgat  cttactgatt  ctgaaatgga    2520
tgtggtcagg  tttgatgatg  acaactctcc  ttcctttatc  caattcgct  cagttgccaa     2580 gaagcatcct  aaaacttggg  tacattacat  tgctgctgaa  gaggaggact  gggactatgc    2640
tcccttagtc  ctcgccccg  atgacagaag  ttataaaagt  caatatttga  acaatggccc     2700
tcagcggatt  ggtaggaagt  acaaaaaagt  ccgatttatg  gcatacacag  atgaaacctt    2760
taagactcgt  gaagctattc  agcatgaatc  aggaatcttg  ggacctttac  tttatgggga    2820
agttggagac  acactgttga  ttatatttaa  gaatcaagca  agcagaccat  ataacatcta    2880
ccctcacgga  atcactgatg  tccgtccttt  gtattcaagg  agattaccaa  aggtgtaaa     2940 acatttgaag  gattttccaa  ttctgccagg  agaaatattc  aaatataaat  ggacagtgac    3000
tgtagaagat  gggccaacta  atcagatcc  tcggtgcctg  acccgctatt  actctagttt     3060
cgttaatatg  gagagagatc  tagcttcagg  actcattggc  cctctcctca  tctgctacaa    3120
agaatctgta  gatcaaagag  gaaaccagat  aatgtcagac  aagaggaatg  tcatcctgtt    3180 ttctgtatt  tgatgagaacc  gaagctggta  cctcacagag  aatatacaac  gctttctccc    3240
caatccagct  ggagtgcagc  ttgaggatcc  agagttccaa  gcctccaaca  tcatgcacag    3300
catcaatggc  tatgttttg  atagtttgca  gttgtcagtt  tgtttgcatg  aggtggcata     3360
ctggtacatt  ctaagcattg  gagcacagac  tgacttcctt  tctgtcttct  tctctggata    3420
taccttcaaa  cacaaaatgg  tctatgaaga  cacactcacc  ctattcccat  tctcaggaga    3480
aactgtcttc  atgtcgatgg  aaaacccagg  tctatggatt  ctggggtgcc  acaactcaga    3540
ctttcggaac  agaggcatga  ccgccttact  gaaggtttct  agttgtgaca  agaacactgg    3600
tgattattac  gaggacagtt  atgaagatat  ttcagcatac  ttgctgagta  aaacaatgc     3660 cattgaacca  agaagcttct  cccaaaaccc  accagtcttg  aaacgccatc  aacgggaaat    3720
aactcgtact  actcttcagt  cagatcaaga  ggaaattgac  tatgatgata  ccatatcagt    3780
tgaaatgaag  aaggaagatt  ttgacattta  tgatgaggat  gaaaatcaga  gccccgcag     3840 ctttcaaaag  aaaacacgac  actattttat  tgctgcagtg  gagaggctct  gggattatgg    3900
gatgagtagc  tccccacatg  ttctaagaaa  cagggctcag  agtggcagtg  tccctcagtt    3960
caagaaagtt  gttttccagg  aatttactga  tggctccttt  actcagccct  ataccgtgg     4020 agaactaaat  gaacatttgg  gactcctggg  gccatatata  agagcagaag  ttgaagataa    4080
tatcatggta  actttcagaa  atcaggcctc  tcgtccctat  tccttctatt  ctagccttat    4140
ttcttatgag  gaagatcaga  ggcaaggagc  agaacctaga  aaaaactttg  tcaagcctaa    4200
tgaaaccaaa  acttactttt  ggaaagtgca  acatcatatg  gcacccacta  aagatgagtt    4260
tgactgcaaa  gcctgggctt  atttctctga  tgttgacctg  gaaaaagatg  tgcactcagg    4320
cctgattgga  ccccttctgg  tctgccacac  taacacactg  aaccctgctc  atgggagaca    4380
```

```
agtgacagta caggaatttg ctctgttttt caccatctttt gatgagacca aaagctggta    4440
cttcactgaa aatatggaaa gaaactgcag ggctccctgc aatatccaga tggaagatcc    4500
cacttttaaa gagaattatc gcttccatgc aatcaatggc tacataatgg atacactacc    4560
tggcttagta atggctcagg atcaaaggat tcgatggtat ctgctcagca tgggcagcaa    4620
tgaaaacatc cattctattc atttcagtgg acatgtgttc actgtacgaa aaaagagga    4680
gtataaaatg gcactgtaca atctctatcc aggtgttttt gagacagtgg aaatgttacc    4740
atccaaagct ggaatttggc gggtggaatg ccttattggc gagcatctac atgctgggat    4800
gagcacactt tttctggtgt acagcaataa gtgtcagact cccctgggaa tggcttctgg    4860
acacattaga gattttcaga ttacagcttc aggacaatat ggacagtggg ccccaaagct    4920
ggccagactt cattattccg gatcaatcaa tgcctggagc accaaggagc cttttcttg    4980
gatcaaggtg gatctgttgg caccaatgat tattcacggc atcaagaccc agggtgcccg    5040
tcagaagttc tccagcctct acatctctca gtttatcatc atgtatagtc ttgatgggaa    5100
gaagtggcag acttatcgag gaaattccac tggaacctta atggtcttct ttggcaatgt    5160
ggattcatct gggataaaac acaatatttt taaccctcca attattgctc gatacatccg    5220
tttgcaccca actcattata gcattcgcag cactcttcgc atggagttga tgggctgtga    5280
tttaaatagt tgcagcatgc cattgggaat ggagagtaaa gcaatatcag atgcacagat    5340
tactgcttca tcctacttta ccaatatgtt tgccacctgg tctccttcaa aagctcgact    5400
tcacctccaa gggaggagta atgcctggag acctcaggtg aataatccaa agagtggct    5460
gcaagtggac ttccagaaga cagtgaaagt cacaggagta actactcagg gagtaaaatc    5520
tctgcttacc agcatgtatg tgaaggagtt cctcatctcc agcagtcaag atggccatca    5580
gtggactctc ttttttcaga atggcaaagt aaaggttttt cagggaaatc aagactcctt    5640
cacacctgtg gtgaactctc tagacccacc gttactgact cgctaccttc gaattcaccc    5700
ccagagttgg gtgcaccaga ttgccctgag gatggaggtt ctgggctgcg aggcacagga    5760
cctctactag ccgcggtgaa gcttgatggg tggcatccct gtgaccccctc cccagtgcct    5820
ctcctggccc tggaagttgc cactccagtg cccaccagcc ttgtcctaat aaaattaagt    5880
tgcatcattt tgtctgacta ggtgtccttc tataatatta tgggggtggag ggggtggta    5940
tggagcaagg ggcaagttgg gaagacaacc tgtagggcct gcggggtcta ttgggaacca    6000
agctggagtg cagtggcaca atcttggctc actgcaatct ccgcctcctg ggttcaagcg    6060
attctcctgc ctcagcctcc cgagttgttg ggattccagg catgcatgac caggctcagc    6120
taattttttgt ttttttggta gagacgggg ttcaccatat tggccaggct ggtctccaac    6180
tcctaatctc aggtgatcta cccaccttgg cctcccaaat tgctgggatt acaggcgtga    6240
accactgctc ccttccctgt ccttctgatt ttaaaataac tataccagca ggaggacgtc    6300
cagacacagc ataggctacc tggccatgcc caaccggtgg acatttgag ttgcttgctt    6360
ggcactgtcc tctcatgcgt tgggtccact cagtagatgc ctgttttgtg gggatgtaag    6420
tctgcttgga ggaaggtgca gacatcgggt taggatggtt gtgatgctac ctgggcccca    6480
aagaaacatt tctgggtaag gtgtgcacac atctgtgtta ttagcagaaa tgctaactgc    6540
caattctttt cataggtctg acctatttgt tgatattttg ttctgttttg tccattgctt    6600
ctcttcgtca tatgctgctc ctccagaatc tagagactgg agtagaggga gggtgaaggg    6660
acaaagacaa aacttccctc tgcctgccca agcttccata gagagaatca aggcaatgaa    6720
atccaatcaa tatcacacac aagtttcatg tctggttctc ttgtgtgtac atgcaatgtg    6780
```

```
tgttttata  atatcttttc  ctactttggg  tgtaaggata  atatgagcct  tgagttcaga   6840
agcttttcgt  gttttggggg  ttctggtgca  tttaggcaga  gtattaaata  actttatcaa   6900
tattgtctat  ggtcatcagt  tgattcagat  ttttctacct  cttcttcagt  aaatattggt   6960
atattttggt  ctatactttc  atagaaagca  atctactgtc  cctagatttg  ataatgtatt   7020
ggtatcaagt  tatgtaagag  tctcctgtga  ttttgttaaa  ctgttctgtg  tcaaatgagt   7080
cttcggacct  cgcgggggcc  gcttaagcgg  tggttagggt  ttgtctgacg  cggggggagg   7140
gggaaggaac  gaaacactct  cattcggagg  cggctcgggg  tttggtcttg  gtggccacgg   7200
gcacgcagaa  gagcgccgcg  atcctcttaa  gcaccccccc  gccctccgtg  gaggcggggg   7260
tttggtcggc  gggtggtaac  tggcgggccg  ctgactcggg  cgggtcgcgc  gccccagagt   7320 gtgaccttt  cggtctgctc  gcagaccccc  gggcggcgcc  gccgcggcgg  cgacgggctc   7380
gctgggtcct  aggctccatg  gggaccgtat  acgtggacag  gctctggagc  atccgcacga   7440
ctgcggtgat  attaccggag  accttctgcg  ggacagccg  ggtcacgcgg  ctgacgcgga   7500
gcgtccgttg  ggcgacaaac  accaggacgg  ggcacaggta  cactatcttg  tcacccggag   7560
gcgcgaggga  ctgcaggagc  ttcagggagt  ggcgcagctg  cttcatcccc  gtggcccgtt   7620
gctcgcgttt  gctggcggtg  tccccggaag  aaatatattt  gcatgtcttt  agttctatga   7680
tgacacaaac  cccgcccagc  gtcttgtcat  tggcgaattc  gaacacgcag  atgcagtcgg   7740
ggcggcgcgg  tcccaggtcc  acttcgcata  ttaaggtgac  gcgtgtggcc  tcgaacaccg   7800
agcgaccctg  cagcgacccg  cttaaatggc  ttcgtacccc  tgccatcaac  acgcgtctgc   7860
gttcgaccag  gctgcgcgtt  ctcgcggcca  taacaaccga  cgtacggcgt  tgcgccctcg   7920
ccggcaacaa  aaagccacgg  aagtccgcct  ggagcagaaa  atgcccacgc  tactgcgggt   7980
ttatatagac  ggtccccacg  ggatggggaa  aaccaccacc  acgcaactgc  tggtggccct   8040
gggttcgcgc  gacgatatcg  tctacgtacc  cgagccgatg  acttactggc  gggtgttggg   8100
ggcttccgag  acaatcgcga  acatctacac  cacacaacac  cgcctcgacc  agggtgagat   8160
atcggccggg  gacgcggcgg  tggtaatgac  aagcgcccag  ataacaatgg  gcatgcctta   8220
tgccgtgacc  gacgccgttc  tggctcctca  tatcgggggg  gaggctggga  gctcacatgc   8280
cccgcccccg  gccctcaccc  tcatcttcga  ccgccatccc  atcgccgccc  tcctgtgcta   8340
cccggccgcg  cgatacccta  tgggcagcat  gaccccccag  gccgtgctgg  cgttcgtggc   8400
cctcatcccg  ccgaccttgc  ccggcacaaa  catcgtgttg  ggggcccttc  cggaggacag   8460
acacatcgac  cgcctggcca  aacgccagcg  ccccggcgag  cggcttgacc  tggctatgct   8520
ggccgcgatt  cgccgcgttt  atgggctgct  tgccaatacg  gtgcggtatc  tgcagggcgg   8580
cgggtcgtgg  cgggaggatt  ggggacagct  ttcgggggcg  gccgtgccgc  ccagggtgc   8640 cgagccccag  agcaacgcgg  gcccacgacc  ccatatcggg  gacacgttat  ttaccctgtt   8700
tcgggccccc  gagttgctgg  cccccaacgg  cgacctgtat  aacgtgtttg  cctgggcttt   8760
ggacgtcttg  gccaaacgcc  tccgtcccat  gcatgtcttt  atcctggatt  acgaccaatc   8820
gcccgccggc  tgccgggacg  ccctgctgca  acttacctcc  gggatggtcc  agacccacgt   8880
caccacccca  ggctccatac  cgacgatctg  cgacctggcg  cgcacgtttg  cccggggagat   8940 ggggaggct  aactgaaaca  cggaaggaga  caataccgga  aggaacccgc  gctatgacgg   9000
caataaaaag  acagaataaa  acgcacgggt  gttgggtcgt  ttgttcataa  acgcggggtt   9060
cggtcccagg  gctggcactc  tgtcgatacc  ccaccgagac  cccattggga  ccaatacgcc   9120
```

-continued

```
cgcgtttctt cctttccccc accccaaccc ccaagttcgg gtgaaggccc agggctcgca    9180
gccaacgtcg gggcggcaag ccctgccata gctcgagcag cttttgttcc ctttagtgag    9240
ggttaattgc gcgcttggcg taatcatggt catagctgtt tcctgtgtga aattgttatc    9300
cgctcacaat tccacacaac atacgagccg gaagcataaa gtgtaaagcc tggggtgcct    9360
aatgagtgag ctaactcaca ttaattgcgt tgcgctcact gcccgctttc cagtcgggaa    9420
acctgtcgtg ccagctgcat taatgaatcg gccaacgcgc ggggagaggc ggtttgcgta    9480
ttgggcgctc ttccgcttcc tcgctcactg actcgctgcg ctcggtcgtt cggctgcggc    9540
gagcggtatc agctcactca aaggcggtaa tacggttatc cacagaatca ggggataacg    9600
caggaaagaa catgtgagca aaaggccagc aaaaggccag gaaccgtaaa aaggccgcgt    9660
tgctggcgtt tttccatagg ctccgccccc ctgacgagca tcacaaaaat cgacgctcaa    9720
gtcagaggtg gcgaaacccg acaggactat aaagatacca ggcgtttccc cctggaagct    9780
ccctcgtgcg ctctcctgtt ccgaccctgc cgcttaccgg atacctgtcc gcctttctcc    9840
cttcgggaag cgtggcgctt tctcatagct cacgctgtag gtatctcagt tcggtgtagg    9900
tcgttcgctc caagctgggc tgtgtgcacg aaccccccgt tcagcccgac cgctgcgcct    9960
tatccggtaa ctatcgtctt gagtccaacc cggtaagaca cgacttatcg ccactggcag   10020
cagccactgg taacaggatt agcagagcga ggtatgtagg cggtgctaca gagttcttga   10080
agtggtggcc taactacggc tacactagaa ggacagtatt tggtatctgc gctctgctga   10140
agccagttac cttcggaaaa agagttggta gctcttgatc cggcaaacaa accaccgctg   10200
gtagcggtgg tttttttgtt tgcaagcagc agattacgcg cagaaaaaaa ggatctcaag   10260
aagatccttt gatcttttct acggggtctg acgctcagtg gaacgaaaac tcacgttaag   10320
ggattttggt catgagatta tcaaaaagga tcttcaccta gatcctttta aattaaaaat   10380
gaagttttaa atcaatctaa agtatatatg agtaaacttg gtctgacagt taccaatgct   10440
taatcagtga ggcacctatc tcagcgatct gtctatttcg ttcatccata gttgcctgac   10500
tccccgtcgt gtagataact acgatacggg agggcttacc atctggcccc agtgctgcaa   10560
tgataccgcg agacccacgc tcaccggctc cagatttatc agcaataaac cagccagccg   10620
gaagggccga gcgcagaagt ggtcctgcaa ctttatccgc ctccatccag tctattaatt   10680
gttgccggga agctagagta agtagttcgc cagttaatag tttgcgcaac gttgttgcca   10740
ttgctacagg catcgtggtg tcacgctcgt cgtttggtat ggcttcattc agctccggtt   10800
cccaacgatc aaggcgagtt acatgatccc ccatgttgtg caaaaaagcg gttagctcct   10860
tcggtcctcc gatcgttgtc agaagtaagt tggccgcagt gttatcactc atggttatgg   10920
cagcactgca taattctctt actgtcatgc catccgtaag atgcttttct gtgactggtg   10980
agtactcaac caagtcattc tgagaatagt gtatgcggcg accgagttgc tcttgcccgg   11040
cgtcaatacg ggataatacc gcgccacata gcagaacttt aaaagtgctc atcattggaa   11100
aacgttcttc ggggcgaaaa ctctcaagga tcttaccgct gttgagatcc agttcgatgt   11160
aacccactcg tgcacccaac tgatcttcag catcttttac tttcaccagc gtttctgggt   11220
gagcaaaaac aggaaggcaa aatgccgcaa aaaagggaat aagggcgaca cggaaatgtt   11280
gaatactcat actcttcctt tttcaatatt attgaagcat ttatcagggt tattgtctca   11340
tgagcggata catatttgaa tgtatttaga aaaataaaca ataggggtt ccgcgcacat   11400
ttccccgaaa agtgccac                                                 11418
```

<210> SEQ ID NO 14
<211> LENGTH: 7755
<212> TYPE: DNA
<213> ORGANISM: Artificial Sequence
<220> FEATURE:
<223> OTHER INFORMATION: synthetic construct

<400> SEQUENCE: 14

| | | | | | |
|---|---|---|---|---|---|
| ctgacgcgcc | ctgtagcggc | gcattaagcg | cggcgggtgt | ggtggttacg | cgcagcgtga | 60 |
| ccgctacact | tgccagcgcc | ctagcgcccg | ctcctttcgc | tttcttccct | tcctttctcg | 120 |
| ccacgttcgc | cggctttccc | cgtcaagctc | taaatcgggg | gctcccttta | gggttccgat | 180 |
| ttagtgcttt | acggcacctc | gaccccaaaa | aacttgatta | gggtgatggt | tcacgtagtg | 240 |
| ggccatcgcc | ctgatagacg | gttttcgcc | ctttgacgtt | ggagtccacg | ttctttaata | 300 |
| gtggactctt | gttccaaact | ggaacaacac | tcaaccctat | ctcggtctat | tcttttgatt | 360 |
| tataagggat | tttgccgatt | tcggcctatt | ggttaaaaaa | tgagctgatt | taacaaaaat | 420 |
| ttaacgcgaa | ttttaacaaa | atattaacgc | ttacaatttc | cattcgccat | tcaggctgcg | 480 |
| caactgttgg | gaagggcgat | cggtgcgggc | ctcttcgcta | ttacgccagc | tggcgaaagg | 540 |
| gggatgtgct | gcaaggcgat | taagttgggt | aacgccaggg | ttttcccagt | cacgacgttg | 600 |
| taaaacgacg | gccagtgagc | gcgcgtaata | cgactcacta | tagggcgaat | tggagctcca | 660 |
| ccgcggtggc | ggccgctcta | gaactagtgg | atccccgggc | tgcaggaatt | cgatatcaa | 720 |
| gcttatcgat | accgtcgacc | tcgaggcttc | caggtcgtag | gtagattcaa | agattttctg | 780 |
| attggcaatt | ggttgaaaga | gttaagttat | tgtgtaaaga | cttagaatca | atagagagga | 840 |
| acatcggggt | taagataagg | ggttgtgaag | accaaggttc | tgtcatgcag | atgaagcctc | 900 |
| caggtagcag | gcttcagaga | gaatagattg | taaatgtttc | ttatcagact | aaagagtct | 960 |
| gttctatcag | tctgaaggtc | tgtgttgatg | ttaatgctgg | tcagattttt | ctgaattcca | 1020 |
| aaagggaggc | gggtataata | aggcatattt | gatccccact | ttcccatcat | ggcctgaacg | 1080 |
| tttttcaggt | taactttgga | aggcccttg | ccgaaaggag | gggggattag | aattttattt | 1140 |
| tgggtttaca | ggatggtaat | actctgttcc | caccctccta | actagtatct | ttattaaacc | 1200 |
| ttccacaaat | tatcctaatt | tccatgtttt | ctgttccttg | ctggatccct | tgtttcatac | 1260 |
| agtaattggt | gctagaagaa | accccaggaa | acagattttc | aaaatgcaat | tctaaggtta | 1320 |
| tgttgctaat | atattcaaga | aacacagaga | taacatattt | gccaaggaag | aaaatgagca | 1380 |
| gttagggaat | ccatgacatg | tgttagtatt | atagtttctc | agattatcac | cagtgatact | 1440 |
| atgggaggtc | ttctttggca | atgtggattc | atctgggata | aaacacaata | ttttttaaccc | 1500 |
| tccaattatt | gctcgataca | tccgtttgca | cccaactcat | tatagcattc | gcagcactct | 1560 |
| tcgcatggag | ttgatgggct | gtgatttaaa | tagttcagc | atgccattgg | gaatggagag | 1620 |
| taaagcaata | tcagatgcac | agattactgc | ttcatcctac | tttaccaata | tgtttgccac | 1680 |
| ctggtctcct | tcaaaagctc | gacttcacct | ccaaggagg | agtaatgcct | ggagacctca | 1740 |
| ggtgaataat | ccaaaagagt | ggctgcaagt | ggacttccag | aagacagtga | aagtcacagg | 1800 |
| agtaactact | cagggagtaa | aatctctgct | taccagcatg | tatgtgaagg | agttcctcat | 1860 |
| ctccagcagt | caagatggcc | atcagtggac | tctcttttt | cagaatggca | aagtaaaggt | 1920 |
| ttttcaggga | aatcaagact | ccttcacacc | tgtggtgaac | tctctagacc | caccgttact | 1980 |
| gactcgctac | cttcgaattc | accccagag | ttgggtgcac | cagattgccc | tgaggatgga | 2040 |
| ggttctgggc | tgcgaggcac | aggacctcta | ctagccgcgg | tgaagcttga | tgggtggcat | 2100 |

-continued

```
ccctgtgacc cctccccagt gcctctcctg gccctggaag ttgccactcc agtgcccacc    2160
agccttgtcc taataaaatt aagttgcatc attttgtctg actaggtgtc cttctataat    2220
attatggggt ggagggggt ggtatggagc aaggggcaag ttgggaagac aacctgtagg    2280
gcctgcgggg tctattggga accaagctgg agtgcagtgg cacaatcttg gctcactgca    2340
atctccgcct cctgggttca agcgattctc ctgcctcagc ctcccgagtt gttgggattc    2400
caggcatgca tgaccaggct cagctaattt ttgttttttt ggtagagacg gggtttcacc    2460
atattggcca ggctggtctc caactcctaa tctcaggtga tctacccacc ttggcctccc    2520
aaattgctgg gattacaggc gtgaaccact gctcccttcc ctgtccttct gattttaaaa    2580
taactatacc agcaggagga cgtccagaca cagcataggc tacctggcca tgcccaaccg    2640
gtgggacatt tgagttgctt gcttggcact gtcctctcat gcgttgggtc cactcagtag    2700
atgcctgttg gagattaaat gacagtggca tttagtcact gtggcaacaa acgtagcatt    2760
acctgattgt agagtggtct gtcttcttac agccctagag ggcatacaca tggaaaaaga    2820
aatgaaatgt tatgaatata tacaaaataa gaacactgat gaacatacat ggaaaatcag    2880
gatgcatgca tagagctttt gaggaatact ccgtatcctg tggttgtagg cagatacgac    2940 ttagggggctg agcataagtt gcagagctgc agtgacaatt aaatgcttaa ctccaccaga    3000
tctattatgc tgtggtaaga gtaccggtgg gaaggagtga aactctgagg cctgagatgg    3060
aggcatttag gcagacatgg atgaggctga gaattgcaaa cctccaaatt ccctgaacc    3120 tcctttgcct gaggaggcaa ccactcccca gtctctgaag cagtcatccc tcttttgtgt    3180
aaaagccttt cagtggctat aactgagata ggtgcctcac aaaccagtga ctattctcct    3240
tagagaccct gtttggacac tacgaaagcc aggcgagtca cagaaaatga cagcagatca    3300
caaatttaat caggtggtga tgccaaaaaa caattgcaat tccagatatc atatctctgt    3360
tgaagcaaat ttacacagcc ccaggcacct gatatgaag tattgaccta aatgagtctt    3420
cggacctcgc gggggccgct taagcggtgg ttagggtttg tctgacgcgg ggggagggg    3480 aaggaacgaa acactctcat tcggaggcgg ctcggggttt ggtcttggtg ccacgggca    3540 cgcagaagag cgccgcgatc ctcttaagca cccccccgcc ctccgtggag gcggggttt    3600 ggtcggcggg tggtaactgg cgggccgctg actcgggcgg gtcgcgcgcc ccagagtgtg    3660
accttttcgg tctgctcgca gaccccgggg cggcgccgcc gcggcggcga cgggctcgct    3720
gggtcctagg ctccatgggg accgtatacg tggacaggct ctggagcatc cgcacgactg    3780
cggtgatatt accggagacc ttctgcggga cgagccgggt cacgcggctg acgcggagcg    3840
tccgttgggc gacaaacacc aggacggggc acaggtacac tatcttgtca cccggaggcg    3900
cgagggactg caggagcttc agggagtggc gcagctgctt catccccgtg gcccgttgct    3960 cgcgttttgct ggcggtgtcc ccggaagaaa tatatttgca tgtctttagt tctatgatga    4020
cacaaacccc gcccagcgtc ttgtcattgg cgaattcgaa cacgcagatg cagtcggggc    4080
ggcgcggtcc caggtccact tcgcatatta aggtgacgcg tgtggcctcg aacaccgagc    4140
gaccctgcag cgacccgctt aaatggcttc gtacccctgc catcaacacg cgtctgcgtt    4200
cgaccaggct gcgcgttctc gcggccataa caaccgacgt acggcgttgc ccctcgccg    4260 gcaacaaaaa gccacggaag tccgcctgga gcagaaatg cccacgctac tgcgggttta    4320
tatagacggt ccccacggga tggggaaaac caccaccacg caactgctgg tggccctggg    4380
ttcgcgcgac gatatcgtct acgtacccga gccgatgact tactggcggg tgttgggggc    4440
ttccgagaca atcgcgaaca tctacaccac acaacaccgc ctcgaccagg gtgagatatc    4500
```

```
ggccggggac gcggcggtgg taatgacaag cgcccagata acaatgggca tgccttatgc      4560
cgtgaccgac gccgttctgg ctcctcatat cgggggggag gctgggagct cacatgcccc      4620
gcccccggcc ctcaccctca tcttcgaccg ccatcccatc gccgccctcc tgtgctaccc      4680
ggccgcgcga tacctatgg gcagcatgac cccccaggcc gtgctggcgt tcgtggccct       4740
catcccgccg accttgcccg gcacaaacat cgtgttgggg gccttccgg aggacagaca       4800 catcgaccgc ctggccaaac gccagcgccc ggcgagcgg cttgacctgg ctatgctggc       4860
cgcgattcgc cgcgtttatg ggctgcttgc caatacggtg cggtatctgc agggcggcgg      4920
gtcgtggcgg gaggattggg gacagctttc ggggcggcc gtgccgcccc agggtgccga       4980
gccccagagc aacgcgggcc cacgacccca tatcggggac acgttattta ccctgtttcg      5040
ggcccccgag ttgctggccc ccaacggcga cctgtataac gtgtttgcct gggctttgga      5100
cgtcttggcc aaacgcctcc gtcccatgca tgtctttatc ctggattacg accaatcgcc      5160
cgccggctgc cgggacgccc tgctgcaact tacctccggg atggtccaga cccacgtcac      5220
caccccaggc tccataccga cgatctgcga cctggcgcgc acgtttgccc gggagatggg      5280
ggaggctaac tgaaacacgg aaggagacaa taccggaagg aacccgcgct atgacggcaa      5340 taaaagaca gaataaaacg cacgggtgtt gggtcgtttg ttcataaacg cggggttcgg       5400
tcccagggct ggcactctgt cgatacccca ccgagacccc attgggacca atacgcccgc      5460
gtttcttcct tttccccacc ccaaccccca agttcgggtg aaggcccagg gctcgcagcc      5520
aacgtcgggg cggcaagccc tgccataggg tacccagctt ttgttcccct tagtgagggt       5580
taattgcgcg cttggcgtaa tcatggtcat agctgtttcc tgtgtgaaat tgttatccgc      5640
tcacaattcc acacaacata cgagccgaa gcataaagtg taaagcctgg ggtgcctaat       5700
gagtgagcta actcacatta attgcgttgc gctcactgcc cgctttccag tcgggaaacc      5760
tgtcgtgcca gctgcattaa tgaatcggcc aacgcgcggg gagaggcggt ttgcgtattg      5820
ggcgctcttc cgcttcctcg ctcactgact cgctgcgctc ggtcgttcgg ctgcggcgag      5880
cggtatcagc tcactcaaag gcggtaatac ggttatccac agaatcaggg gataacgcag      5940
gaaagaacat gtgagcaaaa ggccagcaaa aggccaggaa ccgtaaaaag gccgcgttgc      6000
tggcgttttt ccataggctc cgcccccctg acgagcatca caaaaatcga cgctcaagtc      6060
agaggtggcg aaacccgaca ggactataaa gataccaggc gtttccccct ggaagctccc      6120
tcgtgcgctc tcctgttccg accctgccgc ttaccggata cctgtccgcc tttctccctt      6180
cgggaagcgt ggcgctttct catagctcac gctgtaggta tctcagttcg gtgtaggtcg      6240
ttcgctccaa gctgggctgt gtgcacgaac cccccgttca gcccgaccgc tgcgccttat      6300
ccggtaacta tcgtcttgag tccaacccgg taagacacga cttatcgcca ctggcagcag      6360
ccactggtaa caggattagc agagcgaggt atgtaggcgg tgctacagag ttcttgaagt      6420
ggtggcctaa ctacggctac actagaagga cagtatttgg tatctgcgct ctgctgaagc      6480
cagttacctt cggaaaaaga gttggtagct cttgatccgg caaacaaacc accgctggta      6540
gcggtggttt ttttgtttgc aagcagcaga ttacgcgcag aaaaaaagga tctcaagaag      6600
atcctttgat cttttctacg ggtctgacg ctcagtggaa cgaaaactca cgttaaggga       6660
ttttggtcat gagattatca aaaggatct tcacctagat ccttttaaat taaaaatgaa       6720
gttttaaatc aatctaaagt atatatgagt aaacttggtc tgacagttac caatgcttaa      6780
tcagtgaggc acctatctca gcgatctgtc tatttcgttc atccatagtt gcctgactcc      6840
```

| | | |
|---|---|---|
| ccgtcgtgta gataactacg atacgggagg gcttaccatc tggccccagt gctgcaatga | 6900 | |
| taccgcgaga cccacgctca ccggctccag atttatcagc aataaaccag ccagccggaa | 6960 | |
| gggccgagcg cagaagtggt cctgcaactt tatccgcctc catccagtct attaattgtt | 7020 | |
| gccgggaagc tagagtaagt agttcgccag ttaatagttt gcgcaacgtt gttgccattg | 7080 | |
| ctacaggcat cgtggtgtca cgctcgtcgt ttggtatggc ttcattcagc tccggttccc | 7140 | |
| aacgatcaag gcgagttaca tgatccccca tgttgtgcaa aaaagcggtt agctccttcg | 7200 | |
| gtcctccgat cgttgtcaga agtaagttgg ccgcagtgtt atcactcatg gttatggcag | 7260 | |
| cactgcataa ttctcttact gtcatgccat ccgtaagatg cttttctgtg actggtgagt | 7320 | |
| actcaaccaa gtcattctga atagtgta tgcggcgacc gagttgctct tgcccggcgt | 7380 | |
| caatacggga taataccgcg ccacatagca gaactttaaa agtgctcatc attggaaaac | 7440 | |
| gttcttcggg gcgaaaactc tcaaggatct taccgctgtt gagatccagt tcgatgtaac | 7500 | |
| ccactcgtgc acccaactga tcttcagcat cttttacttt caccagcgtt tctgggtgag | 7560 | |
| caaaaacagg aaggcaaaat gccgcaaaaa agggaataag ggcgacacgg aaatgttgaa | 7620 | |
| tactcatact cttccttttt caatattatt gaagcattta tcagggttat tgtctcatga | 7680 | |
| gcggatacat atttgaatgt atttagaaaa ataaacaaat aggggttccg cgcacatttc | 7740 | |
| cccgaaaagt gccac | 7755 | |

<210> SEQ ID NO 15
<211> LENGTH: 11359
<212> TYPE: DNA
<213> ORGANISM: Artificial Sequence
<220> FEATURE:
<223> OTHER INFORMATION: synthetic construct

<400> SEQUENCE: 15

| | | |
|---|---|---|
| ctgacgcgcc ctgtagcggc gcattaagcg cggcgggtgt ggtggttacg cgcagcgtga | 60 | |
| ccgctacact tgccagcgcc ctagcgcccg ctcctttcgc tttcttccct tcctttctcg | 120 | |
| ccacgttcgc cggctttccc cgtcaagctc taaatcgggg gctcccttta gggttccgat | 180 | |
| ttagtgcttt acggcacctc gaccccaaaa aacttgatta gggtgatggt tcacgtagtg | 240 | |
| ggccatcgcc ctgatagacg gtttttcgcc ctttgacgtt ggagtccacg ttctttaata | 300 | |
| gtggactctt gttccaaact ggaacaacac tcaaccctat ctcggtctat tcttttgatt | 360 | |
| tataagggat tttgccgatt tcggcctatt ggttaaaaaa tgagctgatt taacaaaaat | 420 | |
| ttaacgcgaa ttttaacaaa atattaacgc ttacaatttc cattcgccat tcaggctgcg | 480 | |
| caactgttgg gaagggcgat cggtgcgggc ctcttcgcta ttacgccagc tggcgaaagg | 540 | |
| gggatgtgct gcaaggcgat taagttgggt aacgccaggg ttttcccagt cacgacgttg | 600 | |
| taaaacgacg gccagtgagc gcgcgtaata cgactcacta tagggcgaat tggagctcca | 660 | |
| ccgcggtggc ggccgctcta gaactagtgg atccccccggg ctgcaggaat tcgatatcaa | 720 | |
| gcttatcgat accgtcgacc tcgagaaagc agacttatgc ccctactgct ctcagaagtg | 780 | |
| aatgggttaa gtttagcagc ctccctttg ctacttcagt tcttcctgtg gctgcttccc | 840 | |
| actgataaaa aggaagcaat cctatcggtt actgcttagt gctgagcaca tccagtgggt | 900 | |
| aaagttcctt aaaatgctct gcaaagaaat tgggactttt cattaaatca gaaattttac | 960 | |
| ttttttcccc tcctgggagc taaagatatt ttagagaaga attaacctt tgcttctcca | 1020 | |
| gttgaacatt tgtagcaata agtcatgcaa atagagctct ccacctgctt cttttctgtgc | 1080 | |
| cttttgcgat tctgctttag tgccaccaga agatactacc tgggtgcagt ggaactgtca | 1140 | |

```
tgggactata tgcaaagtga tctcggtgag ctgcctgtgg acgcaaggta aaggcatgtc    1200
ctgtagggtc tgatcggggc caggattgtg gggatgtaaa tctgcttgga ggaaggtgca    1260
gacatcgggt taggatggtt gtgatgctac ctgggcccca agaaacatt tctgggtaag     1320 gtgtgcacac atctgtgtta ttagcagaaa tgctaactgc caattctttt cataggtctg    1380
acctatttgt tgatattttg ttctgttttg tccattgctt ctcttcgtca tatgctgctc    1440
ctccaagatt tcctcctaga gtgccaaaat cttttccatt caacacctca gtcgtgtaca    1500
aaaagactct gtttgtagaa ttcacggatc accttttcaa catcgctaag ccaaggccac    1560
cctggatggg tctgctaggt cctaccatcc aggctgaggt ttatgataca gtggtcatta    1620
cacttaagaa catggcttcc catcctgtca gtcttcatgc tgttggtgta tcctactgga    1680
aagcttctga gggagctgaa tatgatgatc agaccagtca aagggagaaa gaagatgata    1740 aagtctttccc tggtggaagc catacatatg tctggcaggt cctgaaagag aatggtccaa    1800
tggcctctga cccactgtgc cttacctact catatctttc tcatgtggac ctggtaaaag    1860
acttgaattc aggcctcatt ggagccctac tagtatgtag agaagggagt ctggccaagg    1920
aaaagacaca gaccttgcac aaatttatac tacttttttgc tgtatttgat gaagggaaaa    1980
gttggcactc agaaacaaag aactccttga tgcaggatag ggatgctgca tctgctcggg    2040
cctggcctaa aatgcacaca gtcaatggtt atgtaaacag gtctctgcca ggtctgattg    2100
gatgccacag gaaatcagtc tattggcatg tgattggaat gggcaccact cctgaagtgc    2160
actcaatatt cctcgaaggt cacacatttc ttgtgaggaa ccatcgccag gcgtccttgg    2220
aaatctcgcc aataactttc cttactgctc aaacactctt gatggacctt ggacagtttc    2280
tactgttttg tcatatctct tcccaccaac atgatggcat ggaagcttat gtcaaagtag    2340
acagctgtcc agaggaaccc caactacgaa tgaaaaataa tgaagaagcg aagactatg     2400 atgatgatct tactgattct gaaatggatg tggtcaggtt tgatgatgac aactctcctt    2460
cctttatcca aattcgctca gttgccaaga agcatcctaa aacttgggta cattacattg    2520
ctgctgaaga ggaggactgg gactatgctc ccttagtcct cgcccccgat gacagaagtt    2580
ataaaagtca atatttgaac aatggccctc agcggattgg taggaagtac aaaaaagtcc    2640
gatttatggc atacacagat gaaacccttta agactcgtga agctattcag catgaatcag    2700
gaatcttggg accttttactt tatggggaag ttggagacac actgttgatt atatttaaga    2760
atcaagcaag cagaccatat aacatctacc ctcacggaat cactgatgtc cgtcctttgt    2820
attcaaggag attaccaaaa ggtgtaaaac atttgaagga tttttccaatt ctgccaggag    2880 aaatattcaa atataaatgg acagtgactg tagaagatgg gccaactaaa tcagatcctc    2940
ggtgcctgac ccgctattac tctagtttcg ttaatatgga gagagatcta gcttcaggac    3000
tcattggccc tctcctcatc tgctacaaag aatctgtaga tcaaagagga aaccagataa    3060
tgtcagacaa gaggaatgtc atcctgttt ctgtattttga tgagaaccga agctggtacc     3120
tcacagagaa tatacaacgc tttctcccca atccagctgg agtgcagctt gaggatccag    3180
agttccaagc ctccaacatc atgcacagca tcaatggcta tgtttttgat agtttgcagt    3240
tgtcagtttg tttgcatgag gtggcatact ggtacattct aagcattgga gcacagactg    3300
acttcctttc tgtcttcttc tctggatata ccttcaaaca caaatggtc tatgaagaca     3360 cactcaccct attcccattc tcaggagaaa ctgtcttcat gtcgatggaa aacccaggtc    3420
tatggattct ggggtgccac aactcagact ttcggaacag aggcatgacc gccttactga    3480
```

-continued

```
aggtttctag ttgtgacaag aacactggtg attattacga ggacagttat gaagatattt    3540
cagcatactt gctgagtaaa aacaatgcca ttgaaccaag aagcttctcc caaaacccac    3600
cagtcttgaa acgccatcaa cgggaaataa ctcgtactac tcttcagtca gatcaagagg    3660
aaattgacta tgatgatacc atatcagttg aaatgaagaa ggaagatttt gacatttatg    3720
atgaggatga aaatcagagc ccccgcagct ttcaaaagaa aacacgacac tattttattg    3780
ctgcagtgga gaggctctgg gattatggga tgagtagctc cccacatgtt ctaagaaaca    3840
gggctcagag tggcagtgtc cctcagttca agaaagttgt tttccaggaa tttactgatg    3900
gctcctttac tcagcccctta taccgtggag aactaaatga catttggga ctcctggggc    3960 catatataag agcagaagtt gaagataata tcatggtaac tttcagaaat caggcctctc    4020
gtccctattc cttctattct agccttattt cttatgagga agatcagagg caaggagcag    4080
aacctagaaa aaactttgtc aagcctaatg aaaccaaaac ttacttttgg aaagtgcaac    4140
atcatatggc acccactaaa gatgagtttg actgcaaagc ctgggcttat ttctctgatg    4200
ttgacctgga aaaagatgtg cactcaggcc tgattggacc ccttctggtc tgccacacta    4260
acacactgaa ccctgctcat gggagacaag tgacagtaca ggaatttgct ctgttttttca    4320 ccatctttga tgagaccaaa agctggtact tcactgaaaa tatggaaaga aactgcaggg    4380
ctccctgcaa tatccagatg aagatccca cttttaaaga gaattatcgc ttccatgcaa    4440
tcaatggcta cataatggat acactacctg gcttagtaat ggctcaggat caaaggattc    4500
gatggtatct gctcagcatg ggcagcaatg aaaacatcca ttctattcat ttcagtggac    4560
atgtgttcac tgtacgaaaa aaagaggagt ataaaatggc actgtacaat ctctatccag    4620 gtgttttttga cagtggaaa atgttaccat ccaaagctgg aatttggcgg gtggaatgcc    4680
ttattggcga gcatctacat gctgggatga gcacactttt tctggtgtac agcaataagt    4740
gtcagactcc cctgggaatg gcttctggac acattagaga ttttcagatt acagcttcag    4800
gacaatatgg acagtgggcc ccaaagctgg ccagacttca ttattccgga tcaatcaatg    4860
cctggagcac caaggagccc ttttcttgga tcaaggtgga tctgttggca ccaatgatta    4920
ttcacggcat caagacccag ggtgcccgtc agaagttctc cagcctctac atctctcagt    4980
ttatcatcat gtatagtctt gatgggaaga agtggcagac ttatcgagga aattccactg    5040
gaaccttaat ggtcttcttt ggcaatgtgg attcatctgg gataaaacac aatatttttta    5100 accctccaat tattgctcga tacatccgtt tgcacccaac tcattatagc attcgcagca    5160
ctcttcgcat ggagttgatg ggctgtgatt taaatagttg cagcatgcca ttgggaatgg    5220
agagtaaagc aatatcagat gcacagatta ctgcttcatc ctactttacc aatatgtttg    5280
ccacctggtc tccttcaaaa gctcgacttc acctccaagg gaggagtaat gcctggagac    5340
ctcaggtgaa taatccaaaa gagtggctgc aagtggactt ccagaagaca gtgaaagtca    5400
caggagtaac tactcaggga gtaaaatctc tgcttaccag catgtatgtg aaggagttcc    5460
tcatctccag cagtcaagat ggccatcagt ggactctctt ttttcagaat ggcaaagtaa    5520 aggttttca gggaaatcaa gactccttca cacctgtggt gaactctcta gacccaccgt    5580
tactgactcg ctaccttcga attcaccccc agagttgggt gcaccagatt gccctgagga    5640
tggaggttct gggctgcgag gcacaggacc tctactagcc gcggtgaagc ttgatgggtg    5700
gcatccctgt gacccctccc cagtgcctct cctggccctg gaagttgcca ctccagtgcc    5760
caccagcctt gtcctaataa aattaagttg catcattttg tctgactagg tgtccttcta    5820
taatattatg gggtggaggg gggtggtatg gagcaagggg caagttggga agacaacctg    5880
```

```
tagggcctgc ggggtctatt gggaaccaag ctggagtgca gtggcacaat cttggctcac    5940
tgcaatctcc gcctcctggg ttcaagcgat tctcctgcct cagcctcccg agttgttggg    6000
attccaggca tgcatgacca ggctcagcta atttttgttt ttttggtaga cacggggttt    6060
caccatattg gccaggctgg tctccaactc ctaatctcag gtgatctacc caccttggcc    6120
tcccaaattg ctgggattac aggcgtgaac cactgctccc ttccctgtcc ttctgatttt    6180
aaaataacta taccagcagg aggacgtcca gacacagcat aggctacctg gccatgccca    6240
accggtggga catttgagtt gcttgcttgg cactgtcctc tcatgcgttg ggtccactca    6300
gtagatgcct gttagggaca aagacaaaac ttccctctgc ctgcccaagc ttccatagag    6360
agaatcaagg caatgaaatc caatcaatat cacacacaag tttcatgtct ggttctcttg    6420
tgtgtacatg caatgtgtgt ttttataata tcttttccta ctttgggtgt aaggataata    6480
tgagccttga gttcagaagc ttttcgtgtt ttgggggttc tggtgcattt aggcagagta    6540
ttaaataact ttatcaatat tgtctatggt catcagttga ttcagatttt tctacctctt    6600
cttcagtaaa tattggtata ttttggtcta actttcata gaaagcaatc tactgtccct    6660
agatttgata atgtattggt atcaagttat gtaagagtct cctgtgattt tgttaaactg    6720
ttctgtgtct gtagttatat tttcttttc attccttatg ttgtatatgt tctcttcctc    6780
tcttttaaaa ataatatttc caggagtttt cttgatttta ttggtcttgt caagaatttt    6840
cttttggttt gatttatcaa tctcttttttt cttctgttg catcagtttc tgcttctact    6900
ttcattgatt tattccttcc ttctaatttc ctttggttca ttttgttgtt agattttgc    6960 ttcttgagtt gaatgctgaa atcatttatt ttatttttt gtcttcttta aataaatgag    7020
tcttcggacc tcgcggggc cgcttaagcg gtggttaggg tttgtctgac gcgggggag    7080 ggggaaggaa cgaaacactc tcattcggag gcggctcggg gtttggtctt ggtggccacg    7140
ggcacgcaga agagcgccgc gatcctctta agcaccccc cgccctccgt ggaggcgggg    7200
gtttggtcgg cgggtggtaa ctggcgggcc gctgactcgg gcgggtcgcg cgccccagag    7260
tgtgaccttt tcggtctgct cgcagacccc cgggcggcgc cgccgcgcg gcgacgggct    7320 cgctgggtcc taggctccat ggggaccgta tacgtggaca ggctctggag catccgcacg    7380
actgcggtga tattaccgga gaccttctgc gggacgagcc gggtcacgcg gctgacgcgg    7440
agcgtccgtt gggcgacaaa caccaggacg gggcacaggt acactatctt gtcacccgga    7500
ggcgcgaggg actgcaggag cttcaggag tggcgcagct gcttcatccc cgtggcccgt    7560
tgctcgcgtt tgctggcggt gtccccggaa gaaatatatt tgcatgtctt tagttctatg    7620
atgacacaaa ccccgcccag cgtcttgtca ttggcgaatt cgaacacgca gatgcagtcg    7680
gggcggcgcg gtcccaggtc cacttcgcat attaaggtga cgcgtgtggc ctcgaacacc    7740
gagcgaccct gcagcgaccc gcttaaatgg cttcgtaccc ctgccatcaa cacgcgtctg    7800
cgttcgacca ggctgcgcgt tctcgcggcc ataacaaccg acgtacggcg ttgcgccctc    7860
gccggcaaca aaaagccacg gaagtccgcc tggagcagaa aatgcccacg ctactgcggg    7920
tttatataga cggtccccac gggatgggga aaaccaccac cacgcaactg ctggtggccc    7980
tgggttcgcg cgacgatatc gtctacgtac ccgagccgat gacttactgg cgggtgttgg    8040
gggcttccga gacaatcgcg aacatctaca ccacacaaca ccgcctcgac cagggtgaga    8100
tatcggccgg ggacgcggcg gtggtaatga caagcgccca gataacaatg ggcatgcctt    8160
atgccgtgac cgacgccgtt ctggctcctc atatcggggg ggaggctggg agctcacatg    8220
```

```
ccccgccccc ggccctcacc ctcatcttcg accgccatcc catcgccgcc ctcctgtgct   8280
acccggccgc gcgataccct tatgggcagca tgaccccca ggccgtgctg gcgttcgtgg    8340
ccctcatccc gccgaccttg cccggcacaa acatcgtgtt gggggcccctt ccggaggaca   8400
gacacatcga ccgcctggcc aaacgccagc gccccggcga gcggcttgac ctggctatgc   8460
tggccgcgat tcgccgcgtt tatgggctgc ttgccaatac ggtgcggtat ctgcagggcg   8520
gcgggtcgtg gcgggaggat tggggacagc tttcggggggc ggccgtgccg ccccagggtg   8580
ccgagcccca gagcaacgcg ggcccacgac cccatatcgg ggacacgtta tttaccctgt   8640
ttcgggcccc cgagttgctg gcccccaacg gcgacctgta taacgtgttt gcctgggctt   8700
tggacgtctt ggccaaacgc ctccgtccca tgcatgtctt tatcctggat tacgaccaat   8760
cgcccgccgg ctgccgggac gccctgctgc aacttacctc cgggatggtc cagcccacg   8820
tcaccacccc aggctccata ccgacgatct gcgacctggc gcgcacgttt gcccgggaga   8880
tgggggaggc taactgaaac acggaaggag acaataccgg aaggaacccg cgctatgacg   8940
gcaataaaaa gacagaataa aacgcacggg tgttgggtcg tttgttcata aacgcggggt   9000
tcggtcccag ggctggcact ctgtcgatac cccaccgaga ccccattggg accaatacgc   9060
ccgcgttct tccttttccc caccccaacc cccaagttcg ggtgaaggcc cagggctcgc   9120
agccaacgtc ggggcggcaa gccctgccat agctcgagca gcttttgttc cctttagtga   9180
gggttaattg cgcgcttggc gtaatcatgg tcatagctgt ttcctgtgtg aaattgttat   9240
ccgctcacaa ttccacacaa catacgagcc ggaagcataa agtgtaaagc ctggggtgcc   9300
taatgagtga gctaactcac attaattgcg ttgcgctcac tgcccgcttt ccagtcggga   9360
aacctgtcgt gccagctgca ttaatgaatc ggccaacgcg cggggagagg cggtttgcgt   9420
attgggcgct cttccgcttc ctcgctcact gactcgctgc gctcggtcgt tcggctgcgg   9480
cgagcggtat cagctcactc aaaggcggta atacggttat ccacagaatc aggggataac   9540
gcaggaaaga acatgtgagc aaaaggccag caaaaggcca ggaaccgtaa aaaggccgcg   9600
ttgctggcgt ttttccatag gctccgcccc cctgacgagc atcacaaaaa tcgacgctca   9660
agtcagaggt ggcgaaaccc gacaggacta taaagatacc aggcgtttcc ccctggaagc   9720
tccctcgtgc gctctcctgt tccgaccctg ccgcttaccg gatacctgtc cgcctttctc   9780
ccttcgggaa gcgtggcgct ttctcatagc tcacgctgta ggtatctcag ttcggtgtag   9840
gtcgttcgct ccaagctggg ctgtgtgcac gaaccccccg ttcagcccga ccgctgcgcc   9900
ttatccggta actatcgtct tgagtccaac ccggtaagac acgacttatc gccactggca   9960
gcagccactg gtaacaggat tagcagagcg aggtatgtag gcggtgctac agagttcttg  10020
aagtggtggc ctaactacgg ctacactaga aggacagtat ttggtatctg cgctctgctg  10080
aagccagtta ccttcggaaa aagagttggt agctcttgat ccggcaaaca aaccaccgct  10140
ggtagcggtg gtttttttgt ttgcaagcag cagattacgc gcagaaaaaa aggatctcaa  10200
gaagatcctt tgatcttttc tacggggtct gacgctcagt ggaacgaaaa ctcacgttaa  10260
gggattttgg tcatgagatt atcaaaaagg atcttcacct agatcctttt aaattaaaaa  10320
tgaagtttta aatcaatcta agtatatat gagtaaactt ggtctgacag ttaccaatgc  10380
ttaatcagtg aggcacctat ctcagcgatc tgtctatttc gttcatccat agttgcctga  10440
ctccccgtcg tgtagataac tacgatacgg gagggcttac catctggccc cagtgctgca  10500
atgataccgc gagacccacg ctcaccggct ccagatttat cagcaataaa ccagccagcc  10560
ggaagggccg agcgcagaag tggtcctgca actttatccg cctccatcca gtctattaat  10620
```

-continued

```
tgttgccggg aagctagagt aagtagttcg ccagttaata gtttgcgcaa cgttgttgcc    10680
attgctacag gcatcgtggt gtcacgctcg tcgtttggta tggcttcatt cagctccggt    10740
tcccaacgat caaggcgagt tacatgatcc cccatgttgt gcaaaaaagc ggttagctcc    10800
ttcggtcctc cgatcgttgt cagaagtaag ttggccgcag tgttatcact catggttatg    10860
gcagcactgc ataattctct tactgtcatg ccatccgtaa gatgcttttc tgtgactggt    10920
gagtactcaa ccaagtcatt ctgagaatag tgtatgcggc gaccgagttg ctcttgcccg    10980
gcgtcaatac gggataatac cgcgccacat agcagaactt taaaagtgct catcattgga    11040
aaacgttctt cggggcgaaa actctcaagg atcttaccgc tgttgagatc cagttcgatg    11100
taacccactc gtgcacccaa ctgatcttca gcatctttta ctttcaccag cgtttctggg    11160
tgagcaaaaa caggaaggca aaatgccgca aaaaagggaa taaggcgac acggaaatgt     11220 tgaatactca tactcttcct ttttcaatat tattgaagca tttatcaggg ttattgtctc    11280
atgagcggat acatatttga atgtatttag aaaaataaac aaatagggat tccgcgcaca    11340
tttccccgaa aagtgccac                                                 11359
```

<210> SEQ ID NO 16
<211> LENGTH: 2332
<212> TYPE: PRT
<213> ORGANISM: Homo sapiens

<400> SEQUENCE: 16

| Ala | Thr | Arg | Arg | Tyr | Tyr | Leu | Gly | Ala | Val | Glu | Leu | Ser | Trp | Asp | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Met | Gln | Ser | Asp | Leu | Gly | Glu | Leu | Pro | Val | Asp | Ala | Arg | Phe | Pro | Pro |
|     |     |     | 20  |     |     |     |     | 25  |     |     |     |     | 30  |     |     |

| Arg | Val | Pro | Lys | Ser | Phe | Pro | Phe | Asn | Thr | Ser | Val | Val | Tyr | Lys | Lys |
|     |     |     | 35  |     |     |     |     | 40  |     |     |     |     | 45  |     |     |

| Thr | Leu | Phe | Val | Glu | Phe | Thr | Asp | His | Leu | Phe | Asn | Ile | Ala | Lys | Pro |
|     | 50  |     |     |     |     | 55  |     |     |     |     | 60  |     |     |     |     |

| Arg | Pro | Pro | Trp | Met | Gly | Leu | Leu | Gly | Pro | Thr | Ile | Gln | Ala | Glu | Val |
| 65  |     |     |     |     | 70  |     |     |     |     | 75  |     |     |     |     | 80  |

| Tyr | Asp | Thr | Val | Val | Ile | Thr | Leu | Lys | Asn | Met | Ala | Ser | His | Pro | Val |
|     |     |     |     | 85  |     |     |     |     | 90  |     |     |     |     | 95  |     |

| Ser | Leu | His | Ala | Val | Gly | Val | Ser | Tyr | Trp | Lys | Ala | Ser | Glu | Gly | Ala |
|     |     |     | 100 |     |     |     |     | 105 |     |     |     |     | 110 |     |     |

| Glu | Tyr | Asp | Asp | Gln | Thr | Ser | Gln | Arg | Glu | Lys | Glu | Asp | Asp | Lys | Val |
|     |     |     | 115 |     |     |     |     | 120 |     |     |     |     | 125 |     |     |

| Phe | Pro | Gly | Gly | Ser | His | Thr | Tyr | Val | Trp | Gln | Val | Leu | Lys | Glu | Asn |
|     | 130 |     |     |     |     | 135 |     |     |     |     | 140 |     |     |     |     |

| Gly | Pro | Met | Ala | Ser | Asp | Pro | Leu | Cys | Leu | Thr | Tyr | Ser | Tyr | Leu | Ser |
| 145 |     |     |     |     | 150 |     |     |     |     | 155 |     |     |     |     | 160 |

| His | Val | Asp | Leu | Val | Lys | Asp | Leu | Asn | Ser | Gly | Leu | Ile | Gly | Ala | Leu |
|     |     |     |     | 165 |     |     |     |     | 170 |     |     |     |     | 175 |     |

| Leu | Val | Cys | Arg | Glu | Gly | Ser | Leu | Ala | Lys | Glu | Lys | Thr | Gln | Thr | Leu |
|     |     |     | 180 |     |     |     |     | 185 |     |     |     |     | 190 |     |     |

| His | Lys | Phe | Ile | Leu | Leu | Phe | Ala | Val | Phe | Asp | Glu | Gly | Lys | Ser | Trp |
|     |     |     | 195 |     |     |     |     | 200 |     |     |     |     | 205 |     |     |

| His | Ser | Glu | Thr | Lys | Asn | Ser | Leu | Met | Gln | Asp | Arg | Asp | Ala | Ala | Ser |
|     |     |     | 210 |     |     |     |     | 215 |     |     |     |     | 220 |     |     |

| Ala | Arg | Ala | Trp | Pro | Lys | Met | His | Thr | Val | Asn | Gly | Tyr | Val | Asn | Arg |
| 225 |     |     |     |     | 230 |     |     |     |     | 235 |     |     |     |     | 240 |

```
Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
            290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
                340                 345                 350

Ser Glu Met Asp Val Val Arg Phe Asp Asp Asn Ser Pro Ser Phe
                355                 360                 365

Ile Gln Ile Arg Ser Val Ala Lys Lys His Pro Lys Thr Trp Val His
                370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
                435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
                610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655
```

```
Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
```

```
                    1070                 1075              1080
Pro Ile Pro Pro Asp Ala Gln Asn Pro Asp Met Ser Phe Phe Lys
     1085              1090                 1095
Met Leu Phe Leu Pro Glu Ser Ala Arg Trp Ile Gln Arg Thr His
     1100                 1105              1110
Gly Lys Asn Ser Leu Asn Ser Gly Gln Gly Pro Ser Pro Lys Gln
     1115              1120                 1125
Leu Val Ser Leu Gly Pro Glu Lys Ser Val Glu Gly Gln Asn Phe
     1130                 1135              1140
Leu Ser Glu Lys Asn Lys Val Val Val Gly Lys Gly Glu Phe Thr
     1145              1150                 1155
Lys Asp Val Gly Leu Lys Glu Met Val Phe Pro Ser Ser Arg Asn
     1160                 1165              1170
Leu Phe Leu Thr Asn Leu Asp Asn Leu His Glu Asn Asn Thr His
     1175              1180                 1185
Asn Gln Glu Lys Lys Ile Gln Glu Glu Ile Glu Lys Lys Glu Thr
     1190                 1195              1200
Leu Ile Gln Glu Asn Val Val Leu Pro Gln Ile His Thr Val Thr
     1205              1210                 1215
Gly Thr Lys Asn Phe Met Lys Asn Leu Phe Leu Leu Ser Thr Arg
     1220                 1225              1230
Gln Asn Val Glu Gly Ser Tyr Asp Gly Ala Tyr Ala Pro Val Leu
     1235              1240                 1245
Gln Asp Phe Arg Ser Leu Asn Asp Ser Thr Asn Arg Thr Lys Lys
     1250                 1255              1260
His Thr Ala His Phe Ser Lys Lys Gly Glu Glu Glu Asn Leu Glu
     1265              1270                 1275
Gly Leu Gly Asn Gln Thr Lys Gln Ile Val Glu Lys Tyr Ala Cys
     1280                 1285              1290
Thr Thr Arg Ile Ser Pro Asn Thr Ser Gln Gln Asn Phe Val Thr
     1295              1300                 1305
Gln Arg Ser Lys Arg Ala Leu Lys Gln Phe Arg Leu Pro Leu Glu
     1310                 1315              1320
Glu Thr Glu Leu Glu Lys Arg Ile Ile Val Asp Asp Thr Ser Thr
     1325              1330                 1335
Gln Trp Ser Lys Asn Met Lys His Leu Thr Pro Ser Thr Leu Thr
     1340                 1345              1350
Gln Ile Asp Tyr Asn Glu Lys Glu Lys Gly Ala Ile Thr Gln Ser
     1355              1360                 1365
Pro Leu Ser Asp Cys Leu Thr Arg Ser His Ser Ile Pro Gln Ala
     1370                 1375              1380
Asn Arg Ser Pro Leu Pro Ile Ala Lys Val Ser Ser Phe Pro Ser
     1385              1390                 1395
Ile Arg Pro Ile Tyr Leu Thr Arg Val Leu Phe Gln Asp Asn Ser
     1400                 1405              1410
Ser His Leu Pro Ala Ala Ser Tyr Arg Lys Lys Asp Ser Gly Val
     1415              1420                 1425
Gln Glu Ser Ser His Phe Leu Gln Gly Ala Lys Lys Asn Asn Leu
     1430                 1435              1440
Ser Leu Ala Ile Leu Thr Leu Glu Met Thr Gly Asp Gln Arg Glu
     1445              1450                 1455
Val Gly Ser Leu Gly Thr Ser Ala Thr Asn Ser Val Thr Tyr Lys
     1460                 1465              1470
```

```
Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860
```

```
Asn Pro Ala His Gly Arg Gln Val Thr Val Gln Glu Phe Ala Leu
1865                 1870                 1875

Phe Phe Thr Ile Phe Asp Glu Thr Lys Ser Trp Tyr Phe Thr Glu
1880                 1885                 1890

Asn Met Glu Arg Asn Cys Arg Ala Pro Cys Asn Ile Gln Met Glu
1895                 1900                 1905

Asp Pro Thr Phe Lys Glu Asn Tyr Arg Phe His Ala Ile Asn Gly
1910                 1915                 1920

Tyr Ile Met Asp Thr Leu Pro Gly Leu Val Met Ala Gln Asp Gln
1925                 1930                 1935

Arg Ile Arg Trp Tyr Leu Leu Ser Met Gly Ser Asn Glu Asn Ile
1940                 1945                 1950

His Ser Ile His Phe Ser Gly His Val Phe Thr Val Arg Lys Lys
1955                 1960                 1965

Glu Glu Tyr Lys Met Ala Leu Tyr Asn Leu Tyr Pro Gly Val Phe
1970                 1975                 1980

Glu Thr Val Glu Met Leu Pro Ser Lys Ala Gly Ile Trp Arg Val
1985                 1990                 1995

Glu Cys Leu Ile Gly Glu His Leu His Ala Gly Met Ser Thr Leu
2000                 2005                 2010

Phe Leu Val Tyr Ser Asn Lys Cys Gln Thr Pro Leu Gly Met Ala
2015                 2020                 2025

Ser Gly His Ile Arg Asp Phe Gln Ile Thr Ala Ser Gly Gln Tyr
2030                 2035                 2040

Gly Gln Trp Ala Pro Lys Leu Ala Arg Leu His Tyr Ser Gly Ser
2045                 2050                 2055

Ile Asn Ala Trp Ser Thr Lys Glu Pro Phe Ser Trp Ile Lys Val
2060                 2065                 2070

Asp Leu Leu Ala Pro Met Ile Ile His Gly Ile Lys Thr Gln Gly
2075                 2080                 2085

Ala Arg Gln Lys Phe Ser Ser Leu Tyr Ile Ser Gln Phe Ile Ile
2090                 2095                 2100

Met Tyr Ser Leu Asp Gly Lys Lys Trp Gln Thr Tyr Arg Gly Asn
2105                 2110                 2115

Ser Thr Gly Thr Leu Met Val Phe Phe Gly Asn Val Asp Ser Ser
2120                 2125                 2130

Gly Ile Lys His Asn Ile Phe Asn Pro Pro Ile Ile Ala Arg Tyr
2135                 2140                 2145

Ile Arg Leu His Pro Thr His Tyr Ser Ile Arg Ser Thr Leu Arg
2150                 2155                 2160

Met Glu Leu Met Gly Cys Asp Leu Asn Ser Cys Ser Met Pro Leu
2165                 2170                 2175

Gly Met Glu Ser Lys Ala Ile Ser Asp Ala Gln Ile Thr Ala Ser
2180                 2185                 2190

Ser Tyr Phe Thr Asn Met Phe Ala Thr Trp Ser Pro Ser Lys Ala
2195                 2200                 2205

Arg Leu His Leu Gln Gly Arg Ser Asn Ala Trp Arg Pro Gln Val
2210                 2215                 2220

Asn Asn Pro Lys Glu Trp Leu Gln Val Asp Phe Gln Lys Thr Met
2225                 2230                 2235

Lys Val Thr Gly Val Thr Thr Gln Gly Val Lys Ser Leu Leu Thr
2240                 2245                 2250

Ser Met Tyr Val Lys Glu Phe Leu Ile Ser Ser Ser Gln Asp Gly
```

```
                      2255                2260                2265
His Gln Trp Thr Leu Phe Phe Gln Asn Gly Lys Val Lys Val Phe
   2270                2275                2280

Gln Gly Asn Gln Asp Ser Phe Thr Pro Val Val Asn Ser Leu Asp
   2285                2290                2295

Pro Pro Leu Leu Thr Arg Tyr Leu Arg Ile His Pro Gln Ser Trp
   2300                2305                2310

Val His Gln Ile Ala Leu Arg Met Glu Val Leu Gly Cys Glu Ala
   2315                2320                2325

Gln Asp Leu Tyr
   2330

<210> SEQ ID NO 17
<211> LENGTH: 1114
<212> TYPE: DNA
<213> ORGANISM: Homo sapiens

<400> SEQUENCE: 17
gtggtgttcc atatttaaac ctcattcaac agggaagatt ggagctgaaa tgtgaaggag      60
ttgtgggagt ggaactacgt ggaaatctgg gggaaaggtg ttttgggtaa aagaaatagc    120
aagtgttgag gtccaggggc atgagtgtgc ttgatatttt agggaagagt aaggagacca    180
gtataaccag agtgagatga gactacgag gtcaggagaa agggcatgca gaccatgtgg     240
gatgctctag gacctaggcc atggtaaaga tgtagggttt taccctgatg gaggtcagaa    300
gccattggag gattctgaga agaggagtga caggactcgc tttatagttt taaattataa    360
ctataaatta tagtttttaa aacaatagtt gcctaacctc atgttatatg taaaactaca    420
gttttaaaaa ctataaattc ctcatactgg cagcagtgtg aggggcaagg gcaaaagcag    480
agagactaac aggttgctgg ttactcttgc tagtgcaagt gaattctaga atcttcgaca    540
acatccagaa cttctcttgc tgctgccact caggaagagg gttggagtag ctaggaata    600 ggagcacaaa ttaaagctcc tgttcacttt gacttctcca tccctctcct cctttcctta    660
aaggttctga ttaaagcaga cttatgcccc tactgctctc agaagtgaat gggttaagtt    720
tagcagcctc ccttttgcta cttcagttct tcctgtggct gcttcccact gataaaaagg    780
aagcaatcct atcggttact gcttagtgct gagcacatcc agtgggtaaa gttccttaaa    840
atgctctgca aagaaattgg gacttttcat taaatcagaa atttactttt ttccccctcc    900
tgggagctaa agatatttta gagaagaatt aaccttttgc ttctccagtt gaacatttgt    960
agcaataagt catgcaaata gagctctcca cctgcttctt tctgtgcctt ttgcgattct   1020
gctttagtgc caccagaaga tactacctgg gtgcagtgga actgtcatgg gactatatgc   1080
aaagtgatct cggtgagctg cctgtggacg caag                               1114

<210> SEQ ID NO 18
<211> LENGTH: 6909
<212> TYPE: DNA
<213> ORGANISM: Homo sapiens

<400> SEQUENCE: 18
tttcctccta gagtgccaaa atctttttcca ttcaacacct cagtcgtgta caaaaagact     60
ctgtttgtag aattcacgga tcaccttttc aacatcgcta agccaaggcc accctggatg    120
ggtctgctag gtcctaccat ccaggctgag gtttatgata cagtggtcat tacacttaag    180
aacatggctt cccatcctgt cagtcttcat gctgttggtg tatcctactg gaaagcttct    240
```

```
gagggagctg aatatgatga tcagaccagt caaagggaga agaagatga taaagtcttc      300
cctggtggaa gccatacata tgtctggcag gtcctgaaag agaatggtcc aatggcctct    360
gacccactgt gccttaccta ctcatatctt tctcatgtgg acctggtaaa agacttgaat    420
tcaggcctca ttggagccct actagtatgt agagaaggga gtctggccaa ggaaaagaca    480
cagaccttgc acaaatttat actactttt  gctgtatttg atgaagggaa agttggcac    540
tcagaaacaa agaactcctt gatgcaggat agggatgctg catctgctcg ggcctggcct    600
aaaatgcaca cagtcaatgg ttatgtaaac aggtctctgc caggtctgat tggatgccac    660
aggaaatcag tctattggca tgtgattgga atgggcacca ctcctgaagt gcactcaata    720
ttcctcgaag gtcacacatt tcttgtgagg aaccatcgcc aggcgtcctt ggaaatctcg    780
ccaataactt tccttactgc tcaaacactc ttgatggacc ttggacagtt tctactgttt    840
tgtcatatct cttcccacca acatgatggc atggaagctt atgtcaaagt agacagctgt    900
ccagaggaac cccaactacg aatgaaaaat aatgaagaag cggaagacta tgatgatgat    960
cttactgatt ctgaaatgga tgtggtcagg tttgatgatg acaactctcc ttcctttatc   1020
caaattcgct cagttgccaa gaagcatcct aaaacttggg tacattacat tgctgctgaa   1080
gaggaggact gggactatgc tcccttagtc ctcgcccccg atgacagaag ttataaaagt   1140
caatatttga acaatggccc tcagcggatt ggtaggaagt acaaaaaagt ccgatttatg   1200
gcatacacag atgaaacctt taagactcgt gaagctattc agcatgaatc aggaatcttg   1260
ggacctttac tttatgggga agttggagac acactgttga ttatatttaa gaatcaagca   1320
agcagaccat ataacatcta ccctcacgga atcactgatg tccgtccttt gtattcaagg   1380
agattaccaa aaggtgtaaa acatttgaag gattttccaa ttctgccagg agaaatattc   1440
aaatataaat ggacagtgac tgtagaagat gggccaacta atcagatcc  tcggtgcctg   1500
acccgctatt actctagttt cgttaatatg gagagagatc tagcttcagg actcattggc   1560
cctctcctca tctgctacaa agaatctgta gatcaaagag gaaaccagat aatgtcagac   1620
aagaggaatg tcatcctgtt ttctgtattt gatgagaacc gaagctggta cctcacagag   1680
aatatacaac gctttctccc caatccagct ggagtgcagc ttgaggatcc agagttccaa   1740
gcctccaaca tcatgcacag catcaatggc tatgttttg  atagtttgca gttgtcagtt   1800
tgtttgcatg aggtggcata ctggtacatt ctaagcattg gagcacagac tgacttcctt   1860
tctgtcttct tctctggata taccttcaaa cacaaaatgg tctatgaaga cacactcacc   1920
ctattcccat tctcaggaga aactgtcttc atgtcgatgg aaaacccagg tctatggatt   1980
ctggggtgcc acaactcaga ctttcggaac agaggcatga ccgccttact gaaggtttct   2040
agttgtgaca gaacactgg  tgattattac gaggacagtt atgaagatat ttcagcatac   2100
tgctgagta  aaaacaatgc cattgaacca agaagcttct cccagaattc aagacaccct   2160
agcactaggc aaaagcaatt taatgccacc acaattccag aaaatgacat agagaagact   2220
gacccttggt tgcacacag  aacacctatg cctaaaatac aaaatgtctc ctctagtgat   2280
ttgttgatgc tcttgcgaca gagtcctact ccacatgggc tatccttatc tgatctccaa   2340
gaagccaaat atgagacttt ttctgatgat ccatcacctg agcaatagag cagtaataac   2400
agcctgtctg aaatgacaca cttcaggcca cagctccatc acagtgggga catggtattt   2460
accctgagt  caggcctcca attaagatta aatgagaaac tggggacaac tgcagcaaca   2520
gagttgaaga aacttgattt caagtttct  agtacatcaa ataatctgat ttcaacaatt   2580
ccatcagaca atttggcagc aggtactgat aatacaagtt ccttaggacc cccaagtatg   2640
```

-continued

```
ccagttcatt atgatagtca attagatacc actctatttg gcaaaaagtc atctcccctt    2700
actgagtctg gtggacctct gagcttgagt gaagaaaata atgattcaaa gttgttagaa    2760
tcaggtttaa tgaatagcca agaaagttca tggggaaaaa atgtatcgtc aacagagagt    2820
ggtaggttat ttaaagggaa aagagctcat ggacctgctt tgttgactaa agataatgcc    2880
ttattcaaag ttagcatctc tttgttaaag acaaacaaaa cttccaataa ttcagcaact    2940
aatagaaaga ctcacattga tggcccatca ttattaattg agaatagtcc atcagtctgg    3000
caaaatatat tagaaagtga cactgagttt aaaaaagtga cacctttgat tcatgacaga    3060
atgcttatgg acaaaaatgc tacagctttg aggctaaatc atatgtcaaa taaaactact    3120
tcatcaaaaa acatggaaat ggtccaacag aaaaaagagg gccccattcc accagatgca    3180
caaaatccag atatgtcgtt ctttaagatg ctattcttgc cagaatcagc aaggtggata    3240
caaaggactc atggaaagaa ctctctgaac tctgggcaag gccccagtcc aaagcaatta    3300
gtatccttag gaccagaaaa atctgtggaa ggtcagaatt tcttgtctga aaaaacaaa     3360
gtggtagtag gaaagggtga atttacaaag gacgtaggac tcaaagagat ggtttttcca    3420
agcagcagaa acctatttct tactaacttg gataatttac atgaaaataa tacacacaat    3480
caagaaaaaa aaattcagga agaaatagaa aagaaggaaa cattaatcca agagaatgta    3540
gttttgcctc agatacatac agtgactggc actaagaatt tcatgaagaa ccttttctta    3600
ctgagcacta ggcaaaatgt agaaggttca tatgaggggg catatgctcc agtacttcaa    3660
gattttaggt cattaaatga ttcaacaaat agaacaaaga acacacagc tcatttctca    3720
aaaaaagggg aggaagaaaa cttggaaggc ttgggaaatc aaaccaagca aattgtagag    3780
aaatatgcat gcaccacaag gatatctcct aatacaagcc agcagaattt tgtcacgcaa    3840
cgtagtaaga gagctttgaa acaattcaga ctcccactag aagaaacaga acttgaaaaa    3900
aggataattg tggatgacac ctcaacccag tggtccaaaa acatgaaaca tttgaccccg    3960
agcaccctca cacagataga ctacaatgag aaggagaaag gggccattac tcagtctccc    4020
ttatcagatt gccttacgag gagtcatagc atccctcaag caaatagatc tccattaccc    4080
attgcaaagg tatcatcatt tccatctatt agacctatat atctgaccag ggtcctattc    4140
caagacaact cttctcatct tccagcagca tcttatagaa agaaagattc tggggtccaa    4200
gaaagcagtc atttcttaca aggagccaaa aaaatacc tttctttagc cattctaacc       4260
ttggagatga ctggtgatca aagagaggtt ggctccctgg ggacaagtgc cacaaattca    4320
gtcacataca agaaagttga gaacactgtt ctcccgaaac cagacttgcc caaaacatct    4380
ggcaaagttg aattgcttcc aaaagttcac atttatcaga aggacctatt ccctacggaa    4440
actagcaatg ggtctcctgg ccatctggat ctcgtggaag ggagccttct tcagggaaca    4500
gagggagcga ttaagtggaa tgaagcaaac agacctggaa agttccctt tctgagagta    4560
gcaacagaaa gctctgcaaa gactccctcc aagctattgg atcctcttgc ttgggataac    4620
cactatggta ctcagatacc aaaagaagag tggaaatccc aagagaagtc accagaaaaa    4680
acagctttta gaaaaaggaa taccattttg tccctgaacg cttgtgaaag caatcatgca    4740
atagcagcaa taaatgaggg acaaaataag cccgaaatag aagtcacctg gcaaagcaa    4800
ggtaggactg aaaggctgtg ctctcaaaac ccaccagtct tgaaacgcca tcaacgggaa    4860
ataactcgta ctactcttca gtcagatcaa gaggaaattg actatgatga taccatatca    4920
gttgaaatga agaaggaaga ttttgacatt tatgatgagg atgaaaatca gagcccccgc    4980
```

| | |
|---|---|
| agctttcaaa agaaaacacg acactatttt attgctgcag tggagaggct ctgggattat | 5040 |
| gggatgagta gctccccaca tgttctaaga acagggctc agagtggcag tgtccctcag | 5100 |
| ttcaagaaag ttgttttcca ggaatttact gatggctcct ttactcagcc cttataccgt | 5160 |
| ggagaactaa atgaacattt gggactcctg gggccatata aagagcaga agttgaagat | 5220 |
| aatatcatgg taactttcag aaatcaggcc tctcgtccct attccttcta ttctagcctt | 5280 |
| atttcttatg aggaagatca gaggcaagga gcagaaccta gaaaaaactt tgtcaagcct | 5340 |
| aatgaaacca aaacttactt ttggaaagtg caacatcata tggcacccac taaagatgag | 5400 |
| tttgactgca aagcctgggc ttatttctct gatgttgacc tggaaaaaga tgtgcactca | 5460 |
| ggcctgattg gacccctct ggtctgccac actaacacac tgaaccctgc tcatgggaga | 5520 |
| caagtgacag tacaggaatt tgctctgttt tcaccatct ttgatgagac caaaagctgg | 5580 |
| tacttcactg aaaatatgga agaaactgc agggctccct gcaatatcca gatggaagat | 5640 |
| cccactttta aagagaatta tcgcttccat gcaatcaatg ctacataat ggatacacta | 5700 |
| cctggcttag taatggctca ggatcaaagg attcgatggt atctgctcag catgggcagc | 5760 |
| aatgaaaaca tccattctat tcatttcagt ggacatgtgt tcactgtacg aaaaaaagag | 5820 |
| gagtataaaa tggcactgta caatctctat ccaggtgttt ttgagacagt ggaaatgtta | 5880 |
| ccatccaaag ctggaatttg gcgggtggaa tgccttattg gcgagcatct acatgctggg | 5940 |
| atgagcacac tttttctggt gtacagcaat aagtgtcaga ctcccctggg aatggcttct | 6000 |
| ggacacatta gagattttca gattacagct tcaggacaat atggacagtg gccccaaag | 6060 |
| ctggccagac ttcattattc cggatcaatc aatgcctgga gcaccaagga gccccttttct | 6120 |
| tggatcaagg tggatctgtt ggcaccaatg attattcacg gcatcaagac ccagggtgcc | 6180 |
| cgtcagaagt tctccagcct ctacatctct cagtttatca tcatgtatag tcttgatggg | 6240 |
| aagaagtggc agacttatcg aggaaattcc actggaacct taatggtctt ctttggcaat | 6300 |
| gtggattcat ctgggataaa acacaatatt tttaaccctc caattattgc tcgatacatc | 6360 |
| cgtttgcacc caactcatta tagcattcgc agcactcttc gcatggagtt gatgggctgt | 6420 |
| gatttaaata gttgcagcat gccattggga atggagagta agcaatatc agatgcacag | 6480 |
| attactgctt catcctactt taccaatatg tttgccacct ggtctccttc aaaagctcga | 6540 |
| cttcacctcc aagggaggag taatgcctgg agacctcagg tgaataatcc aaaagagtgg | 6600 |
| ctgcaagtgg acttccagaa gacagtgaaa gtcacaggag taactactca gggagtaaaa | 6660 |
| tctctgctta ccagcatgta tgtgaaggag ttcctcatct ccagcagtca agatggccat | 6720 |
| cagtggactc tcttttttca gaatggcaaa gtaaaggttt tcagggaaa tcaagactcc | 6780 |
| ttcacacctg tggtgaactc tctagaccca ccgttactga ctcgctacct tcgaattcac | 6840 |
| ccccagagtt gggtgcacca gattgccctg aggatggagg ttctgggctg cgaggcacag | 6900 |
| gacctctac | 6909 |

<210> SEQ ID NO 19
<211> LENGTH: 1109
<212> TYPE: DNA
<213> ORGANISM: Homo sapiens

<400> SEQUENCE: 19

| | |
|---|---|
| ggggccagga ttgtggggat gtaagtctgc ttggaggaag gtgcagacat cgggttagga | 60 |
| tggttgtgat gctacctggg ccccaaagaa acatttctgg gtaaggtgtg cacacatctg | 120 |
| tgttattagc agaaatgcta actgccaatt cttttcatag gtctgaccta tttgttgata | 180 |

```
ttttgttctg ttttgtccat tgcttctctt cgtcatatgc tgctcctcca gaatctagag    240
actggagtag agggagggtg aagggacaaa gacaaaactt ccctctgcct gcccaagctt    300
ccatagagag aatcaaggca atgaaatcca atcaatatca cacacaagtt tcatgtctgg    360
ttctcttgtg tgtacatgca atgtgtgttt ttataatatc ttttcctact ttgggtgtaa    420
ggataatatg agccttgagt tcagaagctt ttcgtgtttt gggggttctg gtgcatttag    480
gcagagtatt aaataacttt atcaatattg tctatggtca tcagttgatt cagattttc     540 tacctcttct tcagtaaata ttggtatatt ttggtctata ctttcataga aagcaatcta    600
ctgtccctag atttgataat gtattggtat caagttatgt aagagtctcc tgtgattttg    660
ttaaactgtt ctgtgtctgt agttatattt tcttttcat tccttatgtt gtatatgttc     720
tcttcctctc ttttaaaaat aatatttcca ggagttttct tgattttatt ggtcttgtca    780
agaattttct tttggtttga tttatcaatc tcttttttct ttctgttgca tcagtttctg    840
cttctacttt cattgattta ttccttcctt ctaatttcct ttggttcatt ttgttgttag    900 attttttgctt cttgagttga atgctgaaat catttatttt attttttttgt cttctttaaa  960 tgtgtattat aaagatttaa atataataca tagattgtgg ctgtgtaaac attaaatgtg   1020
gtcatgttgt acatacttta tattctttt ggttctttct gtttggctcc ccaccctctt    1080
tccacatcag tccccttctc ccccacctc                                      1109
```

FACTOR VIII MUTATION REPAIR AND TOLERANCE INDUCTION

CROSS-REFERENCE TO RELATED APPLICATIONS

This application is a continuation of application Ser. No. 14/649,910, which is the National Stage of International Application No. PCT/US2013/073751, filed Dec. 6, 2013, which claims the benefit of U.S. Provisional No. 61/734,678, filed Dec. 7, 2012, and U.S. Provisional No. 61/888,424, filed Oct. 8, 2013. The entirety of each of these applications is hereby incorporated by reference for all purposes.

GOVERNMENT INTEREST

This invention was made with government support under Grant Number HL 101851 awarded by the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HPLO_005_003_ST25.txt. The text file is 110 kb, was created on Apr. 26, 2019, and is being submitted electronically via EFS-Web.

BACKGROUND

Hemophilia (HA) is caused by loss-of-function mutations in the X-linked Factor (F) VIII gene, F8. Infusion of replacement plasma-derived (pd) or recombinant (r)FVIII is the standard of care to manage this chronic disease. Infusion of replacement FVIII, however, is not a cure for HA. Spontaneous bleeding remains a serious problem especially for those with severe HA, defined as circulating levels of FVIII coagulant activity (FVIII: C) below 1% of normal. Furthermore, the formation of anti-FVIII antibodies occurs in about 20% of all patients and more often in certain subpopulations of HA patients, such as African Americans (Viel K R, Ameri A, Abshire T C, et al. inhibitors of factor VIII in black patients with hemophilia. N Engl J Med. 360: 1618-27, 2009). Patients unable to be treated with FVIII experience more painful, joint bleeding and over time, a greater loss of mobility than patients whose HA is able to be managed with FVIII.

The approval in Europe of the first gene therapy obtained by uniQuire BV for alipogenic tiparvovec (trade name Glybera) to treat lipoprotein lipase (LPL) deficiency is a milestone in the quest to bring gene-based therapeutics into clinical use. Tiparvovec (AAV1-LPL(S447X)) incorporates an intact human LPL gene (LPL) variant, i.e. LPL (Ser447X), in an adeno-associated virus (AAV) vector, which is delivered intramuscularly (Gaudct D, Méthot J, Déry S, et al. Efficacy and long-term safety of alipogene tiparvovec (AAV1-PL(S447X)) gene therapy for lipoprotein lipase deficiency: an open-label trial. Gene Ther. Jun. 21, 2012. [Epub ahead of print]). The benefits of restoring continuous circulation of clinically meaningful levels of FVIII has motivated intense efforts over decades to develop an effective gene therapy for hemophilia. Use of an AAV vector to deliver the gene that encodes FIX is bearing fruit in the treatment of hemophilia B (HB) (Nathwani A, Tuddenham E G D, Rangarjan S, et al. Adeno-associated viral vector mediated gene transfer for hemophilia B. Blood. 118(21): 4-5, 2011). HB in six adult patients has been converted from a severe form to mild or moderate HB, following intravenous infusion of an AAV8 vector incorporating human F9 under the control of a liver restricted promoter (High K A. The gene therapy journey for hemophilia: are we there yet? Blood. 120(23): 4482-7, 2012). These patients have maintained a circulating FIX coagulant activity (FIX: C) level ranging from 1-6% of normal for 3 years.

Although very encouraging, the AAV vector is not suitable for many HB patients and safety concerns remain. AAV vectors have been engineered from a wild-type parvovirus capable of naturally infecting humans (Calcedo R, Morizono H, Wang L, et al. Adeno-associated virus antibody profiles in newborns, children, and adolescents. Clin Vaccine Immunol. 18(9): 1586-8, 2011; High K A. The gene therapy journey for hemophilia: are we there yet? Blood. 120(23): 4482-7, 2012). In the current AAV trial, patients are screened for neutralizing antibodies against AAV. Thus, about 30-50% of hemophilia patients may not be eligible for this treatment (High K A. The gene therapy journey for hemophilia: are we there yet? Blood. 120(23): 4482-7, 2012). Patients with liver disease are also not eligible for this therapy pending a better understanding of safety. Furthermore, because the vectors are predominantly non-integrating, they are not suitable for use with young patients because expression of FIX would be expected to be lost as the patient grows (High K A. The gene therapy journey for hemophilia: are we there yet? Blood. 120(23): 4482-7, 2012).

Transmission of AAV to the germ-line (semen) has been reported, but this appears to be transient (High K A. The gene therapy journey for hemophilia: are we there yet? Blood. 120(23): 4482-7, 2012). There is a trend toward a dose-dependent memory T-cell mediated response to AAV. This was seen in the first HB trial done with AAV and again in the current trial for HB (High K A. The gene therapy journey for hemophilia: are we there yet? Blood. 120(23): 4482-7, 2012). Whereas dosing in four patients in the range of $2 \times 10^{11}$ vg/kg did not provoke a T-cell response, it provided only low circulating FIX: C levels (1-3%). Dosing at $2 \times 10^{12}$ vg/kg in two patients led to initial robust levels of FIX in circulation, 8-10%; but, at 8-weeks post infusion, FIX levels began to fall and patients' liver enzymes rose (High K A. The gene therapy journey for hemophilia: are we there yet? Blood. 120(23): 4482-7, 2012). Treatment with prednisolone was effective in restoring normal liver enzyme levels and reducing AAV-capsid specific T-cells within PBMCs (High K A. The gene therapy journey for hemophilia: are we there yet? Blood. 120(23): 4482-7, 2012). In one patient, FIX fell to 2% of normal, but the other maintained FIX levels at 6% of normal (High K A. The gene therapy journey for hemophilia: are we there yet? Blood. 120(23): 4482-7, 2012). Questions remain about the long-term safety of therapy with AAV. Sequencing studies of organs from animals treated with AAV demonstrate that integration of AAV occurs (Naki H, Yant S R, Storm T A, Fuess S. Meuse L, Kay M S. Extrachromosomal recombinant adenoassociated virus vector genomes are primarily responsible for stable liver transduction in vivo. J Virol. 75(15): 6969-76, 2001). There is also one report of neonatal mice injected with AAV2 experiencing an increase in hepatocellular carcinoma with some tumors containing vector DNA (Chuah M K, Nair N, VandenDriessche T. Recent progress in gene therapy for hemophilia. Hum Gene Ther. 23(6): 557-65, 2012). Whether AAV will prove to have any utility for delivering F8 to HA patients is an open question. The cloning capacity of the vector is limited to replacement of the virus' 4.8 kilobase genome. Promising preclinical results have been obtained using an AAV packaged, non-naturally occurring F8 cDNA, encoding B-domain-deleted (BDD)-rFVIII. One major caveat is that the dosing required to achieve desired levels of circulating FVIII (1-7.8%) in these studies was a log higher than the highest dose used in the current HB trial (Chuah M K, Nair N, VandenDriessche T. Recent progress in gene therapy for hemophilia. Hum Gene Ther. 23(6): 557-65, 2012; Jonathan D. Finn, Margareth C. Eradication of neutralizing antibodies to FVIII in canine hemophilia A after liver gene therapy. Blood 116: 5842-5848 2010). Experience in the H B trial suggests that a memory T-cell response targeting liver cells would occur at these doses (High K A. The gene therapy journey for hemophilia: are we there yet? Blood. 120(23): 4482-7, 2012; Chuah M K, Nair N, VandenDriessche T. Recent progress in gene therapy for hemophilia. Hum Gene Ther. 23(6): 557-65, 2012).

A substantial effort has been made to develop lentiviral vectors for the delivery of clotting factors (Chuah M K, Nair N, VandenDriessche T. Recent progress in gene therapy for hemophilia. Hum Gene Ther. 23(6): 557-65, 2012). Lentiviral vectors can transfect non-cycling hepatocytes and integrate into the host genome. While the latter attribute may afford long term expression of the factor, it raises serious safety concerns regarding insertional mutagenesis leading to activation of oncogenes or inactivation of repressors. Studies in an HB mouse indicate that a preferred lentiviral vector could be one that harbors an inactivation mutation of the integrase, termed an IDLV (integrase defective lentiviral viral vector) (Matria 3, Chuah M K, VandenDriessche T. Recent advances in lentiviral vector development and applications. Mol Ther. 18: 477-90, 2010). Although factor expression is diminished following the elimination of integration, it appears this may be offset in the case of FIX by use of a rare hyper-activating variant in a codon-optimized F9 cDNA which dramatically boosts circulating FIX levels (Matria 3, Chuah M K, VandenDriessche T. Recent advances in lentiviral vector development and applications. Mol Ther. 18: 477-90, 2010). Another obstacle with lentivirus is its competence to transfect APC which triggers deleterious T-cell mediated immune responses that can neutralize the secreted clotting factor; or eliminate the transduced hepatocytes (VandenDriessche T, Thorerezn L, Naldini L, et al. Lentiviral vectors containing the human immunodeficiency virus type-1 central polypurine track can efficiently transduce non-dividing hepatocytes and antigen presenting cells in vivo. Blood. 100: 813-22, 2002). This can be reduced in animal models by including an additional layer of post-transcriptional control, mediated by the use of endogenous microRNA (miR) (Matria J, Chuah M K. VandenDriessche T. Recent advances in lentiviral vector development and applications. Mol Ther. 18: 477-90, 2010). Whether manipulations designed to mute the immune response to lentivirus will translate to man is unknown. In contrast to what occurs in man, in the canine model, AAV vectors did not elicit an immune response. Hence, while animal models have proven predictive with regard to forecasting delivery of factor clotting activity; no animal model, including the canine, recapitulates the more refined and sophisticated human immune response.

Use of autologous cells engineered with viral elements or nucleases capable of genomic editing may permit greater safety than intravenous delivery of targeted virus. Ex vivo protocols allow for screening of the genomes of manipulated cells to assess the frequency or viral insertions, double strand breaks in DNA (DSBs) or other potentially mutagenic events (Li H, Haurigot V. Doyon Y, et al. In vivo genome editing restores homeostasis in a mouse model of haemophilia. Nature. 475(7355): 217-21, 2011). Levels of blood clotting proteins needed to maintain hemostasis may be more readily achieved by expansion of large populations of cells ex vivo and reintroduction(s) into the patient. Promising work has been done with murine hematopoietic stem cells (HSCs) transduced with lentivirus to express FVIII, including in HA mice with high-titer FVIII inhibitors (Calcedo R, Morizono H, Wang L, et al. Adeno-associated virus antibody profiles in newborns, children, and adolescents. Clin Vaccine Immunol. 18(9): 1586-8, 2011; Chuah M K, Nair N, VandenDriessche T. Recent progress in gene therapy for hemophilia. Hum Gene Ther. 23(6): 557-65, 2012). Enthusiasm for these approaches is tempered, however, by recognition that in order to promote engraftment, conditioning agents such as busulfan, which can have serious side effects are required (Chuah M K, Nair N, VandenDriessche T. Recent progress in gene therapy for hemophilia. Hum Gene Ther. 23(6): 557-65, 2012). Furthermore, concerns remain regarding the long-term consequences of lentiviral incorporation into the genomes of hematopoietic stem cells (HSCs).

In addition, there is a critical need to identify ways to avoid FVIII inhibitor development and to abate a FVIII inhibitor response. An arduous (frequent infusions of FVIII) and extremely expensive (~$1 MM/patient) protocol called Immune Tolerance Induction (ITI) is the only approach proven to eradicate FVIII inhibitors in HA patients, yet fails among 30% of inhibitor patients (Morfin M. et. al. European study on orthopaedic status of haemophilia patients with inhibitors. Haemophiia September; 13(5):606-12 2007). Twenty percent of HA patients with the F8I22I develop inhibitors. In addition, HA patients with missense mutations expressed in the C2 domain of FVIII are more prone to inhibitor formation than those with mutations expressed elsewhere in their endogenous FVIII (8.7% C1/C2 domain vs. 3.6% non-C1/C2-domain; p-value: 0.01 sample size 1135 HA patients).

SUMMARY

The invention includes a method of treating a human subject with hemophilia A comprising selectively targeting and replacing a portion of the subject's genomic F8 gene sequence containing a mutation in the gene with a replacement sequence. In one embodiment, the resultant repaired gene, upon expression, confers improved coagulation functionality to the encoded FVIII protein of the subject compared to the non-repaired F8 gene. In one embodiment, the repaired gene, upon expression, provides for the induction of immune tolerance to an administered replacement FVIII protein product.

In one aspect of the invention, a method of treating hemophilia A in a subject is provided comprising introducing into a cell of the subject one or more isolated nucleic acids encoding a nuclease that targets a portion of the F8 gene containing a mutation that causes hemophilia A, wherein the nuclease creates a double stranded break in the F8 gene; and an isolated nucleic acid comprising a donor sequence comprising (i) a nucleic acid encoding a truncated FVIII polypeptide or (ii) a native F8 3' splice acceptor site operably linked to a nucleic acid encoding a truncated FVIII polypeptide, wherein the nucleic acid comprising the (i) a nucleic acid encoding a truncated FVIII polypeptide or (ii) native F8 3' splice acceptor site operably linked to a nucleic acid encoding a truncated FVIII polypeptide is flanked by nucleic acid sequences homologous to the nucleic acid sequences upstream and downstream of the double stranded break in the DNA, and wherein the resultant repaired gene, upon expression, confers improved coagulation functionality to the encoded FVIII protein of the subject compared to the non-repaired F8 gene. In one particular embodiment, the donor sequence comprises a native F8 3' splice acceptor site operably linked to a nucleic acid encoding a truncated FVIII polypeptide. In one embodiment, the subject is a human. In one embodiment, the nucleic acids encoding the nuclease introduced into the cell are ribonucleic acids.

In one aspect, the invention provides a method of inducing immune tolerance to a FVIII replacement product ((r)FVIII) in a subject having a FVIII deficiency and who will be administered, is being administered, or has been administered a (r)FVIII product comprising introducing into a cell of the subject one or more nucleic acids encoding a nuclease that targets a portion of the F8 gene containing a mutation that causes hemophilia A, wherein the nuclease creates a double stranded break in the F8 gene; and an isolated nucleic acid comprising a donor sequence comprising a (i) a nucleic acid encoding a truncated FVIII polypeptide or (ii) a native F8 3' splice acceptor site operably linked to a nucleic acid encoding a truncated FVIII polypeptide, wherein the nucleic acid comprising the (i) a nucleic acid encoding a truncated FVIII polypeptide or (ii) native F8 3' splice acceptor site operably linked to a nucleic acid encoding a truncated FVIII polypeptide is flanked by nucleic acid sequences homologous to the nucleic acid sequences upstream and downstream of the double stranded break in the DNA, and wherein the repaired gene, upon expression, provides for the induction of immune tolerance to an administered replacement FVIII protein product. In one particular embodiment, the donor sequence comprises a native F8 3' splice acceptor site operably linked to a nucleic acid encoding a truncated FVIII polypeptide. In one embodiment, the truncated FVIII polypeptide amino acid sequence shares homology with a positionally coordinated portion of the (r)FVIII amino acid sequence. In one embodiment, the truncated FVIII polypeptide amino acid sequence shares complete homology with a positionally correlated portion of the (r)FVIII amino acid sequence. In one embodiment, the subject is a human. In one embodiment, the nucleic acids encoding the nuclease introduced into the cell are ribonucleic acids.

In one embodiment, the F8 mutation targeted for replacement is a point mutation, a deletion, or an inversion. In one embodiment of the above described aspects, the nuclease targets the F8 gene at intron 1. In one embodiment, the nuclease targets a F8 gene at intron 14. In one embodiment, the nuclease targets the F8 gene at intron 22. In a particular embodiment, the mutation targeted for repair is an intron 22 inversion (I22I).

In one embodiment of the above described aspects, the nuclease targets the F8 gene at exon1/intron 1 junction, exon14/intron 14 junction, or exon22/intron 22 junction.

In one embodiment of the above described aspects, the encoded nuclease is a zinc finger nuclease (ZFN). In one embodiment, the encoded nuclease is a Transcription Activator-Like Effector Nuclease (TALEN). In one embodiment, the encoded nuclease is a CRISPR (Clustered Regularly Interspaced Short Palindromic Repeats)-associated (Cas) nuclease. In one particular embodiment, the encoded nuclease is a TALEN.

In the methods provided herein, the nucleic acids can optionally be in a vector.

In one embodiment of the above described aspects, the isolated nucleic acids described above can be administered directly to the subject so that introduction into the subject's cell occurs in viwo. The isolated nucleic acids can be delivered to the subject's cells in vive by a variety of mechanisms, including through uptake of naked DNA, liposome fusion, or through viral transduction, for example adenovirus, adeno-associated virus (AAV), or lentivirus introduction, as described further below.

In one embodiment of the above described aspects, the isolated nucleic acids described above can be administered ex vivo to a cell that has been isolated from the subject. The isolated nucleic acids can be delivered to the cells via any gene transfer mechanism, for example, calcium phosphate mediated gene delivery, electroporation, microinjection, liposome delivery, endocytosis, or viral delivery, for example, adenoviral, AAV, or lentiviral delivery, as described further below. The transduced cells can then be infused (e.g., in a pharmaceutically acceptable carrier) or homotopically transplanted back into the subject per standard methods for the cell or tissue type. Standard methods are known for transplantation or infusion of various cells into a subject. In one embodiment, the nucleic acids encoding the nuclease can be introduced into the cell as ribonucleic acids, for example mRNA. Alternatively, the nucleic acids can optionally be in a DNA vector.

In one embodiment of the above described aspects, the cells are endothelial cells. In one embodiment, the endothelial cell is a blood outgrowth endothelial cells (BOECs). In one embodiment, the cells repaired reside within the liver. In one embodiment, the cells are hepatocytes. In one embodiment, the cells are liver sinusoidal endothelial cells (LESCs). In one embodiment, the cells are stem cells. In one embodiment, the stem cells are induced pluripotent stem cells (iPSCs).

In one embodiment of the above described aspects, the nucleic acids described above are introduced into blood outgrowth endothelial cells (BOECs) that have been co-cultured with additional cell types. In one embodiment, the cells are blood outgrowth endothelial cells (BOECs) that have been co-cultured with hepatocytes or liver sinusoidal endothelial cell (LESCs), or both. In one embodiment, the cells are blood outgrowth endothelial cells (BOECs) that have been co-cultured with induced pluripotent stem cells (iPSCs).

Cells comprising the nucleic acids set forth herein are further provided. These cells can be, for example, endothelial cells, LSECs, BOECs, stem cells, for example iPSCs, or hepatocytes.

Recombinant viruses comprising any of the nucleic acids set forth herein are also provided.

Pharmaceutical compositions comprising any of the nucleic acids, vectors comprising the nucleic acids, recombinant viruses comprising the nucleic acids, or cells comprising the nucleic acids described herein are also provided. These pharmaceutical compositions can be in a pharmaceutically acceptable carrier.

DETAILED DESCRIPTION

Figure 1:
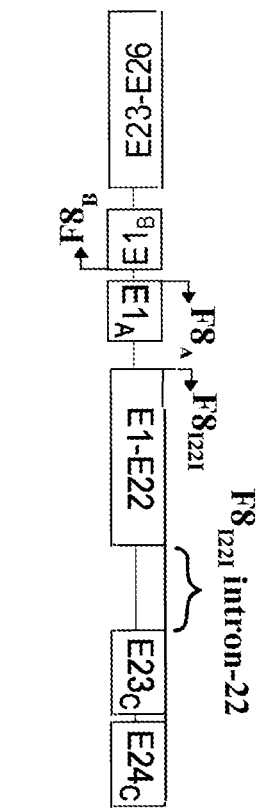
FIG. 1 is schematic illustration of the wild-type and intron-22-inverted FVIII loci (F8 & $F8_{I22I}$) and their expressed protein products ($FVIII_{FL}$ & $FVIII_B$ for F8 and $FVIII_{I22I}$ & $FVIII_B$ for $F8_{I22I}$).
Figure 1:
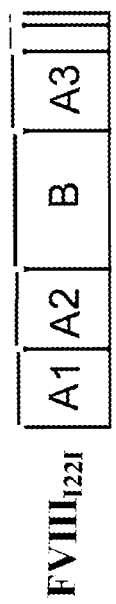
Figure 1:
Figure 1:
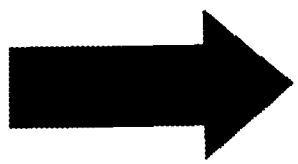
Figure 1:
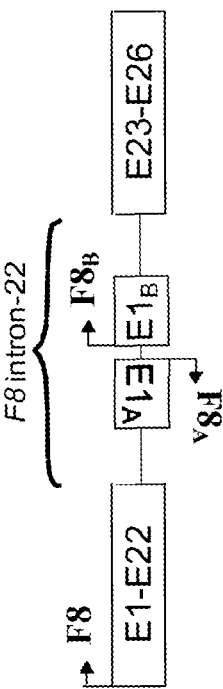
Figure 1:
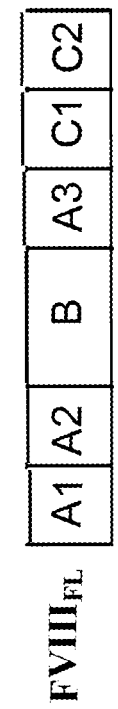
Figure 1:
Figure 1:
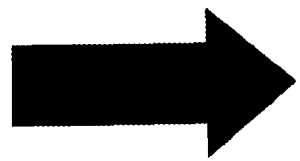

The invention includes a method of treating a subject with hemophilia A comprising selectively targeting and replacing a portion of the subject's genomic F8 gene sequence containing a mutation in the gene with a replacement sequence. In one embodiment, the resultant repaired gene containing the replacement sequence, upon expression, confers improved coagulation functionality to the encoded FVIII protein of the subject compared to the non-repaired F8 gene. Preferably, the levels of functional FVIII in circulation are adequate to obviate or reduce the need for infusions of replacement FVIII in the subject. In one embodiment, expression of functional FVIII reduces whole blood clotting time (WBCT). In one embodiment, the repaired gene, upon expression, provides for the induction of immune tolerance to an administered replacement FVIII protein product. In one embodiment, the subject is a human.

In one aspect of the invention, a method of treating hemophilia A in a subject is provided comprising introducing into a cell of the subject one or more nucleic acids encoding a nuclease that targets a portion of the human F8 gene containing a mutation that causes hemophilia A, wherein the nuclease creates a double stranded break in the F8 gene; and an isolated nucleic acid comprising (i) a nucleic acid encoding a truncated FVIII polypeptide or (ii) a native F8 3' splice acceptor site operably linked to a nucleic acid encoding a truncated FVIII polypeptide, wherein the nucleic acid comprising the (i) a nucleic acid encoding a truncated FVIII polypeptide or (ii) native F8 3' splice acceptor site operably linked to a nucleic acid encoding a truncated FVIII polypeptide is flanked by nucleic acid sequences homologous to the nucleic acid sequences upstream and downstream of the double stranded break in the DNA, and wherein the resultant repaired gene, upon expression, confers improved coagulation functionality to the encoded FVIII protein of the subject compared to the non-repaired F8 gene.

In one aspect, the invention is a method of inducing immune tolerance to a FVIII replacement product (r)FVIII in a subject having a FVIII deficiency and who will be administered, is being administered, or has been administered a (r)FVIII product comprising introducing into a cell of the subject one or more nucleic acids encoding a nuclease that targets a portion of the F8 gene containing a mutation that causes hemophilia A, wherein the nuclease creates a double stranded break in the F8 gene; and an isolated nucleic acid comprising (i) a nucleic acid encoding a truncated FVIII polypeptide or (ii) a native F8 3' splice acceptor site operably linked to a nucleic acid encoding a truncated FVIII polypeptide, wherein the nucleic acid comprising the (i) a nucleic acid encoding a truncated FVIII polypeptide or (ii) native F8 3' splice acceptor site operably linked to a nucleic acid encoding a truncated FVIII polypeptide is flanked by nucleic acid sequences homologous to the nucleic acid sequences upstream and downstream of the double stranded break in the DNA, and wherein the repaired gene, upon expression, provides for the induction of immune tolerance to an administered replacement FVIII protein product. The person administered the cells may have no anti-FVIII antibodies or have anti-FVIII antibodies as detected by ELISA or Bethesda assays. In one embodiment, the truncated FVIII polypeptide amino acid sequence shares homology with a portion of the (r)FVIII amino acid sequence. In one embodiment, the truncated FVIII polypeptide amino acid sequence shares homology with a similar portion of the (r)FVIII amino acid sequence. In one embodiment, the truncated FVIII polypeptide amino acid sequence shares complete homology with a similar portion of the (r)FVIII amino acid sequence.

1. Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide," and "protein" are used interchangeably to refer to a polymer of amino acid residues. The term also applies to amino acid polymers in which one or more amino acids are chemical analogues or modified derivatives of a corresponding naturally-occurring amino acids. As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

The term "truncated FVIII polypeptide" refers to an amino acid sequence that contains less than the full length FVIII protein. The truncated FVIII polypeptide can be truncated from the 5' end of the amino acid sequence. This produces an amino acid sequence corresponding to a portion of the FVIII protein, where a variable amount of the amino acid sequence is missing from the 5' end of the protein. In one embodiment, the truncated FVIII polypeptide contains exons 23-26. In one embodiment, the truncated FVIII polypeptide contains exons 2-26. In one embodiment, the truncated FVIII polypeptide contains exons 15-26.

2. F8 Gene Mutations

The F8 gene, located on the X chromosome, encodes a coagulation factor (Factor VIII) involved in the coagulation cascade that leads to clotting. Factor VIII is chiefly made by cells in the liver, and circulates in the bloodstream in an inactive form, bound to von Willebrand factor. Upon injury, FVIII is activated. The activated protein (FVIIIa) interacts with coagulation factor IX, leading to clotting.

Mutations in the F8 gene cause hemophilia A (HA). Over 2100 mutations in the gene have been identified, including point mutations, deletions, and insertion. One of the most common mutations includes inversion of intron 22, which leads to a severe type of HA. Mutations in F8 can lead to the production of an abnormally functioning FVIII protein or a reduced or absent amount of circulating FVIII protein, leading to the reduction of or absence of the ability to clot in response to injury.

In one aspect, the present invention is directed to the targeting and repair of F8 gene mutations in a subject suffering from hemophilia A using the methods described herein. Approximately 98% of patients with a diagnosis of hemophilia A are found to have a mutation in the F8 gene (i.e., intron 1 and 22 inversions, point mutations, insertions, and deletions).

Identification of an HA subject's mutation for targeting and repair can be readily made by using techniques known in the art. For example, DNA from the subject can be extracted from leukocytes in whole blood and all the endogenous coding regions and splice junctions of the F8 gene can be analyzed by restriction analysis, direct DNA sequence analysis, Denaturing Gradient Gel Electrophoresis (DGGE), Chemical Mismatch Cleavage (CMC), and Denaturing High Performance Liquid Chromatography (DHPLC) (see, for example: Higuchi et al., Characterization of mutations in the factor VIII gene by direct sequencing of amplified genomic DNA. Genomics 1990: 6(1); 65-71, Schwaab et al. Mutations in hemophilia A. Br J Haematol 1993; 83: 450-458; Schwaab et al. Factor VIII gene mutations found by a comparative study of SSCP, DGGE, and CMC and their analysis on a molecular model of factor VIII protein. Hum Genet 1997; 101: 323-332; Oldenburg et al. Evaluation of DHPLC in the analysis of hemophilia A. J Biochem Biophys Methods 2001; 47: 39-51). Intron 22 inversions account for approximately 45% and intron 1 inversions account for approximately 2% to 3%, of mutations associated with severe hemophilia A. The identification of inversions is well known in the art (see, for example, Viel at al. inhibitors of Factor VIII in Black Patients with Hemophilia. N Engl J Med 2009; 360(16): 1618-1627).

In one embodiment of the present invention, the gene mutation targeted for repair is a point mutation. In one embodiment, the gene mutation targeted for repair is a deletion. In one embodiment, the gene mutation targeted for repair is an inversion. In one embodiment, the gene mutation targeted for repair is an inversion of intron 1. In one embodiment, the gene mutation targeted for repair is an inversion of intron 22.

The intron 22 inversion mutation of the F8 gene accounts for ~45% of severe haemophilia A and is caused by an intra-chromosomal recombination within the gene. FIG. 1 shows a schematic illustration of the wild-type and intron 22-inverted FVIII loci (F8 & F8I22I). Transcription from the F8 promoter of both the F8 (wild-type) & F8I22I loci, which is normally functioning in both forms, yields polyadenylated mRNAs. The F8 mRNA has 26 exons, E1-E22 and E23-E26, all of which encode the amino acids found in the FVIII protein. Conversely, the F8I2I mRNA has at least 24 exons, E1-E22 (they are the same in F8 and thus encode FVIII amino acid sequence), and E23C & E24C (they are cryptic and encode no FVIII amino acid sequence). The sequence of intron-22, in both F8 & F8I22I, contains a bi-directional promoter that transcribes two additional mRNAs from the two genes: F8A, which is oriented oppositely to that of F8 & F8I22I and contains a single exon (box designated E1A), and F8B, which contains five exons that are oriented similarly transcriptionally to that of F8 & F8I22I and contains a single non-F8 first exon within I22 (box designated E1B) followed by four additional exons, which are identical to E23-E26 of F8. The F8A mRNA encodes the FVIIIA protein, which is now known as HAP40 (a cytoskeleton-interacting protein involved in endocytosis and thus functionally unrelated to the coagulation system) and has no FVIII amino acid sequence. The F8B mRNA encodes FVIII B, a protein with unknown function that has 8 non-FVIII amino acid residues at its N-terminus followed by 208 residues that represent FVIII residues 2125-2332.

3. Targeting Nucleases

The present invention provides for the targeting and repair of a mutated F8 gene in a subject with HA, including by introducing into a subject's cell one or more nucleic acids encoding a nuclease that specifically targets the F8 mutation. As discussed above, each subject's HA mutation for targeting and repair can be readily determined using techniques known in the art. The identified mutation in the subject can then be directly targeted by nucleases for correction. Alternatively, the subject's HA mutations can be corrected by targeting a region of the F8 gene upstream (or 5') from where the mutation occurs, and adding back the corresponding downstream coding regions of the F8 gene. For example, intron 14 could be targeted by the nucleases. This allows for gene repair of downstream mutations (i.e. missense mutations in exon 15 to exon 26) and inversions (such as the intron 22 inversion), due to the replacement of exons 15 to 26 with the wild-type sequences. In other embodiments, the F8 gene can be targeted at additional regions upstream, in order to capture an increasing proportion of F8 gene mutations causing HA. Thus, the nucleases can be engineered to specifically target a subject's F8 mutation, or alternatively, may target regions upstream of a subject's F8 mutation, in order to correct the mutation.

In the methods and compositions set forth herein, the one or more nucleic acids encoding a nuclease that targets a mutation in F8 for repair, for example, an intron 22 mutation in human F8, can be, for example, a transcription activator-like effector nuclease (TALEN), a zinc finger nuclease (ZFN), or a CRISPR (Clustered Regularly Interspaced Short Palindromic Repeats)-associated (Cas) nuclease.

Transcription Activator-Like Effector Nucleases (TALENs)

Transcription Activator-Like Effector Nucleases (TALENs) are emerging as a preferred alternative to zinc finger nucleases (ZFNs) for certain types of genome editing. The C-terminus of the TALEN component carries nuclear localization signals (NLSs), allowing import of the protein to the nucleus. Downstream of the NLSs, an acidic activation domain (AD) is also present, which is probably involved in the recruitment of the host transcriptional machinery. The central region harbors the most fascinating feature of TALENs and the most versatile. It is made up of a series of nearly identical 34/35 amino acids modules repeated in tandem. Residues in positions 12 and 13 are highly variable and are referred to as repeat-variable di-residues (RVDs). Studies of TALENs such as AvrBs3 from *X. axonopodlis* pv. *vesicatoria* and the genomic regions (e.g., promoters) they bind, led two teams to "crack the TALE code" by recognizing that each RVD in a repeat of a particular TALE determines the interaction with a single nucleotide. Most of the variation between TALES relies on the number (ranging from 5.5 to 33.5) and/or the order of the quasi-identical repeats. Estimates using design criteria derived from the features of naturally occurring TALEs suggest that, on average, a suitable TALEN target site may be found every 35 base pairs in genomic DNA. Compared with ZFNs, the cloning process of TALENs is easier, the specificity of recognized target sequences is higher, and off-target effects are lower. In one study, TALENs designed to target CCR5 were shown to have very little activity at the highly homologous CCR2 locus, as compared with CCR5-specific ZFNs that had similar activity at the two sites.

Figure 2:
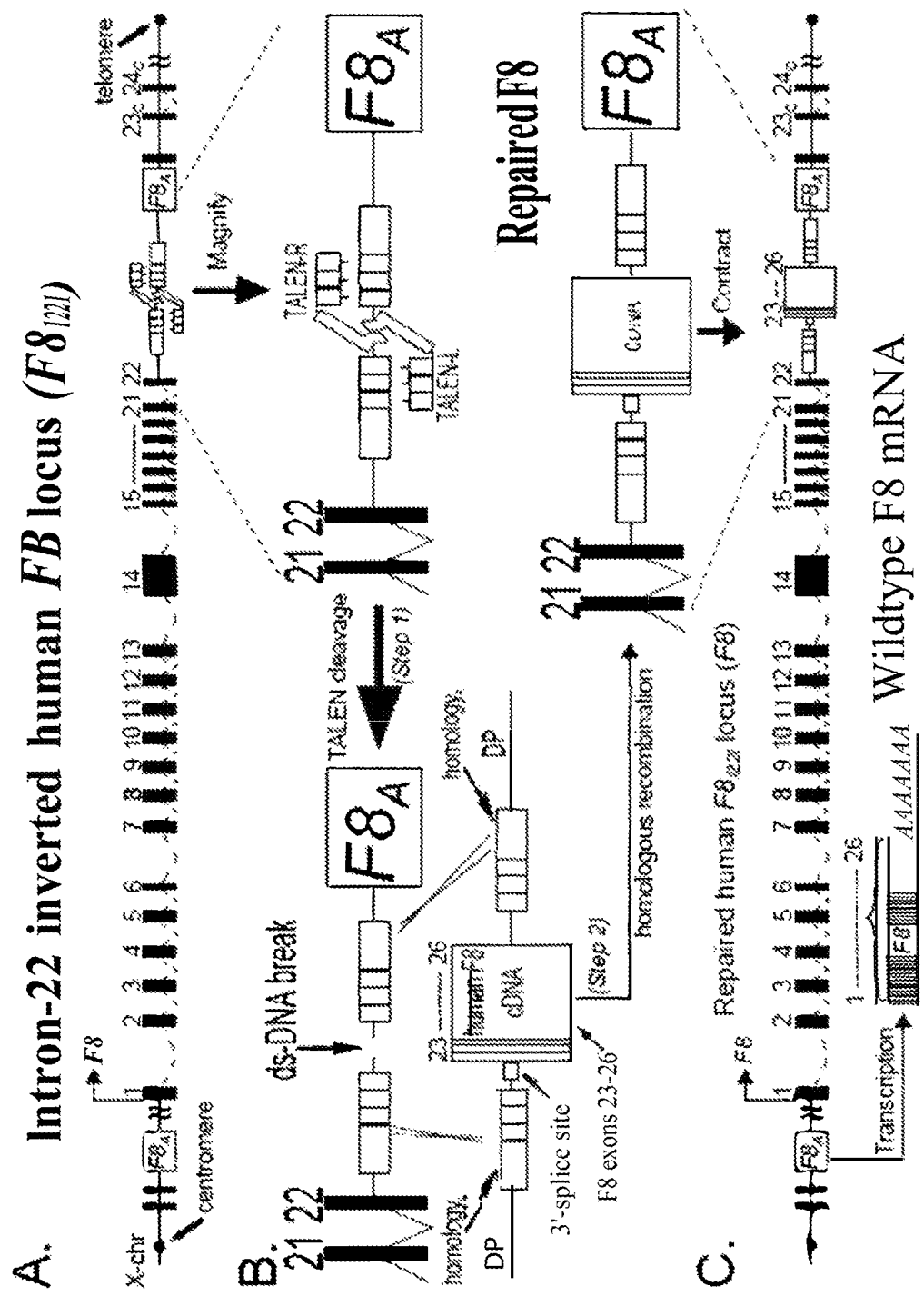
FIG. 2 is a schematic illustration of a TALEN-mediated genomic editing that can be used to repair the human intron-22 (I22)-inverted F8 locus, $F8_{I22I}$.
Figure 3:
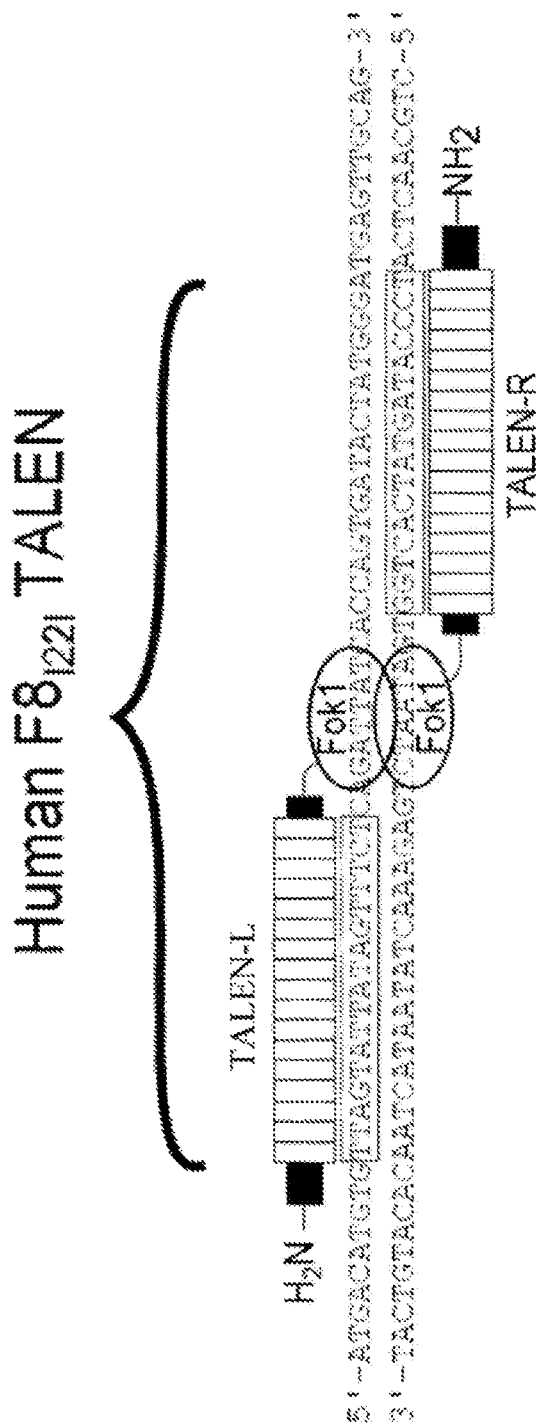
FIG. 3 shows a functional heterodimeric TALEN, comprised of its left and right monomer subunits (TALEN-L and TALEN-R), targeting the human F8 gene.

FIGS. 2 and 3 are exemplary illustrations outlining the use of a nucleic acid encoding a TALEN nuclease that can be used to repair the F8 gene in, for example, a human with an intron-22 (I22)-inverted F8 locus, F8I22I. As illustrated in FIG. 2(A), the major transcription unit of the F8I22I locus consists of 24 exons, which are designated exons 1-22 and exons 23C & 24C. The first 22 are the same as exons 1-22 of the wild-type FVIII structural locus (F8) but the last two (exon-23C & exon-24C) are cryptic and non-functional in non-hemophilic individuals as well as in patients whose HA is caused by F8 gene abnormalities other than the I22I-mutation. As illustrated in FIG. 2(B) the strategy to repair the I22I-mutation consists of introducing in the cell of the subject a nucleic acid encoding a functional TALEN—which is a heterodimeric nuclease comprised of a monomer subunit that binds 5' of the desired genome editing site (TALEN-L) and one that binds 3' of it (TALEN-R)—that is specific for a DNA sequence that is present in only a single copy per haploid human genome, which is approximately 1 kb downstream of the 3'-end of exon-22. Upon expression, once both monomers are bound to this specific sequence, their individual Fok 1 nuclease domains dimerize to form the active enzyme that catalyzes a double-stranded (ds) break in the DNA between their binding sites. If a ds-DNA break occurs in the presence of a second nucleic acid, for example a nucleic acid comprising a native FVIII 3' splice acceptor site operably linked to a nucleic acid encoding a truncated FVIII polypeptide encoding exons 23-26 (i.e., a "donor plasmid (DP)"), which contains a stretch of DNA with a left homology (HL) arm and right homology (HL) arm that have identical DNA sequences to that in the native chromosomal DNA 5' and 3' of the region flanking the break-point, homologous recombination (HR) occurs very efficiently. Following HR, the DNA segment between the left and right homology arms (which in this case contains a partial human F8 cDNA that contains, in-frame, all of exons 23-25 and the coding sequence of exon-26, with a functional 3'-splice site at its 5'-end) becomes permanently ligated/inserted into the chromosome. Since the DNA segment between the left and right homology arms comprises a partial human F8 cDNA (which, as shown in FIG. 2, contains, in-frame, all of exons 23-25 and the coding sequence of exon-26) fused at its 5'-end to a functional 3'-splice site, this TALEN catalyzes repair and converts F8I22I into wild-type F8-like locus and restore its ability to drive synthesis of a full-length fully functional wild-type FVIII protein.

FIG. 3 shows a functional heterodimeric TALEN, comprised of left and right monomer subunits (TALEN-L and TALEN-R), bound to its target "editing" sequence in intron 22 (I22) of the human FVIII structural locus (F8), ~1 kb downstream of the 3'-end of exon-22 (FIG. 3). Because the target binding sequence of each monomer is the same in both a wild-type FVIII gene (F8) and an I22-inverted FVIII gene (F8I22I), this TALEN edits each locus equally well. Following binding of this TALEN's monomeric subunits to their target I22-sequences in the F8I22I locus of a patient with severe HA caused by the I22-inversion (I22I)-mutation, the individual Fok1 nuclease domains are able to form a homo-dimer, i.e. the active form of the enzyme, which catalyzes a double-stranded (ds) break in the DNA between the monomer binding sites. If a ds-DNA break occurs in the presence of a donor plasmid containing the replacement or "repairing" sequence, which contains a stretch of DNA with left and right arms that have identical DNA sequences to that in the native chromosomal DNA, in the region flanking the break-point (see FIG. 2), homologous recombination (HR) occurs very efficiently. Following HR, the DNA segment between the left and right homology arms (which, as shown in FIG. 2, contains a partial human F8 cDNA that contains, in-frame, all of exons 23-25 and the coding sequence of exon-26, with a functional 3'-splice site at its 5'-end—i.e., the repairing sequence) becomes permanently ligated/inserted into the chromosome. Because the DNA segment between the left and right homology arms comprises a partial human F8 cDNA (which, as shown in FIG. 2, contains, in-frame, all of exons 23-25 and the coding sequence of exon-26) fused at its 5'-end to a functional 3'-splice site, this TALEN catalyzes repair and converts F8I22I into wild-type F8-like locus and restore its ability to drive synthesis of a full-length fully functional wild-type FVIII protein.

Figure 4:
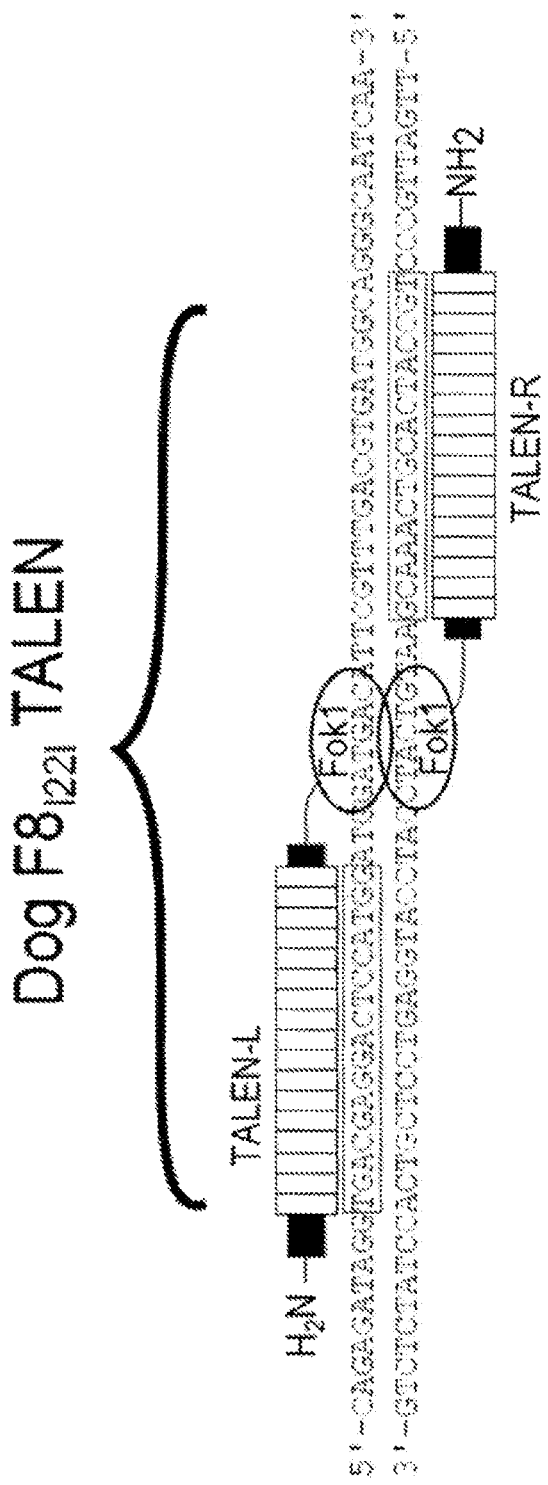
FIG. 4 shows a functional heterodimeric TALEN, comprised of its left and right monomer subunits (TALEN-L and TALEN-R) targeting the canine F8 gene

Likewise, FIG. 4 shows a functional heterodimeric TALEN targeting a F8 mutation in canine, comprised of its left and right monomer subunits (TALEN-L and TALEN-R), bound to its target "editing" sequence in the intron-22 (I22) of the canine FVIII structural locus (cF8), ~0.25 kb downstream of the 3'-end of exon-22. Because the target binding sequence of each monomer is the same in both a wild-type canine FVIII gene (cF8) and an I22-inverted FVIII gene (cF8I22I), this TALEN edits each locus equally well. Following binding of this TALEN's monomeric subunits to their target I22-sequences in the cF8I22I locus of a dog with severe HA caused by the I22-inversion (I22I)-mutation, their individual Fok1 nuclease domains are able to form a homo-dimer, i.e. the active form of the enzyme, which catalyzes a double-stranded (ds) break in the DNA between the monomer binding sites. If a ds-DNA break occurs in the presence of a donor plasmid, which contains a stretch of DNA with left and right arms that have identical DNA sequences to that in the native chromosomal DNA, in the region flanking the break-point (see FIG. 3 for the human F8 locus), homologous recombination (HR) occurs very efficiently. Following HR, the DNA segment between the left and right homology arms (which contains a partial cF8 cDNA that contains, in-frame, all of exons 23-25 and the coding sequence of exon-26, with a functional 3'-splice site at its 5'-end) becomes permanently ligated/inserted into the canine X-chromosome. Because the DNA segment between the left and right homology arms comprises a partial cF8 cDNA (which, as shown in FIG. 2 for the human F8I22I, contains, in-frame, all of canine exons 23-25 and the coding sequence of canine exon-26) fused at its 5'-end to a functional 3'-splice site, this TALEN catalyzes repair and converts cF8I22I into a wild-type cF8-like locus that restores its ability to drive synthesis of a full-length fully functional wild-type canine FVIII protein.

Figure 5:
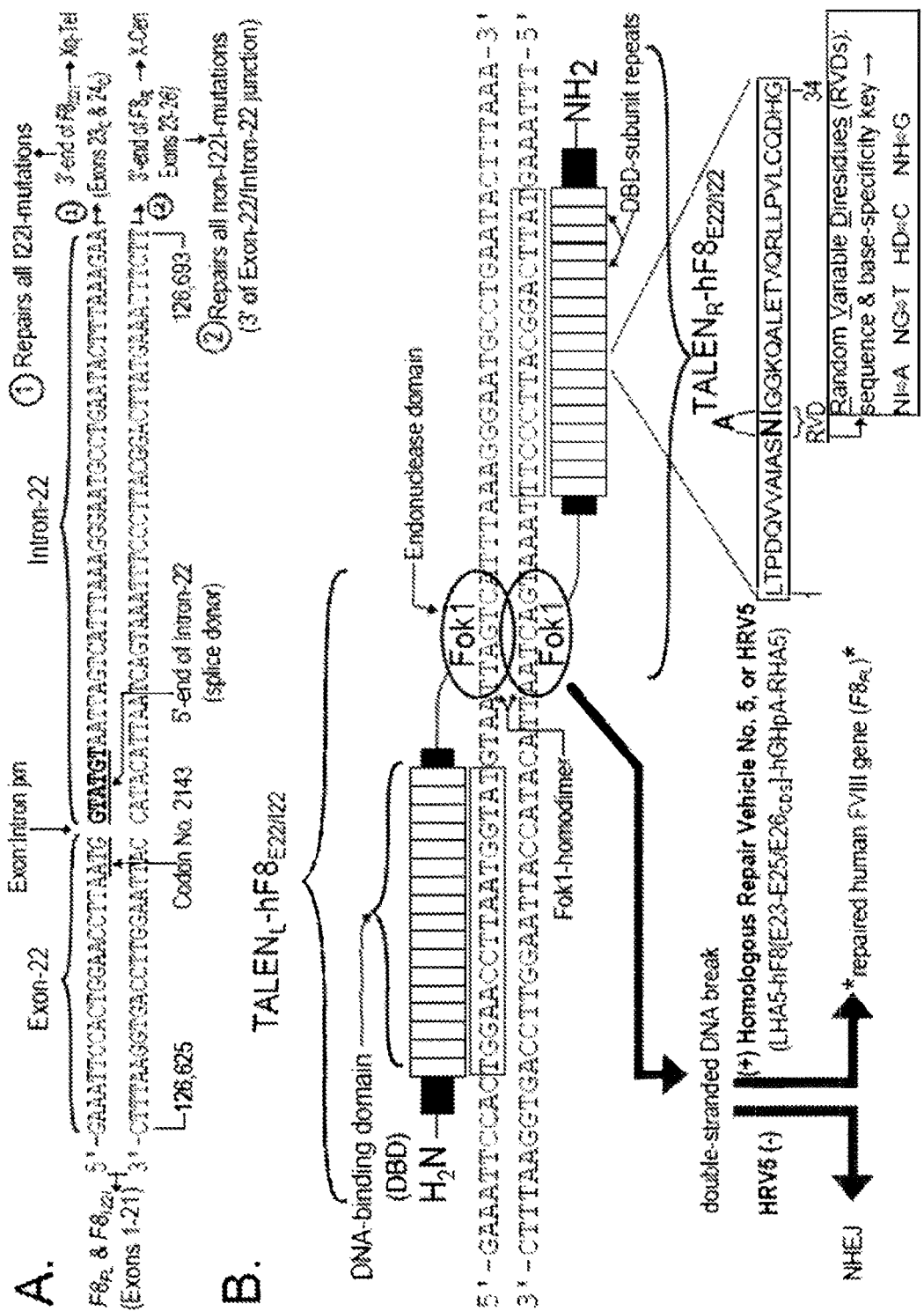
FIG. 5 illustrates the TALEN approach linking Exon 22 of the F8 gene to a nucleic acid encoding a truncated FVIII polypeptide encoding exons 23-26.

FIG. 5 illustrates a TALEN-mediated strategies to repair the human Factor VIII (FVIII) gene (F8) mutations in >50% of all patients with severe hemophilia-A (HA), including the highly recurrent intron-22 (I22)-inversion (I22I)-mutation. FIG. 5 highlights the TALEN approach linking Exon 22 of the F8 gene to a nucleic acid encoding a truncated FVIII polypeptide encoding exons 23-26. Panel A of Figure S shows the specific F8 genomic DNA sequence (spanning genic base positions 126,625-126,693) within which a double-stranded DNA break is introduced (designated "Endonuclease domain" in Panel B) by this strategy's functional TALEN dimer. The left and right TALEN protein sequences for the variable DNA-binding domain are listed as Seq. ID. No. 4 and Seq. ID. No. 6, respectively. An example of DNA sequences encoding the left and right TALEN DNA-binding domains are listed as Seq. ID. No 5 and Seq. ID. No. 7, respectively. Because of the degeneracy of the genetic code, there are many possible constructs that can be used to encode TALEN DNA-binding domains. In some embodiments, the codons are optimized for expression of the DNA constructs. Panel A in FIG. 5 also shows the F8 genomic DNA sequence containing (i) the recognition sites for the left (TALEN$_L$-hF8$_{E22/I22}$) and right (TALEN$_R$-hF8$_{E22/I22}$) TALEN monomers comprising F8-TALEN-5 and (ii) the intervening spacer region within which the F8-TALEN-5's endonuclease activity creates the double-stranded DNA breaks (DSDBs) required for inducing the physiologic cellular machinery that mediates the homology-dependent DNA repair pathway. Panel A in FIG. 5 also shows important orienting landmarks, including the following: (i) Nucleotide coordinates of this region (based on the February 2009, human genome assembly [UCSC Genome Browser: http://genome.ucsc.edu/]) are numbered with respect to the wild-type F8 transcription unit, where the initial (5'-most) base of the F8 pre-mRNA (5'-base of exon-1 [E1]) is designated +1 or 1 (note that this base corresponds to X-chromosome position 154,250,998) and includes the appropriate intronic sequence bases in calculating the genomic base positioning; (ii) Relative location of the X-chromosome's centromere (X-Cen) and its long-arm telomere (Xq-Tel), as transcription of the wild-type F8 locus and all of its mutant alleles causing HA—with the exception of its two recurrent intronic inversions, the intron-1 (I1)-inversion (I1I)- and the I22I-mutations—is oriented towards X-Cen. Transcription of the I1- and I22-inverted F8 loci, in contrast, are oriented towards Xq-Tel. This strategy repairs (i) the highly recurrent I22I-mutation—also designated F8$_{I22I}$—which causes ~45% of all unrelated patients with severe hemophilia-A (HA) and (ii) mutant F8 loci in ~20% of all other patients with severe HA, who are either known or found to have any one of the >200 distinct mutations that have been found (according to the HAMSTeRS database of HA-causing F8 mutations) thus far to reside down-stream (i.e., 3') of exon-22 (E22). The last codon of exon 22 encodes methionine (Met [M]) as translated residue 2,143 (2,124 in the mature FVIII protein secreted into plasma). Most mutations repaired are "previously known" (literature and/or HAMSTeRS or other databases), some have never been identified previously; the F8 abnormalities in this latter category are "private" (found only in this particular) to the patient/family.

Panel B in FIG. 5 shows the functional aspects of the TALENs including the overall DNA-binding domain (DBD) and the DBD-subunit repeats of the left and right monomers (TALEN$_L$-hF8$_{E22/I22}$ and TALEN$_R$-hF8$_{E22/I22}$). Also shown are the (i) specific DNA sequences recognized by each TALEN monomer (shown in bold font immediately below each DBD-subunit); (ii) the spacer region between the DNA recognition sequences of the TALEN monomers contains the sequence within which the dimerized Fok1 catalytic domains, which form a functional endonuclease, introduce a double-stranded DNA break (DSDB). As shown in the lower left portion of FIG. 5, the introduction of a DSDB in the presence of homologous repair vehicle no. 5 (HRV5), the nucleotide sequence of which is provided below as Seq. ID. No. 12, results in the in-frame integration, immediately 3' to exon 22, of the partial human F8 cDNA comprising exons 23, 24 and 25 and the protein coding sequence, or CDS, of exon 26 (designated hF8[E23-E25/E26$_{CDS}$]). In one embodiment, the TALEN constructs depicted in FIG. 5 can be used to repair all I22I inversion mutations (See #1 pathway). In another embodiment, the same constructs can be used to repair non-I22I F8 mutations that occur 3' (i.e. downstream) of the exon-22/intron-22 junction (See #2 pathway).

Figure 6:
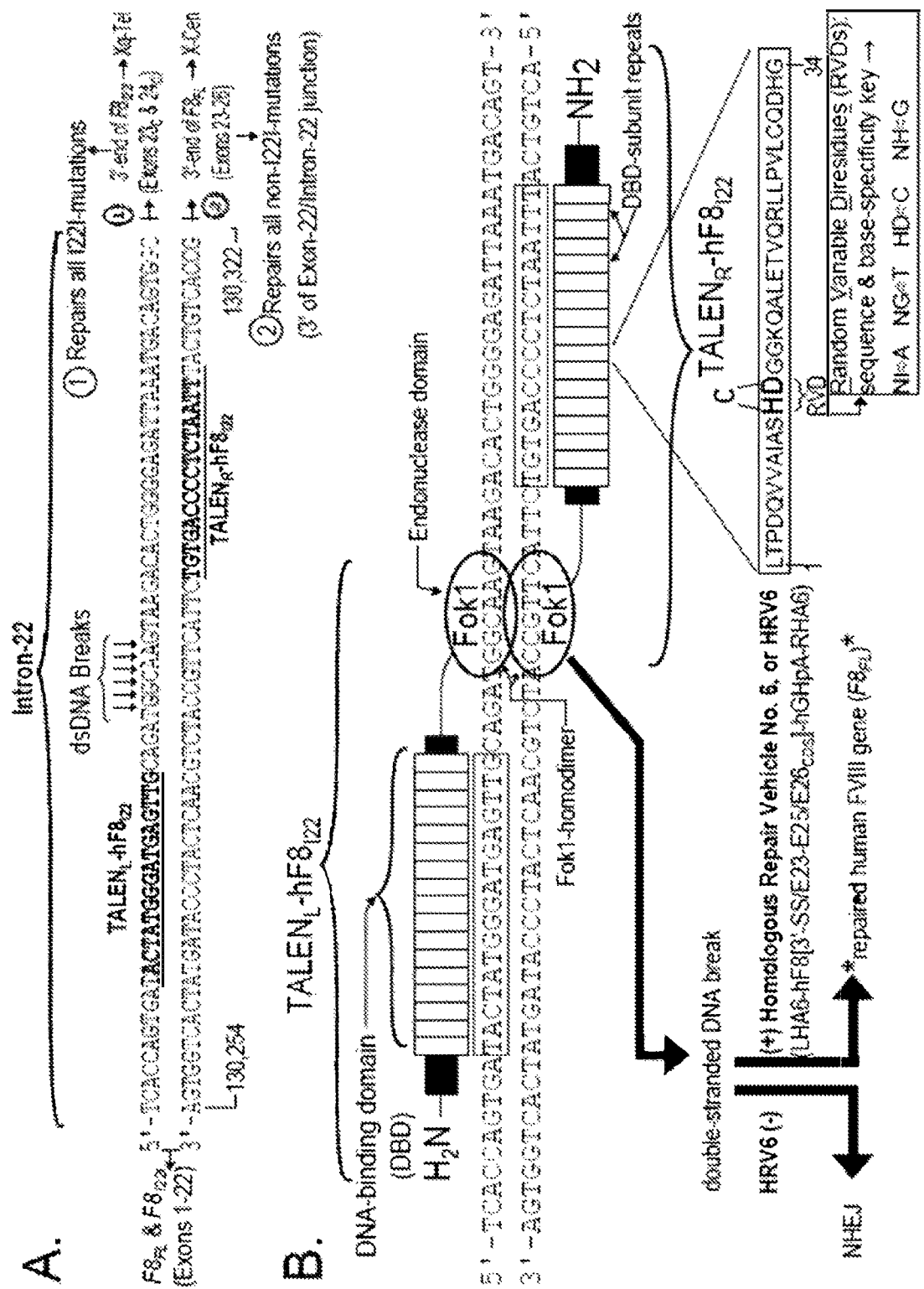
FIG. 6 illustrates the TALEN approach linking Intron 22 to a F8 3' splice acceptor site operably linked to a nucleic acid encoding a truncated FVIII polypeptide.
Figure 7:
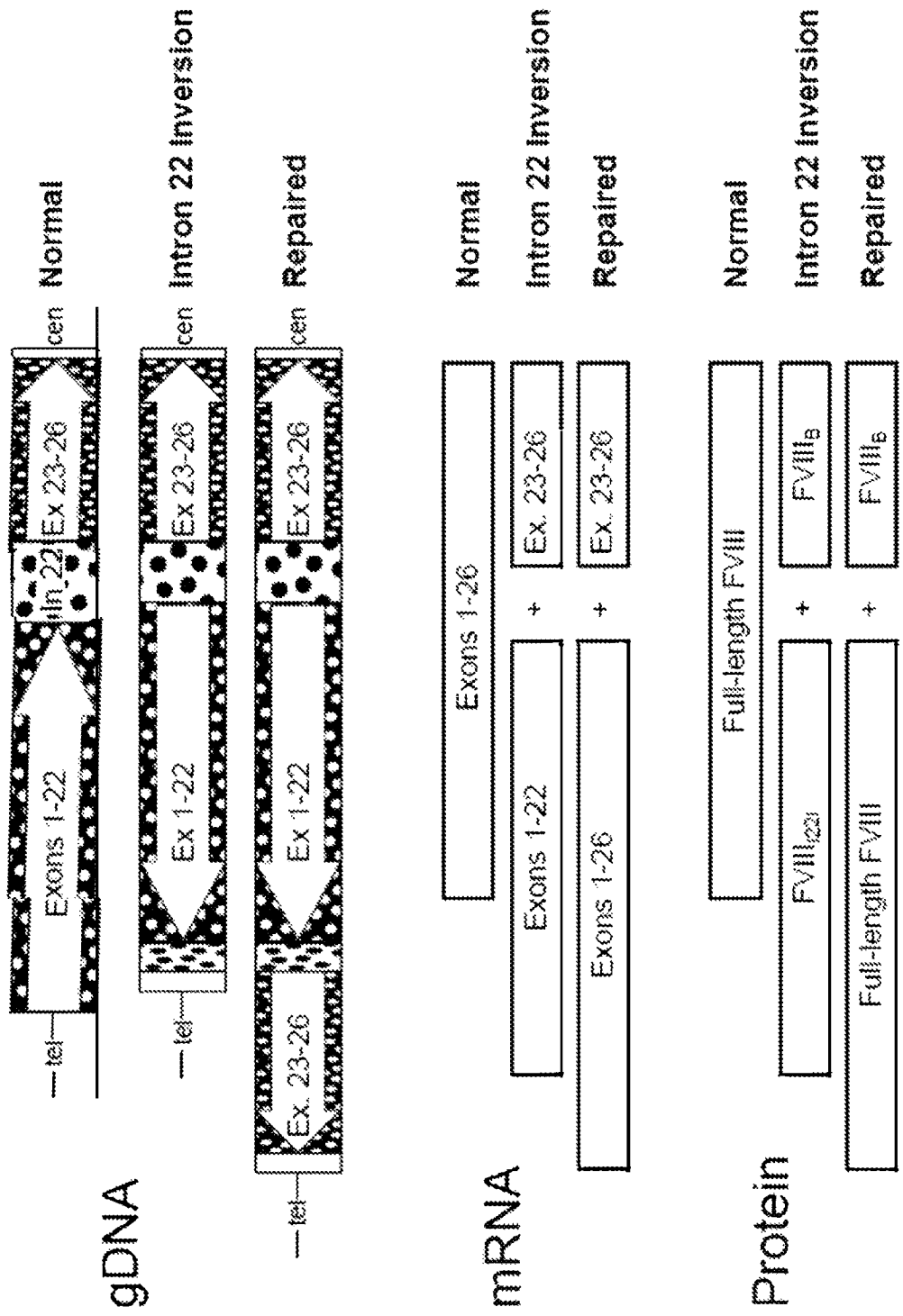
FIG. 7 shows a comparison of expected genomic DNA, spliced RNA and proteins pre and post repair.

FIG. 6 illustrates a TALEN-mediated strategy to repair the human Factor VIII (FVIII) gene (F8) mutations in >50% of all patients with severe hemophilia-A (HA), including the highly recurrent intron-22 (I22)-inversion (I22I)-mutation. FIG. 6 highlights the TALEN approach linking intron 22 of the F8 gene to a nucleic acid encoding a truncated FVIII polypeptide encoding exons 23-26. Panel A shows the specific F8 genomic DNA sequence within which a double-stranded DNA break is introduced (designated "Endonuclease domain" in Panel B) by this strategy's functional TALEN dimer. The left and right TALEN protein sequences for the variable DNA-binding domain are listed as Seq. ID. No. 8 and Seq. ID. No. 10, respectively. Examples of DNA sequences encoding the left and right TALEN DNA-binding domains are listed as Seq. ID. No. 9 and Seq. ID. No. 11, respectively. Because of the degeneracy of the genetic code, there are many possible constructs that can be used to encode TALEN DNA-binding domains. In some embodiments, the codons are optimized for expression of the DNA constructs. Panel A in FIG. 6 also shows important orienting landmarks, including the: (i) nucleotide coordinates of this region (based on the February 2009, human genome assembly available at the UCSC Genome Browser: http://genome.ucsc.edu/) are numbered with respect to the wild-type F8 transcription unit, where the initial (5'-most) base of the F8 pre-mRNA (5' most base of exon-1 [E1]) is designated +1 or 1 (note that this base corresponds to X-chromosome position 154,250,998) and includes the appropriate intronic sequence bases in calculating the genomic base positioning; (ii) relative location of the X-chromosome's centromere (X-Cen) and its long-arm telomere (Xq-Tel), as transcription of the wild-type F8 locus and all of its mutant alleles causing HA—with the exception of its two recurrent intronic inversions, the intron-1 (I1)-inversion (I1I)- and the I22I-mutations—is oriented towards X-Cen; Transcription of the I1- and I22-inverted F8 loci, in contrast, is oriented towards Xq-Tel. This strategy repairs (i) the highly recurrent I22I-mutation—also designated F8$_{I22I}$—which causes ~45% of all unrelated patients with severe hemophilia-A (HA) and (ii) mutant F8 loci in ~20% of all other patients with severe HA, who are either known or found to have any one of the >200 distinct mutations that have been found (according to the HAMSTeRS database of HA-causing F8 mutations) thus far to reside down-stream (i.e., 3') of exon-22 (E22). The last codon of E22 entirely encodes methionine (Met [M]) as translated residue 2,143 (2,124 in the mature FVIII protein secreted into plasma). Most mutations repaired are "previously known" (literature and/or HAMSTeRS or other databases), but some have never been identified previously. The F8 abnormalities in this latter category are "private" (found only in this particular) to the patient/family.

Panel B in FIG. 6 shows the functional aspects of the TALENs including the overall DNA-binding domain (DBD) and the DBD-subunit repeats of the left and right monomers (TALEN$_L$-hF8$_{I22}$ and TALEN$_R$-hF8$_{I22}$). Also shown are the (i) specific DNA sequences recognized by each TALEN monomer (shown in bold font immediately below each DBD-subunit); (ii) the spacer region between the DNA recognition sequences of the TALEN monomers contains the sequence within which the dimerized Fok1 catalytic domains, which form a functional endonuclease, introduce a double-stranded DNA break (DSDB). As shown in the lower left portion of FIG. 6, the introduction of a DSDB in the presence of a homologous repair vehicle, the nucleotide sequence of which is listed as Seq. ID. No. 13, results in the integration into intron 22 of a native F8 3' splice acceptor site operably linked to a nucleic acid encoding F8 exons 23, 24 and 25 and the protein coding sequence, or CDS, of exon 26 (designated hF8[E23-E25/E26: s]). In one embodiment, the TALEN constructs depicted in FIG. 6 can be used to repair all I22I inversion mutations (See #1 pathway). In another embodiment, the same constructs are used to repair non-I22I F8 mutations that occur 3' (i.e. downstream) of the exon-22/intron-22 junction (See #2 pathway).

In some embodiments, nucleic acids encoding nucleases specifically target intron1, intron 14, or intron22. In some embodiments, nucleic acids encoding nucleases specifically target the exon1/intron1 junction; exon14/intron14 junction; or the exon22/intron22 junction.

Figure 9:
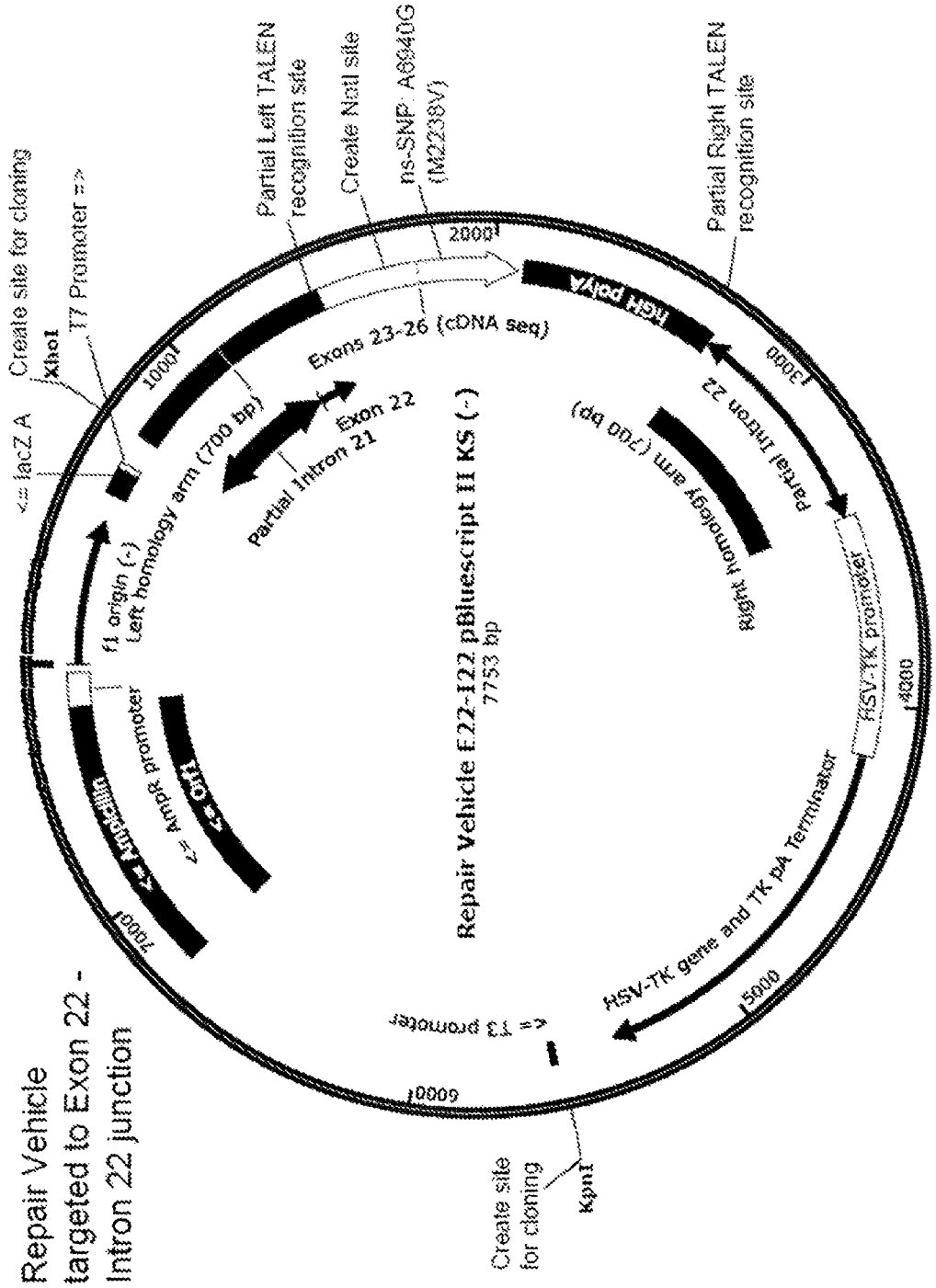
FIG. 9 illustrates the donor plasmid targeting the F8 Exon22/Intron22 junction using a TALEN nuclease, zinc finger nuclease, or cas nuclease approach.

FIG. 9 illustrates an example of a donor plasmid that can be used to repair the F8 gene at the exon22/intron22 junction using a TALEN nuclease, zinc finger nuclease, or cas nuclease approach. The donor plasmid contains the cDNA sequence for exons 23-26 of the F8 gene and a polyadenylation signal sequence flanked by two regions of homology to the F8 gene. The left homology region contains a DNA sequence (approximately 700 base pairs) that is homologous to part of Intron 21 and Exon22 of the F8 gene. The right homology region contains a DNA sequence (approximately 700 base pairs) that is homologous to part of intron 22 of the F8 gene. Upon successful homologous recombination into the F8 locus, the integrated construct expresses the resulting mRNA encoding the wild-type (corrected) version of the F8 protein. The sequence of the plasmid depicted in FIG. 9 is listed as Seq. ID. No. 12. The annotation of Seq. ID. No. 12 is provided in Table 1 below.

TABLE 1

Repair vehicle targeted to the Exon 22-Intron 22 junction of F8 7753 bp DNA linear

| LOCUS | RepairVehicle |
|---|---|
| FEATURES | Location/Qualifiers |
| misc_feature | 21 . . . 327 |
| | /note="f1 origin (-) " |
| misc_feature | 6765 . . . 7625 |
| | /note="<= Ampicillin" |
| misc_feature | 471 . . . 614 |
| | /lable=<= lacZ A |
| misc_feature | 626 . . . 644 |
| | /note="T7 promoter =>" |
| misc_feature | 5564 . . . 5583 |
| | /note="T3 promoter =>" |
| misc_feature | 6765 . . . 7625 |
| | /note="<= Orf1" |
| misc_feature | 7667 . . . 7695 |
| | /note="<= AmpR promoter" |
| misc_feature | 658 . . . 740 |
| | /note="MCS" |
| misc_feature | 1446 . . . 2072 |
| | /note="Exons 23-26 (cDNA sap) " |
| misc_feature | 1730 . . . 1737 |
| | /note="Create NotI site" |
| misc_feature | 2082 . . . 2707 |
| | /note="hGH polyA" |
| misc_feature | 1785 . . . 1787 |
| | /note="ns-SNP: A6940G (M2238V) " |
| misc_feature | 3408 . . . 4160 |
| | /note="HSV-TK promoter " |
| misc_feature | 4161 . . . 5546 |
| | /note="HSV-TK gene and TK pA Terminator " |
| misc_feature | 741 . . . 745 |
| | /note="Create site for coolng" |
| misc_feature | 5547 . . . 5551 |
| | /note="Create site for cloning" |
| misc_feature | 746 . . . 1445 |
| | /note="Left homolgy arm (700 bP) " |
| misc_feature | 1290 . . . 1445 |
| | /note="Exon 22" |
| misc_feature | 1438 . . . 1445 |
| | /note=""Partial Left TALEN recogniton site" |
| misc_feature | 2708 . . . 3407 |
| | /note="Right homology arm (700 bp) " |
| misc_feature | 2708 . . . 2716 |
| | /note="Partial Right TALEN recognition site" |
| misc_feature | 2708 . . . .3407 |
| | /note="Partial Intron 22" |
| misc_feature | 746 . . . 1289 |
| | /note="Partial Intron 21" |
| source | 1 . . . 7753 |
| | /dnas_title="RepairVehicle E22-I22 pBluescript" |

Figure 10:
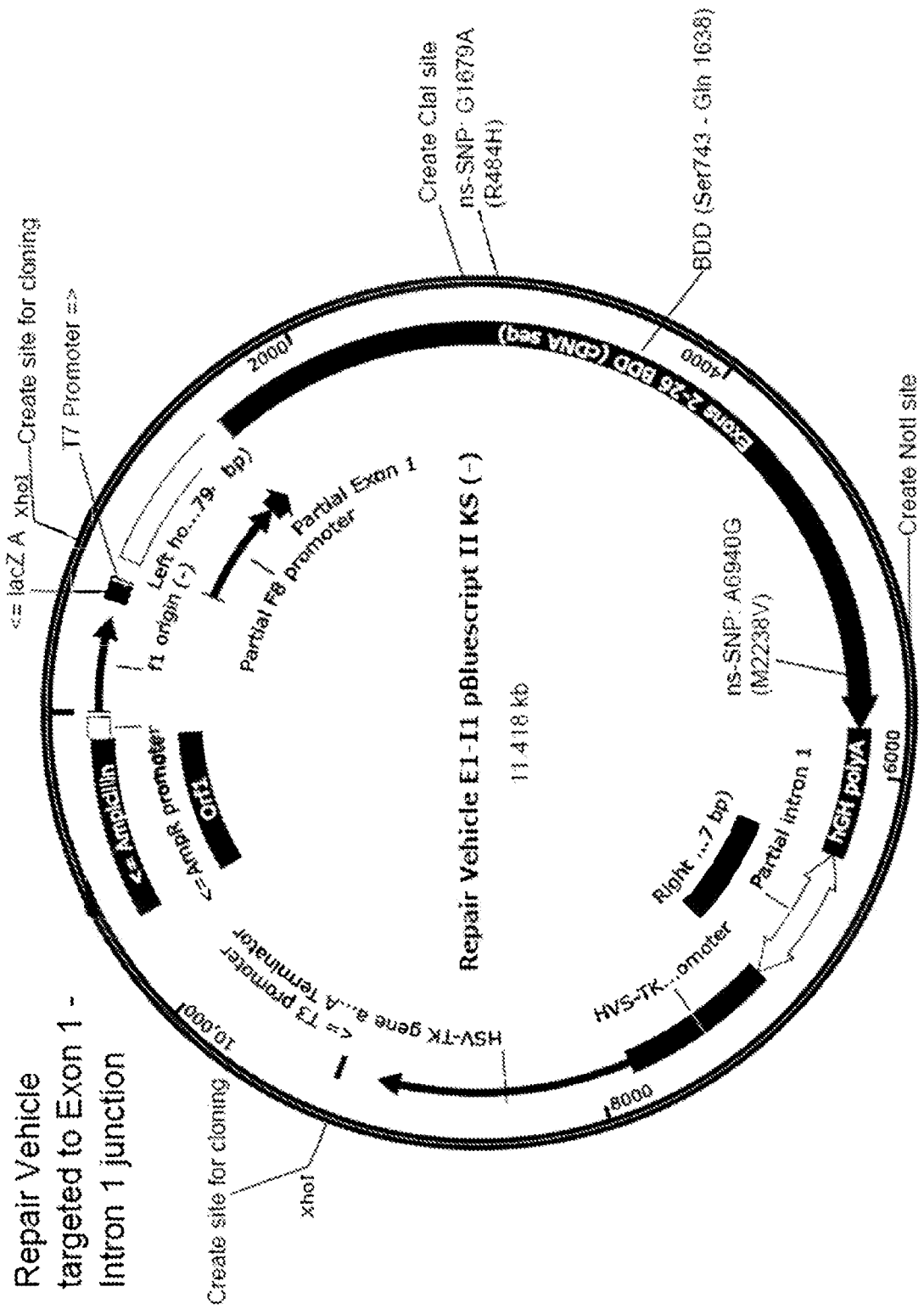
FIG. 10 illustrates the donor plasmid targeting the F8 Exon1/Intron1 junction using a TALEN nuclease, zinc finger nuclease, or cas nuclease approach.

FIG. 10 illustrates an example of a donor plasmid that may be used to repair the F8 gene using a TALEN nuclease, zinc finger nuclease, or cas nuclease approach. The donor plasmid contains the cDNA sequence for exons 2-26 of the F8 gene flanked by two regions of homology to the F8 gene. The left homology region contains a DNA sequence that is homologous to part of the F8 promoter and part of Exon 1. The right homology region contains a DNA sequence that is homologous to part of intron 1. Upon successful homologous recombination into the F8 gene, the integrated construct expresses the resulting mRNA encoding the wild-type (corrected) version of the F8 protein. The donor sequence is cloned into plasmid (p)BlueScript-II KS-minus (pBS-II-KS [−]). The donor plasmid is used with a TALEN, ZFN, or CRISPR/Cas genomic editing strategy. The sequence of the plasmid depicted in FIG. 10 is listed as Seq. ID. No. 13. The annotation of Seq. ID. No. 13 is provided in Table 2 below.

TABLE 2

Repair vehicle targeted to the Exon 1-Intron 1 junction of F8
11418 bp DNA linear

| LOCUS FEATURES | RepairVehicle Location/Qualifiers |
|---|---|
| misc_feature | 21 ... 327 /note="f1 origin (-) " |
| misc_feature | 10430 ... 11290 /note="<= Ampicillin" |
| misc_feature | 471 ... 614 /label=<= lacZ A |
| misc_feature | 626 ... 644 /note="T7 promoter =>" |
| misc_feature | 9229 ... 9248 /note="<= T3 promoter" |
| misc_feature | 10430 ... 11290 /note="<= Orf1" |
| misc_feature | 11332 ... 11360 /note="<= AmpR promoter" |
| misc_feature | 658 ... 740 /note="MCS" |
| misc_feature | 5780 ... 6405 /note="hGH polyA" |
| misc_feature | 7073 ... 7825 /note="HSV-TK promoter " |
| misc_feature | 7826 ... 9211 /note="HSV-TK gene and TK pA Terminator " |
| misc_feature | 740 ... 745 /note="Create site for cloning" |
| misc_feature | 1540 ... 5770 /note="Exons 2-26 BDD (cDNA seq) " |
| misc_feature | 2664 ... 2669 /note="Create ClaI site" |
| misc_feature | 2903 ... 2905 /note="ns-SNP: G1679A (R484H) " |
| misc_feature | 3680 ... 3685 /note="BDD (Ser743 - Gln1638) " |
| misc_feature | 5428 ... 5435 /note="Crete NotI site" |
| misc_feature | 5768 ... 5768 /dnas_title="Stop" /vntifkey="21" /label=Stop |
| misc_feature | 5483 ... 5485 /note="ns-SNP: A6940G (M2238V) " |
| insertion_seq | 3934 ... 5770 /dnas_title="Tg" /vntifkey="14" /label=Tg |
| misc_feature | 9212 ... 9217 /note="Create site for cloning" |
| misc_feature | 9212 ... 9212 /note="MCS" |
| misc_feature | 746 ... 1539 /note="Left homolgy arm (794bp) " |
| misc_feature | 746 ... 1237 /note="Partial F8 promoter" |
| misc_feature | 1238 ... 1539 /note="Partial Exon 1" |
| misc_feature | 6406 ... 7072 /note="Right homology arm (667 bp) " |
| misc_feature | 6406 ... 7072 /note="Partial intron 1" |
| source | 1 ... 11418 /dnas_title="RepairVehicle E1-I1 pBluecript" |

Figure 11:
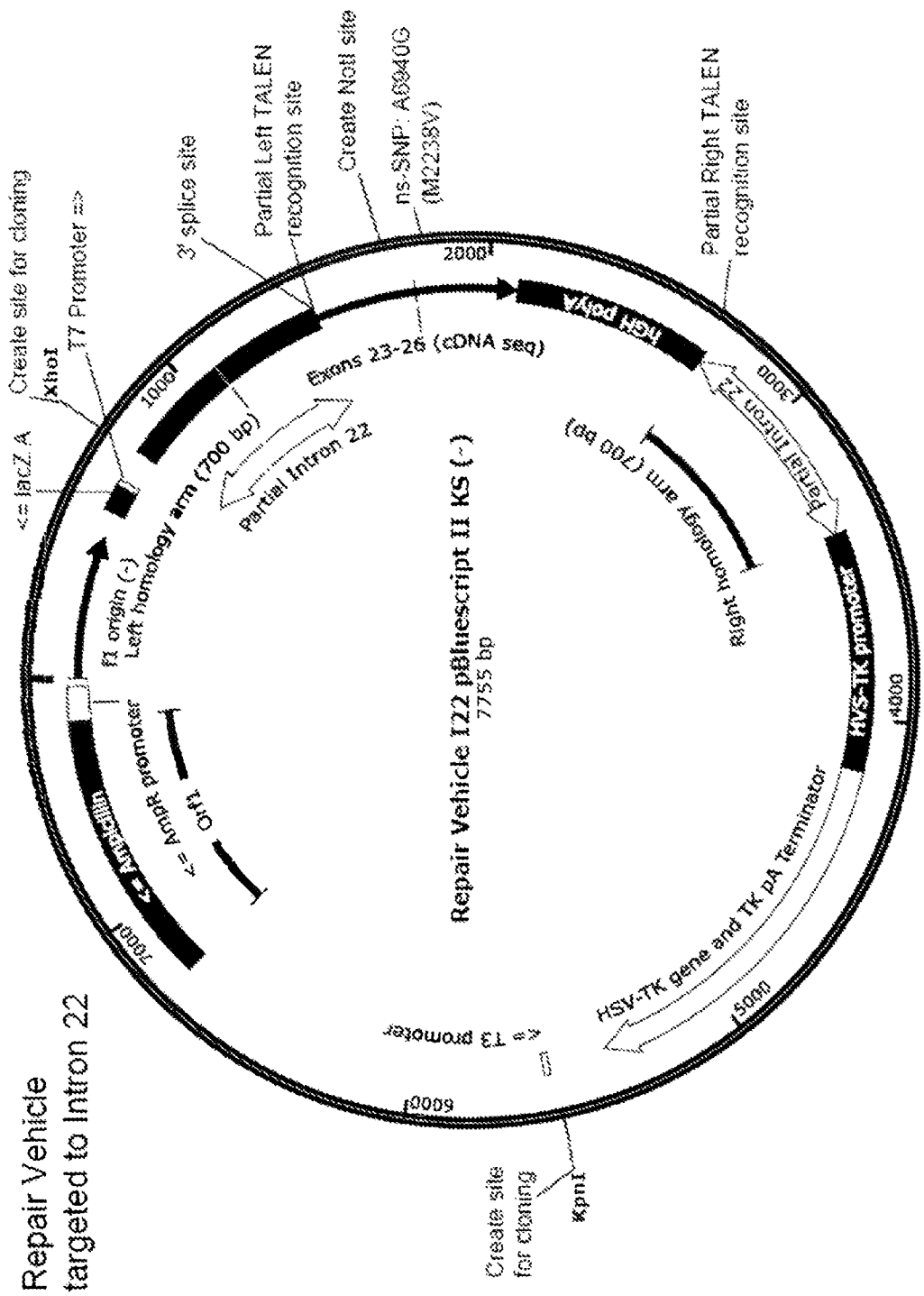
FIG. 11 illustrates the donor plasmid targeting the F8 Intron 22 region using a TALEN nuclease, zinc finger nuclease, or cas nuclease approach.

FIG. 11 illustrates an example of a donor plasmid that is used to repair the F8 gene in intron 22 using a TALEN nuclease, zinc finger nuclease, or cas nuclease approach. The donor plasmid contains a 3' splice site, the cDNA sequence for exons 23-26 of the F8 gene, and a polyadenylation signal sequence flanked by two regions of homology to the F8 gene. The left homology region contains a DNA sequence (approximately 700 base pairs) that is homologous to part of Intron 22 of the FR gene. The right homology region contains a DNA sequence (approximately 700 base pairs) that is homologous to part of intron 22 of the F8 gene. Upon successful homologous recombination into the F8 locus, the integrated construct expresses the resulting mRNA encoding the wild-type (corrected) version of the F8 protein. The sequence of the plasmid depicted in FIG. 11 is listed as Seq. ID. No. 14. The annotation of Seq. ID. No. 14 is provided in Table 3 below.

TABLE 3

Repair vehicle targeted to Intron 22 of F8
7755 bp DNA linear

| LOCUS FEATURES | RepairVehicle Location/Qualifiers |
|---|---|
| misc_feature | 21 ... 327 /note="f1 origin (-) " |
| misc_feature | 6767 ... 7627 /note="<= Ampicillin" |
| misc_feature | 471 ... 614 /label=<= lacZ A |
| misc_feature | 626 ... 644 /note="T7 promoter =>" |
| misc_feature | 5566 ... 5585 /note="T3 promoter =>" |
| misc_feature | 6767 ... 7627 /note="<= Orf1" |
| misc_feature | 7669 ... 7697 /note="<= AmpR promoter" |
| misc_feature | 658 ... 740 /note="MCS" |
| misc_feature | 1440 ... 2074 /note="Exons 23-26 (cDNA seq) " |
| misc_feature | 1732 ... 1739 /note="Create NotI site" |
| misc_feature | 2084 ... 2709 /note="hGH polyA" |
| misc_feature | 1787 ... 1789 /note="ns-SNP: A6940G (M2238V) " |
| misc_feature | 3410 ... 4162 /note="HSV-TK promoter " |
| misc_feature | 4163 ... 5548 /note="HSV-TK gene and TK pA Terminator " |
| misc_feature | 741 ... 745 /note="Create site for cloning" |
| misc_feature | 5549 ... 5553 /note="Create site for cloning" |
| misc_feature | 746 ... 1445 /note="Left homolgy arm (700 bp) " |
| misc_feature | 1437 ... 1445 /note="Partial Left TALEN recognition site" |
| misc_feature | 2710 ... 3409 /note="Right homology arm (700 bp) " |
| misc_feature | 2710 ... 2719 /note="Partial Right TALEN recognition site" |
| misc_feature | 746 ... 1445 /note="Partial Intron 22" |
| misc_feature | 2710 ... 3409 /note="Partial Intron 22" |
| misc_feature | 1446 ... 1447 /note="3' spice site" |
| source | 1 ... 7755 /dnas_title="RepairVehicle I22 pBluecript" |

Figure 12:
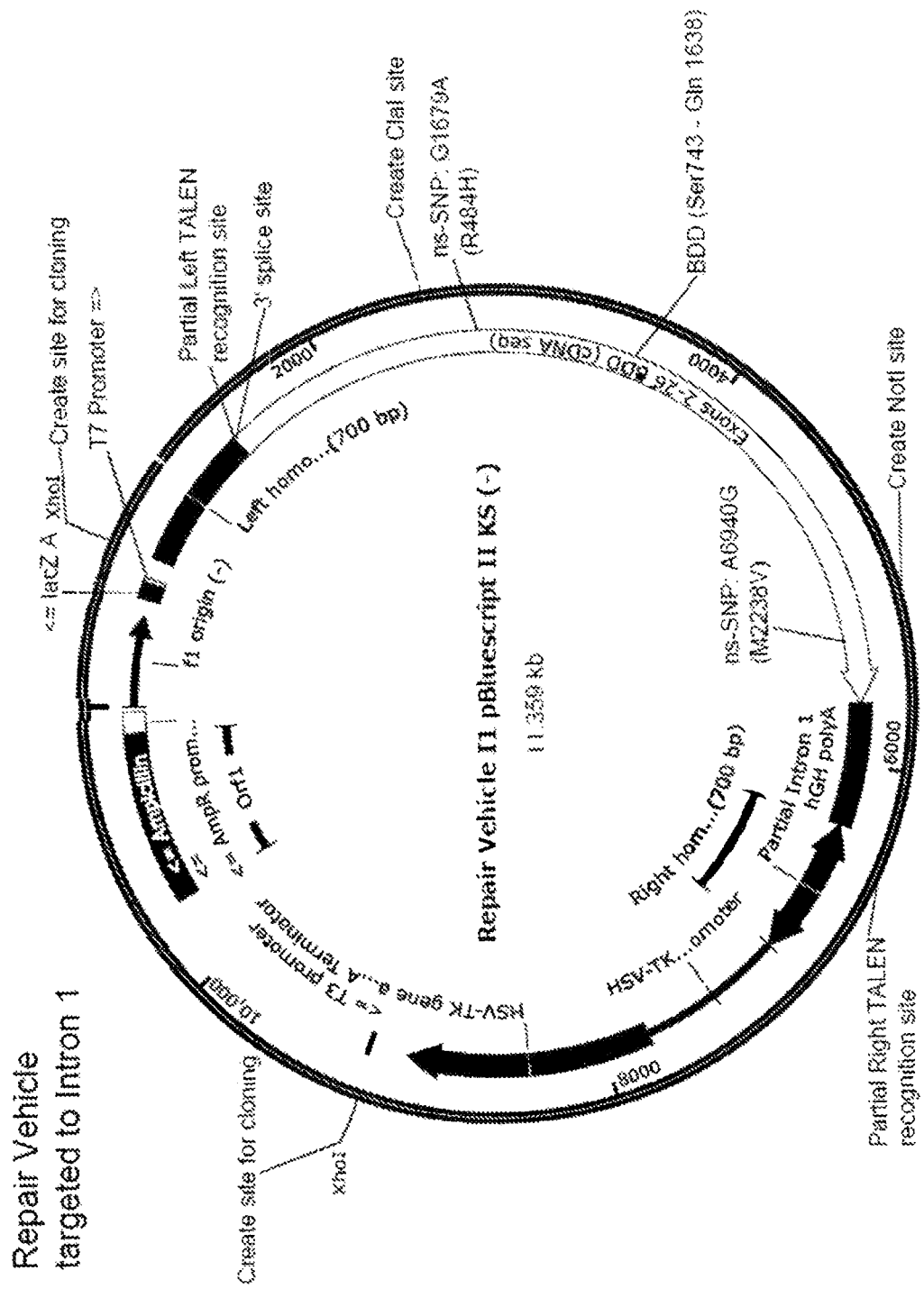
FIG. 12 illustrates the donor plasmid targeting the F8 Intron 1 region using a TALEN nuclease, zinc finger nuclease, or cas nuclease approach.

FIG. 12 illustrates an example of a donor plasmid that is used to repair the F8 gene in intron1 using a TALEN nuclease, zinc finger nuclease, or cas nuclease approach. The donor plasmid contains a 3' splice site, the cDNA sequence of the F8 gene for exons 2-26 lacking the B-domain (B-domain deleted (BDD) version of the F8 gene), and a polyadenylation signal sequence flanked by two regions of homology to the F8 gene. The left homology region contains a DNA sequence (approximately 700 base pairs) that is homologous to part of Exon 1 and Intron 1 of the F8 gene. The right homology region contains a DNA sequence (approximately 700 base pairs) that is homologous to part of intron 1 of the F8 gene. Upon successful homologous recombination into the F8 locus, the integrated construct expresses the resulting mRNA encoding the wild-type (corrected) version of the F8 protein. The sequence of the plasmid depicted in FIG. 12 is listed as Seq. ID. No. 15. The annotation of Seq. ID. No. 15 is provided in Table 4 below.

TABLE 4

Repair vehicle targeted to Intron 1 of F8
11359 bp DNA linear

| LOCUS FEATURES | RepairVehicle Location/Qualifiers |
|---|---|
| misc_feature | 21 ... 327 /note="f1 origin (-) " |
| misc_feature | 10371 ... 11231 /note="<= Ampicillin" |
| misc_feature | 471 ... 614 /label=<= lacZ A |
| misc_feature | 626 ... 644 /note="T7 promoter =>" |
| misc_feature | 9170 ... 9189 /note="<= T3 promoter" |
| misc_feature | 10371 ... 11231 /note="<= Orf1" |
| misc_feature | 11273 ... 11301 /note="<= AmpR promoter" |
| misc_feature | 658 ... 740 /note="MCS" |
| misc_feature | 874 ... 1187 /note="Exon 1" |
| misc_feature | 1436 ... 1445 /note="Partial Left TALEN recognition site" |
| misc_feature | 5688 ... 6313 /note="hGH polyA" |
| misc_feature | 6314 ... 7013 /note="Right homology arm (700 bp) " |
| misc_feature | 6314 ... 6322 /note="Partial Right TALEN recognition site" |
| misc_feature | 7014 ... 7766 /note="HSV-TK promoter " |
| misc_feature | 7767 ... 9152 /note="HSV-TK gene and TK pA Terminator " |
| misc_feature | 746 ... 1445 /note="Left homology arm (700 bp) " |
| misc_feature | 746 ... 873 /note="Partial F8 promoter" |
| misc_feature | 740 ... 745 /note="Create site for cloning" |
| misc_feature | 6314 ... 7013 /note="Partial Intron 1" |
| misc_feature | 1448 ... 5678 /note="Exons 2-26 BDD (cDNA seq) " |
| misc_feature | 1446 ... 1447 /note="3' spice site" |
| misc_feature | 2572 ... 2577 /note="Create ClaI site" |
| misc_feature | 2811 ... 2813 /note="ns-SNP: G1679A (R484H) " |
| misc_feature | 3588 ... 3593 /note="BDD (Ser743 - Gln1638) " |
| misc_feature | 5336 ... 5343 /note="Create NotI site" |
| misc_feature | 5676 ... 5676 /dnas_title="Stop" /vntifkey="21" /label=Stop |
| misc_feature | 5391 ... 5393 /note="ns-SNP: A6940G (M2238V) " |
| insertion_seq | 3842 ... 5678 /dnas_title="Tg" /vntifkey="14" /label=Tg |
| misc_feature | 9153 ... 9158 /note="Create site for cloning" |
| misc_feature | 9153 ... 9153 /note="MCS" |
| source | 1 ... 11359 /dnas_title="RepairVehicle I1 pBluescript " |

In one embodiment, the integration matrix component for each of these distinct homologous donor plasmid is either a cDNA that is linked to the immediately upstream exon or a cDNA that has a functional 3'-intron-splice-junction so that the cDNA sequence is linked through the RNA intermediate following removal of the intron. In one embodiment, the donor plasmid is personalized, on an individual basis, so that each patient's gene that is repaired expresses the form of the FVIII protein that they are maximally tolerant of.

Zinc Finger Nucleases (ZFNs)

Engineered nucleases have emerged as powerful tools for site specific editing of the genome. For example, zinc finger nucleases (ZFNs) are hybrid proteins containing the zinc-finger DNA-binding domain present in transcription factors and the non-specific cleavage domain of the endonuclease Fok1. (Li et al., In vivo genome editing restores haemostasis in a mouse model of haemophilia, Nature 2011 Jun. 26; 475(7355):217-21).

The same sequences targeted by the TALEN approach, discussed above, can also be targeted by the zinc finger nuclease approach for genome editing. Zinc finger nucleases (ZFNs) are a class of engineered DNA-binding proteins that facilitate targeted editing of the genome by creating double-strand breaks in DNA at user-specified locations. Each Zinc Finger Nuclease (ZFN) consists of two functional domains: 1) a DNA-binding domain comprised of a chain of two-finger modules, each recognizing a unique hexamer (6 bp) sequence of DNA, wherein two-finger modules are stitched together to form a Zinc Finger Protein, each with specificity of >24 bp, and 2) a DNA-cleaving domain comprised of the nuclease domain of Fok 1. The DNA-binding and DNA-cleaving domains are fused together and recognize the targeted genomic sequences, allowing the Fok1 domains to form a heterodimeric enzyme that cleaves the DNA by creating double stranded breaks.

Zinc finger nucleases can be readily made by using techniques known in the art (Wright D A, et al. Standardized reagents and protocols for engineering zinc finger nucleases by modular assembly. Nat Protoc. 2006; 1(3):1637-52). Engineered zinc finger nucleases can stimulate gene targeting at specific genomic loci in animal and human cells. The construction of artificial zinc finger arrays using modular assembly has been described. The archive of plasmids encoding more than 140 well-characterized zinc finger modules together with complementary web-based software for identifying potential zinc finger target sites in a gene of interest has also been described. These reagents enable easy mixing-and-matching of modules and transfer of assembled arrays to expression vectors without the need for specialized knowledge of zinc finger sequences or complicated oligonucleotide design (Wright D A, et al. Standardized reagents and protocols for engineering zinc finger nucleases by modular assembly. Nat Protoc. 2006; 1(3):1637-52). Any gene in any organism can be targeted with a properly designed pair of ZFNs. Zinc-finger recognition depends only on a match to the target DNA sequence (Carroll, D. Genome engineering with zinc-finger nucleases. Genetics Society of America, 2011, 0.188(4), pp 773-782).

Clustered Regularly Interspaced Short Palindromic Repeats (CRISPR) and CRISPR Associated (Cas) Nucleuses In addition to the current protein-based targeting methods (TALEN and Zinc Finger) useful for gene targeting, there is another system for genome editing that uses a short RNA to guide a nuclease to the DNA target. This system is called the CRISPR technology. (Mali P, Yang L, Esvelt K M, Aach J, Guell M, DiCarlo J E, Norville J E, Church G M. RNA-guided human genome engineering via Cas9. Science. 2013 Feb. 15; 339(6121):823-6; Gasiunas G, Barrangou R, Horvath P, Siksnys V. Cas9-crRNA ribonucleoprotein complex mediates specific DNA cleavage for adaptive immunity in bacteria. Proc Natl Acad Sci USA. 2012 Sep. 25; 109(39): E2579-86. Epub 2012 Sep. 4).

The Clustered Regularly Interspaced Short Palindromic Repeats (CRISPR) and CRISPR. Associated (Cas) system was discovered in bacteria and functions as a defense against foreign DNA, either viral or plasmid. In bacteria, the endogenous CRISPR/Cas system targets foreign DNA with a short, complementary single-stranded RNA (CRISPR RNA or crRNA) that localizes the Cas9 nuclease to the target DNA sequence. The DNA target sequence can be on a plasmid or integrated into the bacterial genome. The crRNA can bind on either strand of DNA and the Cas9 cleaves both strands (double strand break, DSB). A recent in vitro reconstitution of the *Streptococcus pyogenes* type II CRISPR system demonstrated that crRNA fused to a normally trans-encoded tracrRNA is sufficient to direct Cas9 protein to sequence-specifically cleave target DNA sequences matching the crRNA. The fully defined nature of this two-component system allows it to function in the cells of eukaryotic organisms such as yeast, plants, and even mammals. By cleaving genomic sequences targeted by RNA sequences, such a system greatly enhances the ease of genome engineering.

The crRNA targeting sequences are transcribed from DNA sequences known as protospacers. Protospacers are clustered in the bacterial genome in a group called a CRISPR array. The protospacers are short sequences (~20 bp) of known foreign DNA separated by a short palindromic repeat and kept like a record against future encounters. To create the CRISPR targeting RNA (crRNA), the array is transcribed and the RNA is processed to separate the individual recognition sequences between the repeats. In the Type II system, the processing of the CRISPR array transcript (pre-crRNA) into individual crRNAs is dependent on the presence of a trans-activating crRNA (tracrRNA) that has sequence complementary to the palindromic repeat. When the tracrRNA hybridizes to the short palindromic repeat, it triggers processing by the bacterial double-stranded RNA-specific ribonuclease, RNase III. Any crRNA and the tracrRNA can then both bind to the Cas9 nuclease, which then becomes activated and specific to the DNA sequence complimentary to the crRNA. (Mali P, Yang L, Esvelt K M, Aach J, Guell M, DiCarlo J E, Norville J E, Church G M. RNA-guided human genome engineering via Cas9. Science. 2013 Feb. 15; 339(6121):823-6; Gasiunas G, Barrangou R, Horvath P, Siksnys V. Cas9-crRNA ribonucleoprotein complex mediates specific DNA cleavage for adaptive immunity in bacteria. Proc Natl Acad Sci USA. 2012 Sep. 25; 109(39):E2579-86. Epub 2012 Sep. 4).

The double-strand DNA breakages (DSDB) induced by the TALEN approach overlaps with the 6 distinct sites of DSDB induced by Cas9, via targeting by 6 distinct CRISPR-guide RNAs [F8-CRISPR/Cas9-1 (F8-Ex1/Int1), F8-CRISPR/Cas9-2 (F8-Int1), F8-CRISPR/Cas9-3 (F8-Ex14/Int14), F8-CRISPR/Cas9-4 (F8-Int14), F8-CRISPR/Cas9-5 (F8-Ex22/Int22), F8-CRISPR/Cas9-6 (F8-Int22)]. This allows use of the same 6 distinct homologous donor sequences with all three genome editing approaches, including the TALEN nuclease, the zinc finger nuclease (ZFN), and the CRISPR-associated (Cas) nuclease.

Figure 13:
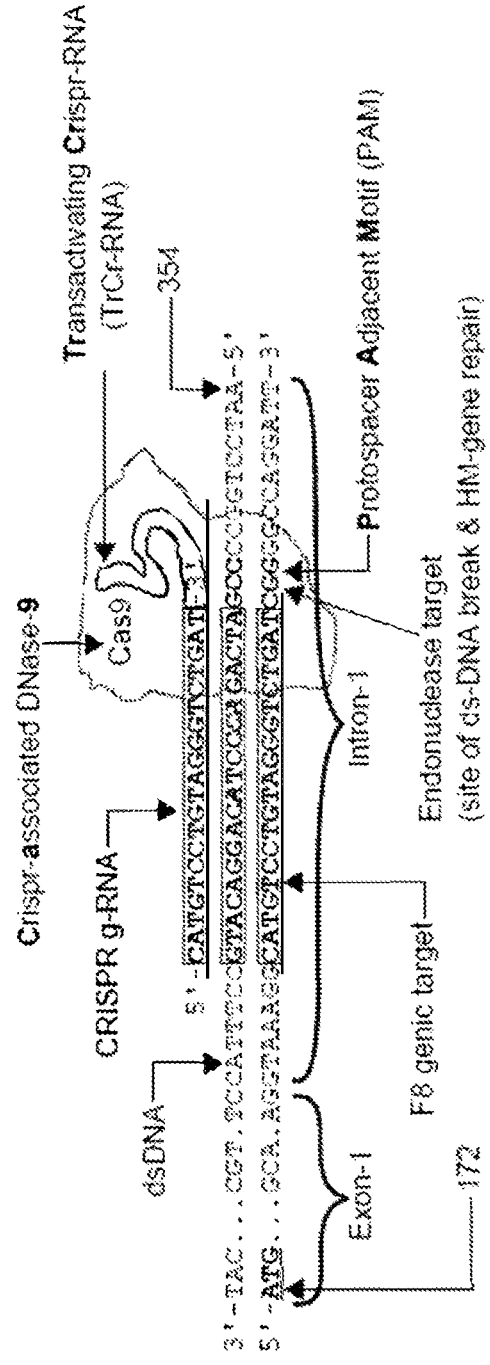
FIG. 13 illustrates the CRISPR/Cas9-mediated F8 repair strategy targeting intron 1.

FIG. 13 illustrates a CRISPR/Cas9-mediated strategy to repair the human Factor VIII (FVIII) gene (FS) mutations in ~95% of all patients with severe hemophilia-A (HA), including the highly recurrent intron-1 (I1)-inversion (I1I)-mutation as well as the intron-22 (I22)-inversion (I22I)-mutation. FIG. 13 shows the specific F8 genomic DNA sequence (spanning genic base positions 172-354 at intron 1) within which a double-stranded (ds)-DNA break is introduced (designated "Endonuclease target" in this panel) by this strategy's wild-type (wt) CRISPR/Cas9 ds-DNase in which both of its endonuclease domains are catalytically functional ("hF8-CRISPR/Cas9 wt-1"). This panel also shows important orienting landmarks, including the following: (i) Nucleotide coordinates of this region (based on the February 2009, human genome assembly [UCSC Genome Browser: http://genome.ucsc.edu/]) are numbered with respect to the wild-type F8 transcription unit, where the initial (5'-most) base of the F8 pre-mRNA (5'-base of exon-1 [E1]) is designated +1 or 1 (note that this base corresponds to X-chromosome position 154,250,998) and include the appropriate intronic sequence bases in calculating the genomic base positioning; (ii) Relative location of the X-chromosome's centromere (X-Cen) and its long-arm telomere (Xq-Tel), as transcription of the wild-type F8 locus and all of its mutant alleles causing HA—with the exception of its two recurrent intronic inversions, the 1- and the I22I-mutations—is oriented towards X-Cen. Transcription of the I1- and I22-inverted F8 loci, in contrast, are oriented towards Xq-Tel. This strategy repairs (i) the highly recurrent I22I-mutation—also designated $F8_{I22I}$—which causes ~45% of all unrelated patients with severe hemophilia-A (HA) and (ii) mutant F8 loci in ~90-95% of all other patients with severe HA, who are either known or found to have any one of the >1.500 distinct mutations that have been found (according to the HAMSTeRS database of HA-causing F8 mutations) thus far to reside down-stream (i.e., 3') of exon-1 (E1). The last codon of E1 partially encodes the translated residue 48 (29 in the mature FVIII protein secreted into plasma). Most mutations repaired are "previously known" (literature and/or HIAMSTeRS or other databases). Some have never been identified previously. These F8 abnormalities in this latter category are "private" (found only in this particular) to the patient/family. Finally, FIG. 13 shows the functional aspects of hF8-CRISPR/Cas9 wt-1 including the overall DNA-binding domain of the CRISPR-associated guide (g)RNA as well as the (i) Protospacer adjacent motif (PAM), which is the site at which the DNase function of Cas9 introduces the ds-DNA break (DSDB); and (ii) The Transactivating Crispr-RNA (TrCr-RNA), which is covalently attached the gRNA as is what brings the Cas9 endonuclease to the genomic DNA target for digestion. The introduction of a DSDB in the presence of a homologous repair vehicle, results in the in-frame integration, immediately 3' to E1, of one of either two partial human F8 cDNAs comprising either (i) exons 2-25 and the protein coding sequence, or CDS, of exon 26 (designated hF8[E2-E25/E26$_{CDS}$]), which effects repair of the F8 gene such that it now encodes a full-length wild-type FVIII protein; or (ii) Exons 2-13 entirely linked next to the very 5'-most end of exon-14 (E14), which in turn is linked covalently to the very 3'-most end of E14 (i.e., a B-domain-deleted [BDD]-F8 cDNA), which is then covalently linked to Exons 15-25 entirely, and then the protein coding sequence, or CDS, of exon 26 (designated hF8[E2-E13/E14-BDD/E15-E25/E26$_{CDS}$]), which effects repair of the F8 gene such that it now encodes a BDD-engineered FVIII protein, which is fully functional in FVIII:C activity. The homologous repair vehicle is selected to have a F8 cDNA with the appropriate alleles at all ns-SNP sites so that the patient can receive a "matched" gene repair or at least a least mismatched repair.

The left homology arm of the homologous repair vehicle for Homologous Repair Vehicle No. 1 (HRV1) for hF8-CRISP/Cas9 wt-1 is listed as Seq. ID. No. 17 and comprises the first 1114 bases of the human F8 genomic DNA (which is shown here as single-stranded and representing the sense strand) and contains 800 bp of the immediately 5'-promoter region of the human F8 gene and all 314 bp of the F8 exon-1 (E1), including its 171 bp 5'-UTR and its 143 bp of protein (en)coding sequence (CDS). The actual left homologous arm (LHA) of the homologous repair vehicle (HRV1), which is used for this CRISPR/Cas9-mediated F8 gene repair (that occurs at the E1/intron-1 [I1] junction of a given patient's endogenous mutant F8), contains at least 500 bp of this genomic DNA sequence (i.e., from it's very 3'-end, which corresponds to the second base of the codon for translated residue 48 of the wild-type FVIII protein and residue 29 of the mature FVIII protein found in the circulation) and could include it all, if, for example, we find that full-length F8 gene repair can be effected efficiently in the future. In this instance, the integration matrix would then follow the LHA of this HRV1, and be covalently attached to it, and this integration matrix contains (in-frame with each other and with the 3'-end of the patient's native exon-1, which is utilized in situ, along with his native F8 promoter, to regulate expression of the repaired F8 gene), all of F8 exons 2-25, and the protein CDS of exon-25, followed by the functional mRNA 3'-end forming signals of the human growth hormone gene (hGH-pA). The F8 cDNA from exons 2-25 and the CDS of exon-26 to be used in the homologous repair vehicle is listed as Seq. ID. No. 18 and follows the left homology arm, and in this example represents the haplotype (H)3 encoding wild-type variant of F5, which can be used to cure, for example, patients with the I1I-mutation and the I22I-mutation, that arose on an H3-background haplotype. This following protein encoding cDNA sequence contains 6,909 bp of the entire 7,053 bp of F8 protein encoding sequence (i.e., the first 144 bp of protein CDS from FVIII, from its initiator methionine, is not shown, as this is contained in exon-1, which is provided by the patient's own endogenous exon-1, providing it is not mutant and thus precluding the repair event). The right homology arm of the homologous repair vehicle for the cas nuclease approach is listed as Seq. ID. No. 19 and includes 1109 bases of human F8 genomic DNA (which is shown here as single-stranded and representing the sense strand) from the F8 gene intron 1.

4. Replacement Sequence

As described above, following the introduction of the targeting nuclease into the cell, the nuclease, upon dimerization, catalyzes a double stranded break in the DNA between their binding sites. If a double stranded break occurs in the presence of, for example, a donor plasmid (DP), which contains a stretch of DNA with a left homology (HL) and right homology (HR) arm that have identical DNA sequences to that in the native chromosomal DNA 5' and 3' of the region flanking the break-point, homologous recombination occurs very efficiently. Accordingly, the present invention includes the introduction of a nucleic acid sequence that serves as a donor sequence during homologous recombination which includes a partial F8 gene that replaces, and thus repairs, the mutated portion of the subject's F8 gene.

The donor sequence nucleic acid comprises (i) a nucleic acid encoding a truncated FVIII polypeptide or (ii) a native F8 3' splice acceptor site operably linked to a nucleic acid encoding a truncated FVIII polypeptide that contains a non-mutated portion of the FVIII protein. The donor sequence is flanked on each side by regions of nucleic acid which are homologous to the F8 gene. Each of these homologous regions can include about 20, 50, 75, 100, 200, 300, 400, 500, 600, 700, 800, 900, 1000 or more nucleotides homologous with the subject's F8 gene. In embodiments, each of the homologous regions flanking the donor sequence is between about 200 to about 1,200 nucleotides, between 400 and about 1000 nucleotides, or between about 600 and about 900 nucleotides. In one embodiment, each homologous region is between about 800 and about 900 nucleotides. Thus, each donor sequence nucleic acid includes a donor sequence replacing an endogenous mutation in the subject's F8 gene, and 5' and 3' flanking sequences which are homologous to the F8 gene.

The donor sequence is derived based on the specific mutation within the subject's F8 gene targeted for replacement and repair. Accordingly, the length of the donor sequence can vary. For example, when repairing a point mutation, the donor sequence can include only a small number of replacement nucleotide sequences compared with, for example, a donor sequence derived for repairing an inversion such as an intron 22 inversion. Therefore, a donor sequence can be of any length, for example between 2 and 10,000 nucleotides in length (or any integer value there between or there above), preferably between about 100 and 1,000 nucleotides in length (or any integer there between), more preferably between about 200 and 500 nucleotides in length. The designing of donor sequence nucleic acids is known in the art, for example, see Cermak et al., Efficient design and assembly of custom TALEN and other TAL effector-bused constructs for DNA targeting, Nucleic Acid Res. 2011 Sep. 1; 39 (17):7879.

In one embodiment of the present invention, the gene mutation targeted for repair is a point mutation, and the donor sequence includes a nucleic acid sequence that replaces the point mutation with a sequence that does not include the point mutation, for example, the wild-type F8 sequence. In one embodiment, the gene mutation targeted for repair is a deletion and the donor sequence includes a nucleic acid sequence that replaces the deletion with a sequence that does not include the deletion, for example, the wild-type F8 sequence.

In one embodiment, the gene mutation targeted for repair is an inversion, and the donor sequence includes a nucleic acid sequence that encodes a truncated FVIII polypeptide that, upon insertion into the F8 genome, repairs the inversion and provides for the production of a functional FVIII protein. In one embodiment, the gene mutation targeted for repair is an inversion of intron 1. In one embodiment, the gene mutation targeted for repair is an inversion of intron 22, and the donor sequence includes a nucleic acid that encodes all of exons 23-25 and the coding sequence of exon-26.

In any of the methods described herein, the donor sequence can contain sequences that are homologous, but not identical (for example, contain nucleic acid sequence encoding wild-type amino acids or differing ns-SNP amino acids), to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to about 99% sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs, or any number of base pairs greater than 1,000, that are homologous or identical to sequences in the region of interest. In other embodiments, the donor sequence is non-homologous to the first sequence, and is inserted into the genome by non-homologous recombination mechanisms.

5. Targeted Cells

The gene targeting and repair approaches using the different nucleases described above can be carried out using many different target cells. For example, the transduced cells may include endothelial cells, hepatocytes, or stem cells. In one embodiment, the cells can be targeted in vivo. In one embodiment, the cells can be targeted using ex vivo approaches and reintroduced into the subject.

BOECs

In one embodiment, the target cells from the subject are endothelial cells. In one embodiment, the endothelial cells are blood outgrowth endothelial cells (BOECs). Characteristics that render BOECs attractive for gene repair and delivery include the: (i) ability to be expanded from progenitor cells isolated from blood, (ii) mature endothelial cell, stable, phenotype and normal senescence (~65 divisions), (iii) prolific expansion from a single blood sample to 1019 BOECs, (iv) resilience, which unlike other endothelial cells, permits cryopreservation and hence multiple doses for a single patient prepared from a single isolation. Methods of isolation of BOECs are known, where the culture of peripheral blood provides a rich supply of autologous, highly proliferative endothelial cells, also referred to as blood outgrowth endothelial cells (BOECs). Bodempudi V, et al., Blood outgrowth endothelial cell-based systemic delivery of antiangiogenic gene therapy for solid tumors. Cancer Gene Ther. 2010 Doc; 17(12):855-63.

Studies in animal models have revealed properties of blood outgrowth endothelial cells that indicate that they are suitable for use in ex vivo gene repair strategies. For example, a key finding concerning the behavior of canine blood outgrowth endothelial cells (cBOECs) is that cBOECs persist and expand within the canine liver after infusion. Milbauer L C, et al. Blood outgrowth endothelial cell migration and trapping in vivo: a window into gene therapy. 2009 April; 153(4):179-89. Whole blood clotting time (WBCT) in the HA model was also improved after administration of engineered cBOECs. WBCT dropped from a pretreatment value of under 60 min to below 40 min and sometimes below 30 min. Milbauer L C, et al., Blood outgrowth endothelial cell migration and trapping in vivo: a window into gene therapy. 2009 April; 153(4):179-89.

LSECs

In one embodiment, the target cells from the subject are hepatocytes. In one embodiment, the cell is a liver sinusoidal endothelial cell (LSECs). Liver sinusoidal endothelial cells (LSEC) are specialized endothelial cells that play important roles in liver physiology and disease. Hepatocytes and liver sinusoidal endothelial cells (LSECs) are thought to contribute a substantial component of FVIII in circulation, with a variety of extra-hepatic endothelial cells supplementing the supply of FVIII.

In one embodiment, the present invention targets LSEC cells, as LSEC cells likely represent the main cell source of FVIII. Shahani, T, et al., Activation of human endothelial cells from specific vascular beds induces the release of a FVIII storage pool. Blood 2010; 115(23):4902-4909. In addition, LSECs are believed to play a role in induction of immune tolerance. Onoe, T, et al., Liver sinusoidal endothelial cells tolerize T cells across MHC barriers in mice. J Immunol 2005; 175(1):139-146. Methods of isolation of LSECs are known in the art. Karrar, A, et al., Human liver sinusoidal endothelial cells induce apoptosis in activated T cells: a role in tolerance induction. Out. 2007 February; 56(2): 243-252.

iPSCs

In one embodiment, the transduced cells from the subject are stem cells. In one embodiment, the stem cells are induced pluripotent stem cells (iPSCs). Induced pluripotent stem cells (iPSCs) are a type of pluripotent stem cell artificially derived from a non-pluripotent cell, typically an adult somatic cell, by inducing expression of specific genes and factors important for maintaining the defining properties of embryonic stem cells. Induced pluripotent stem cells (iPSCs) have been shown in several examples to be capable of site specific gene targeting by nucleases. Ru, R. et al. Targeted genome engineering in human induced pluripotent stem cells by penetrating TALENs. Cell Regeneration. 2013, 2:5; Sun N, Zhao H. Seamless correction of the sickle cell disease mutation of the HBB gene in human induced pluripotent stem cells using TALENs. Biotechnol Bioeng. 2013 Aug. 8. Induced pluripotent stem cells (iPSCs) can be isolated using methods known in the art. Lorenzo, I M. Generation of Mouse and Human Induced Pluripotent Stem Cells (iPSC) from Primary Somatic Cells. Stem Cell Rev. 2013 August; 9(4):435-50.

Co-Cultured Cells

As discussed above, a number of different cells types may be targeted for repair. However, pure populations of some cell types may not promote sufficient homing and implantation upon reintroduction to provide extended and sufficient expression of the corrected F8 gene. Therefore, some cell types may be co-cultured with different cell types to help promote cell properties (i.e. ability of cells to engraft in the liver).

In one embodiment, the transduced cells are from blood outgrowth endothelial cells (BOECs) that have been co-cultured with additional cell types. In one embodiment, the transduced cells are from blood outgrowth endothelial cells (BOECs) that have been co-cultured with hepatocytes or liver sinusoidal endothelial cell (LESCs) or both. In one embodiment, the transduced cells are from blood outgrowth endothelial cells (BOECs) that have been co-cultured with induced pluripotent stem cells (iPSCs).

6. Cell Delivery

Methods of nucleic acid delivery are well known in the art. (See, e.g., WO 2012051343). In the methods provided herein, the described nuclease encoding nucleic acids can be introduced into the cell as DNA or RNA, single-stranded or double-stranded and can be introduced into a cell in linear or circular form. In one embodiment, the nucleic acids encoding the nuclease are introduced into the cell as mRNA. The donor sequence can introduced into the cell as DNA single-stranded or double-stranded and can be introduced into a cell in linear or circular form. If introduced in linear form, the ends of the nucleic acids can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

The nucleic acids can be introduced into a cell as part of a vector molecule having additional sequences such as, for example, replication origins, promoters and genes encoding antibiotic resistance. Moreover, the nucleic acids can be introduced as naked nucleic acid, as nucleic acid complexed with an agent such as a liposome or poloxamer, or can be delivered by viruses (e.g., adenovirus, AAV, herpesvirus, retrovirus, lentivirus).

The nucleic acids may be delivered in vivo or ex vivo by any suitable means. Methods of delivering nucleic acids are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824.

Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824. Furthermore, any of these vectors may comprise one or more of the sequences needed for treatment. Thus, when one or more nucleic acids are introduced into the cell, the nucleases and/or donor sequence nucleic acids may be carried on the same vector or on different vectors. When multiple vectors are used, each vector can comprise a sequence encoding a TALEN-L monomer, a TALEN-R monomer, or a donor sequence nucleic acid. Alternatively, two or more of the nucleic acids can be contained on a single vector.

Conventional viral and non-viral based gene transfer methods can be used to introduce nucleic acids encoding the nucleic acids in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (RichMar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024.

The preparation of lipid:nucleic acid complexes, including targeted liposomes such as immunolipid complexes, is well known to one of skill in the art (see, e.g., Crystal, Science 270:404-410 (1995); Blaese et al, Cancer Gene Ther. 2:291-297 (1995); Behr et al, Bioconjugate Chem. 5:382-389 (1994); Remy et al, Bioconjugate Chem. 5:647-654 (1994); Gao et al, Gene Therapy 2:710-722 (1995); Ahmad et al, Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) Nature Biotechnology 27(7):643).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cz's-acting long terminal repeats with packaging capacity for up to 6-10 kb of foreign sequence. The minimum cz's-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian immunodeficiency virus (SIV), human immunodeficiency virus (HIV), and combinations thereof (see, e.g., Buchscher et al, J. Virol. 66:2731-2739 (1992); Johann et al, J. Virol. 66:1635-1640 (1992); Sommerfelt et al., Virol. 176:58-59 (1990); Wilson et at, J. Virol. 63:2374-2378 (1989); Miller et al, J. Virol. 65:2220-2224 (1991); PCT US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al, Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors is described in a number of publications, including U.S. Pat. No. 5,173,414; Tratschin et al, Mol Cell. Biol. 5:3251-3260 (1985); Tratschin, et at, Mol. Cell. Biol. 4:2072-2081 (1984); Hermonat & Muzyczka, PNAS 81:6466-6470 (1984); and Samulski et al, J. Virol. 63:03822-3828 (1989).

At least six viral vector approaches are currently available for gene transfer in clinical trials, which utilize approaches that involve complementation of defective vectors by genes inserted into helper cell lines to generate the transducing agent. pLASN and MFG-S are examples of retroviral vectors that have been used in clinical trials (Dunbar et al, Blood 85:3048-305 (1995); Kohn et al, Nat. Med. 1:1017-102 (1995); Malech et al, PNAS 94:22 12133-12138 (1997)). PA317/pLASN was the first therapeutic vector used in a gene therapy trial. (Blaese et al, Science 270:475-480 (1995)). Transduction efficiencies of 50% or greater have been observed for MFG-S packaged vectors. (Ellem et al, Immunol Immunother. 44(1):10-20 (1997); Dranoff et at, Hum. Gene Ther. 1:111-2 (1997). Recombinant adeno-associated virus vectors (rAAV) are an alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al, Lancet 351:9117 1702-3 (1998), Kearns et al, Gene Ther. 9:748-55 (1996)). Other AAV serotypes, including AAV1, AAV2, AAV3, AAV4, AAV5, AAV6, AAV7, AAV8, AAV9 and AAVrh.lO and any novel AAV serotype can also be used in accordance with the present invention. In a particular embodiment, the vector is based on a hepatotropic adeno-associated virus vector, serotype 8 (see, e.g., Nathwani et al., Adeno-associated viral vector mediated gene transfer for hemophilia B, Blood 118(21):4-5, 2011).

Replication-deficient recombinant adenoviral vectors (Ad) can be produced at high titer and readily infect a number of different cell types. Most adenovirus vectors are engineered such that a transgene replaces the Ad El a, El b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al, Hum. Gene Ther. 7:1083-9 (1998)). Additional examples of the use of adenovirus vectors for gene transfer in clinical trials include Rosenecker et ah, Infection 24:1 5-10 (1996); Sterman et ah, Hum. Gene Ther. 9:7 1013-1089 (1998). Welsh et ah, Hum. Gene Ther. 2:205-18 (1995); Alvarez et al, Hum. Gene Ther. 5:597-613 (1997); Topf et al, Gene Ther. 5:507-513 (1998); Sterman et al, Hum. Gene Ther. 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many applications, it is desirable that the g vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et ah, Proc. Natl. Acad. Sci. USA 92:9747-9751 (1995), reported that Moloney murine leukemia virus can be modified to express human heregulin fused to gp70, and the recombinant virus infects certain human breast cancer cells expressing human epidermal growth factor receptor. This can be used with other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to non-viral vectors. Such vectors can be engineered to contain specific uptake sequences which favor uptake by specific target cells.

Vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by re-implantation of the cells into a patient, usually after selection for cells which have incorporated the vector.

Vectors (e.g., retroviruses, adenoviruses, liposomes, etc.) containing the nucleic acids described herein can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another mute.

Vectors suitable for introduction of the nucleic acids described herein include non-integrating lentivirus vectors (IDLV). See, for example, Ory et al. (1996) Proc. Natl. Acad. Sci. USA 93:11382-11388; Dull et al. (1998) J. Virol. 72:8463-8471; Zuffery et al. (1998) J. Virol. 72:9873-9880; Follenzi et al. (2000) Nature Genetics 25:217-222; U.S. Patent Publication No 2009/054985.

The nucleic acids encoding the TALEN-L left monomer and TALEN-R right monomer can be expressed either on separate expression constructs or vectors, or can be linked in one open reading frame. Expression of the nuclease can be under the control of a constitutive promoter or an inducible promoter.

Administration can be by any means in which the polynucleotides are delivered to the desired target cells. For example, both in vive and ex vivo methods are contemplated. In one embodiment, the nucleic acids are introduced into a subject's cells that have been explanted from the subject, and reintroduced following F8 gene repair.

For in vive administration, intravenous injection of the nucleic acids to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree Ex vive modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et ah, (1994) Nature Genetics, 6:335-341.

If ex vivo methods are employed, cells or tissues can be removed and maintained outside the body according to standard protocols well known in the art. The compositions can be introduced into the cells via any gene transfer mechanism as described above, such as, for example, calcium phosphate mediated gene delivery, electroporation, microinjection, proteoliposomes, or viral vector delivery. The transduced cells can then be infused (e.g., in a pharmaceutically acceptable carrier) or homotopically transplanted back into the subject per standard methods for the cell or tissue type. Standard methods are known for transplantation or infusion of various cells into a subject.

7. Immune Tolerance Induction

In one embodiment, the repaired gene, upon expression, provides for the induction of immune tolerance to an administered replacement FVIII protein product. Current FVIII replacement therapies include the infusions of recombinant FVIII replacement products (r)FVIII. (r)FVIII is a biosynthetic blood coagulation prepared using recombinant DNA, and is structurally similar to endogenous wild-type human FVIII and produces the same biological effect. Due to genetic variables within a subject including the individual's specific F8 mutation type, background FVIII haplotype, and HLA haplotype, however, the (r)FVIII mismatched amino acid may induce an immune response in the subject receiving the (r)FVIII, resulting in the development of inhibitors and the reduction in efficiency of the particular (r)FVIII.

Accordingly, in one embodiment, a method of inducing tolerance to a (r)FVIII product in a subject that may receive, is receiving, or has received a (r)FVIII product is provided comprising introducing into a cell of the subject one or more isolated nucleic acids encoding a nuclease that targets a portion of the human F8 gene containing a mutation that causes hemophilia A, wherein the nuclease creates a double stranded break in the human F8 gene; and an isolated nucleic acid comprising (i) a nucleic acid encoding a truncated FVIII polypeptide or (ii) a native F8 3' splice acceptor site operably linked to a nucleic acid encoding a truncated FVIII polypeptide, wherein the nucleic acid comprising the (i) a nucleic acid encoding a truncated FVIII polypeptide or (ii) native F8 3' splice acceptor site operably linked to a nucleic acid encoding a truncated FVIII polypeptide is flanked by nucleic acid sequences homologous to the nucleic acid sequences upstream and downstream of the double stranded break in the DNA, and wherein the repaired gene, upon expression, provides for the induction of immune tolerance to an administered replacement FVIII protein product. The person administered the cells in which the F8 gene has been repaired may or may not have anti-FVIll antibodies as measured by ELISA or Bethesda assays. In one embodiment, the truncated FVIII polypeptide amino acid sequence shares homology with a positionally coordinated portion of the (r)FVIII amino acid sequence. In one embodiment, the truncated FVIII polypeptide amino acid sequence shares complete homology with a positionally correlated portion of the (r)FVIII amino acid sequence. In a further embodiment, the method further includes targeting and replacing a nucleic acid sequence within the subject's F8 gene encoding a non-mutational amino acid with the positional equivalent amino acid in the (r)FVIII. In one embodiment, the non-mutational amino acid is a non-synonymous Single Nucleotide Polymorphism (ns-SNP).

It is believed that intra-cellular expression of even a small amount of a repaired FVIII protein that closely resembles the (r)FVIII product, and concomitant surface presentation of FVIII epitopes within the cell's MHC, may enable the induce of immune tolerance to the (r)FVIII products.

The human F8 gene is polymorphic and encodes several structurally distinct FVIII proteins referred to as haplotypes. Sequencing studies of the F8 gene have revealed four common nonsynonymous-single-nucleotide polymorphisms (nsSNPs) that, together with two infrequent ns-SNPs, encode eight distinct wild-type FVIII proteins referred to as haplotype H1, H2, H3, H4, H5, H6, H7, and H8. The amino acid sequence of the H1 wild-type variant is listed as Seq. ID. No. 16.

All currently available (r)FVIII are based on either the H1 or H2 haplotype variant. Commercially available (r)FVIII include the H1 variants Kogenate® (Bayer) and Helixate® (ZLB Behring), the H2 variants Recombinate® (Baxter) and Advate® (Baxter), and the H1/H2 variant B-domain deleted Refacto® (Pfizer) and Xyntha® (Pfizer). The present invention, however, is not limited to replacing a subject's F8 gene with a coding sequence that matches or is nearly homologous to a portion of the commercially available (r)FVIII products described above, but is applicable to any (r)FVIII, including human/porcine hybrid (r)FVIII, porcine (r)FVIII, and alternative haplotype recombinant FVIII replacement products such as those identified in WO 2006/063031, which is incorporated by reference herein. Differences between a subject's FVIII and a (r)FVIII can result from, for example, missense mutations in the subject's F8 gene, nonsynonymous single-nucleotide polymorphisms (nsSNPs) (both well-known and "private" or individualized) or haplotypic variations between the subject's FVIII and (r)FVIII, inversions, for example intron 1 or 22 inversions, synthetic peptide inclusion due to B-domain deletions in the BDD-®FVIII, and the like.

Because the amino acid sequence of available (r)FVIII are known, and differences in subject's FVIII can be determined, differences (or mismatches) between the subject's endogenous FVIII protein sequence and (r)FVIII can be readily identifiable using common techniques known in the art, and the identified differences can be utilized to construct nucleic acids as described above for replacement. For example, molecular genetic studies have shown that development of inhibitors to factor VIII replacement products occurs most frequently in patients with severe hemophilia due to major gene lesions including inversions. Subjects with intron 22 inversion express the entire FVIII intracellularly, albeit on two separate polypeptides. Importantly, another gene, FRB, is also generally expressed in both normal and HA subjects. The expression product of the F8B gene, FVIIIB, has sequence identity with a portion of the C1 domain and the entire C2 domain of FVIII. The presence of this FVIIIB polypeptide is important from a tolerance standpoint as it serves as a source for any T cells epitope or B cell epitopes needed to support processes that occur in the thymus (T cell clonal deletion) and spleen (B cell anergy) to achieve central tolerance. The expression product of F8I22I starts at residue 1 and ends at residue 2124. The polypeptide expressed by the F8B begins at residue 2125 and ends at residue 2332. Accordingly subjects having the F8I22I have the requisite FVIII material to yield one or more FVIII peptides ending at or before residue 2124, the last amino acid encoded by exon 22, or beginning at or after residue 2125, the first amino acid encoded by exon 23. Any T cell epitope within such a peptide can be recognized as a self-antigen and not be immunogenic in the subject. Peptides spanning the junction between residues 2124 and 2125, if proteolyzed from a (r)FVIII and presented by MHC class II molecules, however, are "foreign" and potentially immunogenic T cell epitopes in an F8I22I subject. Because of this, all subjects having F8I22I have similar reference.

Likewise, in subjects receiving B-domain deleted-(r) FVIII product, differing amino acid sequence exist between the subject's FVIII and the replacement product caused by the removal of the B-domain in the BDD-rFVIII product. For example, in certain BDD-rFVIII, a deletion of 894 internal codons and splicing codons 762 and 1657 creates a FVIII product containing 1438 amino acids. The BDD-rFVIII contains a synthetic junctional 14-peptide sequence SFS-QNPPVLKRHQR formed by covalent attachment of the three N-terminal most residues of the B-domain. $S^{741}F^{742}S^{743}$, to the 11 C-terminal-most residues $Q^{1638}N^{1639}P^{1640}P^{1641}V^{1642}L^{1643}K^{1644}R^{1645}H^{1646}Q^{1647}R^{1648}$. This synthetic linker creates 11 unique peptides across a 15 amino acid sequence within the BDD-rFVIII, which have potential immunogenicity. In one embodiment, a donor sequence including these amino acids is utilized to replace the subject's F8 gene. Thus, in one embodiment, a donor sequence comprising a nucleic acid encoding the amino acid sequence SFSQNPPVLKRHQR is provided. In alternative embodiments, the BDD-rFVIII contains variable amounts of linker sequences. In one embodiment, the linker sequence comprises the first 10 amino acids from the N-terminus of the B-domain and 11 amino acids from the C-terminus of the B-domain.

In one embodiment, a F8 mutation in a cell from a subject having HA, for example a BOEC, iPSC, or LSEC, is identified and repaired using the nuclease approach described above and a donor sequence that is identical to a portion of a (r)FVIII product. In one embodiment, the repair takes place ex vivo, as a cell, for example a BOEC or LSEC, is explanted from the subject, repaired, and reintroduced into the subject as described above. Following repair, the cell is capable of producing FVIII, including intracellularly, and express and present potentially antigenic peptides on MHC complexes. The expression of the repaired FVIII leads to immune suppression specific to a specific (r)FVIII antigen or immunogenic epitopes expressed by the repaired F8 gene. Such a tolerogenic immune response can include any reduction, delay, or inhibition in an undesired immune response specific to the (r)FVIII antigen or epitope. Tolerogenic immune responses, therefore, can include the prevention of or reduction in inhibitors to a specific (r)FVIII. Tolerogenic immune responses as provided herein include immunological tolerance. The tolerogenic immune response can be the result of MHC Class II-restricted presentation and/or B cell presentation, or any other presentation leading to the minimized or reduced immunicity of the (r)FVIII.

Tolerogenic immune responses include a reduction in (r)FVIII antigen-specific antibody (inhibitor) production. The expression of the repaired FVIII can result in a reduction of measurable Bethesda titer units to a (r)FVIII in a subject that already has inhibitors to a (r)FVIII.

Tolerogenic immune responses also include any response that leads to the stimulation, production, or recruitment of CD4+ Treg cells and/or CD8+ Treg cells. CD4+ Treg cells can express the transcription factor FoxP3 and inhibit inflammatory responses and auto-immune inflammatory diseases (Human regulatory T cells in autoimmune diseases. Cvetanovich G L, Hafler D A. Curr Opin Immunol. 2010 December; 22(6):753-60. Regulatory T cells and autoimmunity. Vita J, Isaacs J D, Anderson A E. Curr Opin Hematol. 2009 July; 16(4):274-9). Such cells also suppress T-cell help to B-cells and induce tolerance to both self and foreign antigens (Therapeutic approaches to allergy and autoimmunity based on FoxP3+ regulatory T-cell activation and expansion. Miyara M, Wing K, Sakaguchi S. J Allergy Clin Immunol. 2009 April; 123(4):749-55). C D4+ Treg cells recognize antigen when presented by Class II proteins on APCs. CD8+ Treg cells, which recognize antigens presented by Class I (and Qa-1), can also suppress T-cell help to B-cells and result in activation of antigen-specific suppression inducing tolerance to both self and foreign antigens. Disruption of the interaction of Qa-1 with CD8+ Treg cells has been shown to dysregulate immune responses and results in the development of auto-antibody formation and an auto-immune lethal systemic-lupus-erythematosus (Kim et al., Nature. 2010 Sep. 16, 467 (7313): 328-32). CD8+ Treg cells have also been shown to inhibit models of autoimmune inflammatory diseases including rheumatoid arthritis and colitis (CD4+CD25+regulatory T cells in autoimmune arthritis. Oh S, Rankin A L, Caton A J. Immunol. Rev. 2010 January; 233(1):97-111. Regulatory T cells in inflammatory bowel disease. Boden E K, Snapper S B. Curr Opin Gastroenterol. 2008 November, 24(6):733-41). In some embodiments, the expression of the repaired FVIII provided can effectively result in both types of responses (CD4+ Treg and CD8+ Treg). In Other Embodiments, FoxP3 can be Induced in other immune cells, such as macrophages, iNKT cells, etc., and the compositions provided herein can result in one or more of these responses as well.

Tolerogenic immune responses also include, but are not limited to, the induction of regulatory cytokines, such as Treg cytokines; induction of inhibitory cytokines; the inhibition of inflammatory cytokines (e.g., IL-4, IL-1b, IL-5. TNF-α, IL-6, GM-CSF, IFN-γ, IL-2, IL-9, IL-12, IL-17, IL-18, IL-21, IL-22, IL-23, M-CSF, C reactive protein, acute phase protein, chemokines (e.g., MCP-1, RANTES, MIP-1α, MIP-1β, MIG, ITAC or IP-10), the production of anti-inflammatory cytokines (e.g., IL-4, IL-13, IL-10, etc.), chemokines (e.g., CCL-2, CXCL8), proteases (e.g., MMP-3, MMP-9), leukotrienes (e.g., CysLT-1, CysLT-2), prostaglandins (e.g., PGE2) or histamines; the inhibition of polarization to a Th17, Th1, or Th2 immune response; the inhibition of effector cell-specific cytokines: Th17 (e.g., IL-17, IL-25), Th1 (IFN-γ), Th2 (e.g., IL-4, IL-13); the inhibition of Th1-, Th2- or TH17-specific transcription factors; the inhibition of proliferation of effector T cells; the induction of apoptosis of effector T cells; the induction of tolerogenic dendritic cell-specific genes, the induction of FoxP3 expression, the inhibition of IgE induction or IgE-mediated immune responses; the inhibition of antibody responses (e.g., antigen-specific antibody production); the inhibition of T helper cell response; the production of TGF-β and/or IL-10; the inhibition of effector function of autoantibodies (e.g., inhibition in the depletion of cells, cell or tissue damage or complement activation); etc.

Any of the foregoing can be measured in vivo or may be measured in vitro. One of ordinary skill in the art is familiar with such in vivo or in vitro measurements. Tolerogenic immune responses can be monitored using, for example, methods of assessing immune cell number and/or function, tetramer analysis, ELISPOT, flow cytometry-based analysis of cytokine expression, cytokine secretion, cytokine expression profiling, gene expression profiling, protein expression profiling, analysis of cell surface markers, PCR-based detection of immune cell receptor gene usage (see T. Clay et al., "Assays for Monitoring Cellular immune Response to Active Immunotherapy of Cancer" Clinical Cancer Research 7:1127-1135 (2001)), etc. Tolerogenic immune responses may also be monitored using, for example, methods of assessing protein levels in plasma or serum, immune cell proliferation and/or functional assays, etc. In some embodiments, tolerogenic immune responses can be monitored by assessing the induction of FoxP3.

In some embodiments, the reduction of an undesired immune response or generation of a tolerogenic immune response may be assessed by determining clinical endpoints, clinical efficacy, clinical symptoms, disease biomarkers and/or clinical scores. Tolerogenic immune responses can also be assessed with diagnostic tests to assess the presence or absence of inhibitors.

In one embodiment, expression of the repaired FVIII results in the prevention, reduction, or elimination of inhibitors to a (r)FVIII. The presence of inhibitors can be assessed by determining one or more antibody titers to the (r)FVIII using techniques known in the art and include Enzyme-linked Immunosorbent Assay (ELISA), inhibition liquid phase absorption assays (ILPAAs), rocket immunoelectrophoresis (RIE) assays, and line immunoelectrophoresis (LIE) assays.

In one embodiment, cells can be harvested, repaired, and then stored for future tolerance induction administration. The cells can be administered in effective amounts, such as the effective amounts described elsewhere herein. Doses of dosage forms contain varying amounts of cells expressing a repaired FVIII, according to the invention. The amount of expressing cells present in the dosage forms can be varied according to the nature and amount of the expressed FVIII, the therapeutic benefit to be accomplished, and other such parameters. In embodiments, dose ranging studies can be conducted to establish optimal therapeutic amount of repaired FVIII peptides to be expressed by the cells. In embodiments, the cells express a repaired FVIII in a dosage form in an amount effective to generate a tolerogenic immune response to a (r)FVIII epitope upon administration to a subject. It may be possible to determine amounts of cellular expression effective to generate a tolerogenic immune response using conventional dose ranging studies and techniques in subjects. Dosage forms may be administered at a variety of frequencies. In one embodiment, at least one administration of expressing cells is sufficient to generate a pharmacologically relevant response. In one embodiment, at least two administrations, at least three administrations, or at least four administrations or more, of the expressing cells are utilized to ensure a pharmacologically relevant response.

Prophylactic administration of the expressing cells can be initiated prior to the onset of inhibitor development, or therapeutic administration can be initiated after inhibitor development is established. In some embodiments, administration of cells expressing repaired FVIII is undertaken e.g., prior to administration of the (r)FVIII. In exemplary embodiments, the expressing cells are administered at one or more times including, but not limited to, 30, 25, 20, 15, 14, 13, 12, 11, 10, 9, 8, 7, 6, 5, 4, 3, 2, 1, or 0 days prior to administration of the (r)FVIII. In addition or alternatively, the cells can be administered to a subject following administration of the (r)FVIII. In exemplary embodiments, cells are administered at one or more times including, but not limited to, 1, 2, 3, 4, 5, 6, 7, 8, 9, 10, 11, 12, 13, 14, 15, 20, 25, 30, etc. days following administration of (r)FVIII.

In some embodiments, a maintenance dose is administered to a subject after an initial administration has resulted in a tolerogenic response in the subject, for example to maintain the tolerogenic effect achieved after the initial dose, to prevent an undesired immune reaction in the subject, or to prevent the subject becoming a subject at risk of experiencing an undesired immune response or an undesired level of an immune response. In some embodiments, the maintenance dose is the same dose as the initial dose the subject received. In some embodiments, the maintenance dose is a lower dose than the initial dose. For example, in some embodiments, the maintenance dose is about ¾, about ⅔, about ½, about ⅓, about ¼, about ⅛, about 1/10, about 1/20, about 1/25, about 1/50, about 1/100, about 1/1,000, about 1/10,000, about 1/100,000, or about 1/1,000,000 (weight/weight) of the initial dose.

In some aspects, methods and compositions provided herein are useful in conjunction with established means of ITI for (r)FVIII. ITI protocols for hemophilia patients, including patients with high titer inhibitors against (r)FVIII, are known in the art and are generally described, e.g., in Mariani et al., Thromb Haemost., 72: 155-158 (1994) and DiMichele et al., Thromb Haemost. Suppl 130 (1999). Administration of the repaired cells described herein can be conducted before, after, and/or concurrently with established ITI protocols and/or variations thereof. For example, in some aspects, methods provide herein increase the effectiveness of established ITI protocols (e.g., the degree and/or likelihood of successful treatment) and/or reduce associated costs or side effects. In further aspects, methods provide herein allow established ITI protocols to be beneficially modified, e.g., to decrease the frequency, duration, and/or dose of FVIII administration.

In a particular embodiment, the ITI strategy described herein is combined with an antigenic peptide immunization strategy. In a particular embodiment, the strategy described herein is combined with the administration of overlapping sets of tolerogenic peptides based on amino acid differences between the (r)FVIII protein and the subject's endogenous FVIII protein. In a particular embodiment, the strategy described herein is combined with the administration of overlapping sets of tolerogenic peptides based on amino acid differences between the (r)FVIII protein and the subject's repaired FVIII protein, described in U.S. Application 61/802,547, incorporated by reference herein. These amino acid residue differences between the subject's FVIII and (r)FVIII can be positioned or mapped within specific loci in the (r)FVIII, wherein the differing (r)FVIII amino acidsindividually termed the reference locus—serves as a reference point or points for the preparation of a set or sets of tolerizing peptides—termed tolerizing amino acids ("TAAs")—that may incorporate T-cell epitopes capable of inducing immune tolerance of, or the prevention, reduction, or elimination of inhibitor development to, the (r)FVIII. Each TAA within a set includes a (r)FVIII amino acid residing at a reference locus, and a TAA set includes between about 9 to 21 separate peptides of between 9 to 21 amino acids in length, wherein the number of peptides in a TAA set is directly correlated with the amino acid length of the TAA (i.e., a TAA set containing TAAs 9 amino acids in length contains 9 peptides; a TAA set containing TAAs 10 amino acids in length contains 10 peptides, etc.).

A method of deriving TAA peptides is generally as follows. The first peptide of each TAA has as its first amino acid position the first amino acid residue of a reference locus of the (r)FVIII, while the remaining amino acid residues are identical to the downstream amino acids in the (r)FVIII across the length of the TAA peptide. If only a single amino acid residue difference exists at the locus (for example in the case of a missense mutation or nsSNP), then the reference locus consists of a single amino acid residue. If the differences encompass more than one contiguous amino acid residue (for example in the case of some deletions), then the first differing amino acid residue in the (r)FVIII serves as the reference locus. For example, if the TAA is 9 amino acids in length, the first amino acid in the first peptide is the first amino acid of the reference locus, and the remaining 8 amino acid residues are the 8 loci residues of the (r)FVIII immediately downstream from the reference locus (as determined from amino acid position 1 to 2332 in the wt FVIII protein). The second peptide of each TAA has as its second amino acid position the reference locus, with the first amino acid position being the first amino acid residue in the (r)FVIII immediately upstream from the reference locus, and the remaining 7 amino acid residues being the 7 loci residues of the (r)FVIII immediately downstream from the reference locus. As such, for each successive TAA peptide in the TAA set, the reference locus is shifted one amino acid position downstream, and the first amino acid reflects a shift from the preceding peptide of one amino acid upstream in the (r)FVIII. Accordingly, the last TAA peptide of the set—in the preceding example, the ninth peptide—has the reference locus in the last amino acid residue position, and be preceded by upstream amino acid residues—in the preceding example, the 8 residues of the (r)FVIII immediately upstream of the reference locus. The same method described above can be generally used to create TAA sets of varying peptide sizes, wherein the reference locus in each successive peptide in the set is shifted one position downstream and the first amino acid position in each successive peptide is shifted one residue upstream from the first amino acid position in the preceding peptide, until the reference locus occupies the last amino acid position in the last peptide of the set.

Following the method of generating sets of TAA as described above, a set of TAA peptides corresponds with a contiguous portion of the (r)FVIII across 2X−1 amino acids, where X is the length of the peptides contained in the set. For example, as described in the preceding example, a TAA set containing 9 peptides, each being 9 amino acids in length, will as a set overlap with 17 contiguous amino acids of the (r)FVIII. Furthermore, the contiguous (r)FVIII amino acid sequence overlapped by the TAA peptides includes X−1 amino acid residues upstream and X−1 amino acid residues downstream from the first amino acid of the reference locus within the (r)FVIII, wherein X is the length of the peptides contained in the set. For example, a set of 9 peptides of 9 amino acids in length overlaps with 8 amino acids upstream and 8 amino acids downstream from the first amino acid of the reference locus within the (r)FVIII. This general process will be applicable to the generation of TAA sets for most identified amino acid differences, with a few exceptions, for example in the derivation of TAA sets to a few BDD-rFVIIIrp synthetic linker as described further herein.

In an alternative embodiment, the present strategy is combined with methods of antigen specific muting of the B cell response to specific potential antigens within the (r)FVIII. Accordingly, the repaired cells are combined with a strategy using liposomal nanoparticles displaying peptides comprising peptides derived from the (r)FVIII and based on amino-acid mismatches between the subject's endogenous FVIII protein, or alternatively the repair FVIII protein, and the (r)FVIII (as described above), and glycan ligands of the inhibitory co-receptor CD22. Methods of producing antigenic liposomes displaying CD22 ligands are described in, for example, Macauley et al., "Antigenic liposomes displaying CD22 ligands induce antigen-specific B cell apoptosis," J. Clin. Invest. 2013 Jul. 1, 123(7): 3074-3083.

In some embodiments, the cells are associated with, combined with, or administered with immunosuppressive compounds capable of inducing adaptive regulatory T cells. In one embodiment, the immunosuppressive compounds may include, but is not limited to, IL-10, TGF-β, and/or rapamycin and/or other limus compounds, including but not limited to biolimus A9, everolimus, tacrolimus, and zotarolimus, and/or combinations thereof.

In one embodiment a "dose escalation" protocol can be followed, where a plurality of doses is given to the patient in ascending concentrations. Such an approach has been used, for example, for phospholipase A2 peptides in immunotherapeutic applications against bee venom allergy (Müller et al. (1998) J. Allergy Clin Immunol. 101:747-754 and Akdis et al. (1998) J. Clin. Invest. 102:98-106).

In one aspect, the amount of cells to be administered can be determined using a stoichiometric calculation based on current ITI administration protocols. For example, the amount of cells to be administered can be based on the equivalent quantity of the peptide that would be administered in a standard ITI protocol which uses the full length (r)FVIII. To determine dosing period, the subject's dendritic cells' reactivity to the expressed repaired FVIII can be determined prior to the start of cell administration, and then periodically monitored until tolerance to the (r)FVIII is observed.

EXAMPLES

Example 1: Ex Vivo Gene Repair

Examples are provided of an ex vivo gene repair strategies that can be performed without the use of viral vectors. Genetic materials are delivered to restore secretion of a wild-type full-length FVIII protein to lymphoblastoid cells derived from a human HA patient with the intron-22 (I22)-inverted FVIII gene, designated F8I22I, using electroporation and TALE-nucleases (TALENs). A similar strategy can be used as an example to repair the naturally-occurring I22I-mutation in cells from an animal model of HA (dogs of the HA canine colony located at the University of North Carolina in Chapel Hill). Canine (adipose) tissue, which can be induced to acquire many properties of hepatocytes, can be used.

Use of autologous cells is an attractive therapy for several reasons as levels of blood clotting proteins needed to maintain hemostasis may be more readily produced by expansion of large populations of cells ex vive and reintroduction into the patient. Repair of the F8I22I gene residing in a B-lymphoblastoid cell-line derived from a patient with severe HA caused by the I22I-mutation is effected by using electroporation to deliver (i) two distinct mRNAs encoding a highly specific heterodimeric TALEN that targets a single human genome site located in F8 near the 5'-end of I22 and (ii) the corresponding donor plasmid that carries the "editing cassette", which is comprised of a functional 3'-intron splice site ligated immediately 5' of a partial F8 cDNA matched in sequence with the wild-type sequence of exons 23-26 in the patient's own I22-inverted F8 locus, flanked by "left" and "right" homology arms.

The use of viral-free methods to derive autologous cells of various phenotypes and to stably introduce genetic information into the genome is attractive. These methods can be effectively used to successfully "repair" the intron-22 (I22)-inverted human F8 locus (F8I22I), which arises through a highly-recurrent mutational event essentially restricted to the male germ-line. This same F8 abnormality, which is widely known as the I22-inversion (I22I)-mutation, occurs naturally in dogs, and results in spontaneous bleeding. Two large colonies of HA dogs have been established, one at the University of North Carolina in Chapel Hill. Investigation of F8I22I at the molecular genetic, biochemical, and cellular levels to characterize its expression products have been studied in order to determine the immune response to replacement FVIII. Extensive sequencing efforts and analyses of the F8I22I and its mRNA transcripts allow for an innovative gene repair strategy that exploits nuclease technology, for example, transcription activator-like effector (TALE)-nuclease (TALEN) technology to repair the I22I-mutation.

Lymphoblastoid cells derived from HA patient with the I22I-mutation is obtained. The left (TALEN-L) and right (TALEN-R) monomers comprising the heterodimeric TALEN is shown in FIG. 3, which was specifically designed to cleave within the human F8 I22-sequence, ~1 kb downstream of the 3'-end of exon-22. In alternative embodiments, the TALENs target sequences throughout the FVIII gene, with replacement of the corresponding FV8 gene sequence on the donor sequence.

An example of a sequence that can be targeted includes a sequence within intron 22 (tactatgggatgagttgc-agatggcaagtaagacactggggagattaaat (SEQ. ID No. 1)), where the underlined regions of sequence are recognized by the left TAL Effector DNA-binding domain and the right TAL Effector DNA-binding domain). Another example of a sequence that can be targeted includes a sequence at the junction of exon 22 with intron 22 (tggaaccttaatggtatgtaattagtcatttaaagggaatgcctgaata (SEQ. ID No. 2)), where the underlined regions of sequence are recognized by the left TAL Effector DNA-binding domain and the right TAL Effector DNA-binding domain). Another example of a sequence that can be targeted within intron 22 is depicted in FIG. 3 (ttagtattatagtttctcagattatca ccagtgatactatgga (SEQ. ID No. 3)), where the underlined regions of sequence are recognized by the left TAL Effector DNA-binding domain and the right TAL Effector DNA-binding domain). The two TALEN expression plasmids that target these sequences (or the mRNA) are co-transfected with the donor plasmid. The donor plasmid contains flanking homology regions to the intron 22 locus, which allows for recombination of the donor plasmid into the chromosome. The cDNA of exons 23 to 26 of the F8 gene is contained between the flanking homology regions of the donor plasmid. The donor plasmid can also contain a suicide gene (such as the thymidine kinase gene from the herpes simplex virus), which allows counter-selection to avoid random and multi-copy integration into the genome.

Electroporation (AMAXA Nucleofection system) and chemical transfection (with a commercial reagent optimized to this cell type) can be used as transfection methods for the lymphoblastoid cells. A plasmid containing the green fluorescent protein (GFP) gene is introduced into the cells using both methods. The cells are analyzed by fluorescent microscopy to obtain an estimate of transfection efficiency, and the cells are observed by ordinary light microscopy to determine the health of the transfected cells. Any transfection method that gives a desirable balance of high transfection efficiency and preservation of cell health in the lymphoblastoid cells can be used. The TALEN mRNAs and the gene repair donor plasmid is then introduced into the lymphoblastoid cells using a transfection method. The TALENs for the human lymphoblastoid cells and their target site are shown in FIG. 3.

Repair of the F8I22I in the adipose tissue-derived hepatocyte-like cells from the I22I HA canine animal model is effected using electroporation to deliver mRNAs encoding an analogous TALEN that targets the 5'-end of I22 in canine F8 and an analogous donor plasmid carrying a "splice-able" cDNA spanning canine F8 exons 23-26.

Adipose tissue is collected from these FVIII deficient dogs by standard liposuction. Stromal cells from the adipose tissue are reprogrammed into induced pluripotent stem cells (iPSC), as described by Sun et al. ("Feeder-free derivation of induced pluripotent stem cells from adult human adipose stem cells" Proc Natl Acad Sci USA. 106: 720-5, 2009) with two modifications: (i) mRNA of the reprogramming factors are used in place of lentiviral vectors and (ii) the reprogramming is performed under conditions of hypoxia, 5% O2, and in the presence of small molecules that have been found to increase the reprogramming efficiency. Once produced and characterized, pluripotent canine cells are obtained.

The defective FVIII sequence in iPSC is replaced by the correct sequence using site-specific TALE nucleases (see FIG. 4). The iPSC with repaired Factor VIII are differentiated into hepatocytes using well established protocols (see, for example, Hay et al. "Direct differentiation of human embryonic stem cells to hepatocyte-like cells exhibiting functional activities" Cloning Stem Cells. 9: 51-62, 2007; Si-Tayeb et al. "Highly efficient generation of human hepatocyte-like cells from induced pluripotent stem cells" Hepatology. 51: 297-305, 2010; and Cayo et al. "JD induced pluripotent stem cell-derived hepatocytes faithfully recapitulate the pathophysiology of familial hypercholesterolemia" Hepatology. May 31, 2012). In short, small colonies of iPSC are induced to differentiate for the first 3 days into definitive endoderm by treatment with 50 ng/mL Wnt3a and 100 ng/mL Activin A, and then into the hepatocyte lineage by 20 ng/mL BMP4. Two expression plasmids necessary to produce mRNAs encoding a functional TALEN are obtained. These are designed to cleave and yield a double-stranded DNA break at only a single site within the canine genome, located within canine F8 I22, ~0.3 kb downstream of the 3'-end of exon-22. The left (TALEN-L) and right (TALEN-R) monomers comprising this heterodimeric TALEN is shown above in FIG. 4.

A donor plasmid containing the sequence of the 3'-end of canine F8 intron-22 and all of canine F8 exon-22 as the left homologous sequence and the 5'-end of canine F8 intron-23 as the right homologous sequence to provide an adequate length of genomic DNA for efficient homologous recombination at the target site (i.e., the TALEN cut site) is created. The TALEN mRNAs and the gene repair donor plasmid are introduced into the pluripotent canine cells using a transfection method described herein.

Likewise, in humans, human iPSCs are electroporated with the human F8 TALENs & donor plasmid described above, to assess candidate genome-editing tools (which were designed to be equally capable of "editing" the I22-sequence in the wild-type and I22-inverted F8 loci, F8 and F8I22I, respectively) for their efficiency of site-specific gene repair. The genomic DNA at the repaired F8 loci, as well as the mRNAs and expression products synthesized by, the cells described above are assessed before and after electroporation.

Figure 8:
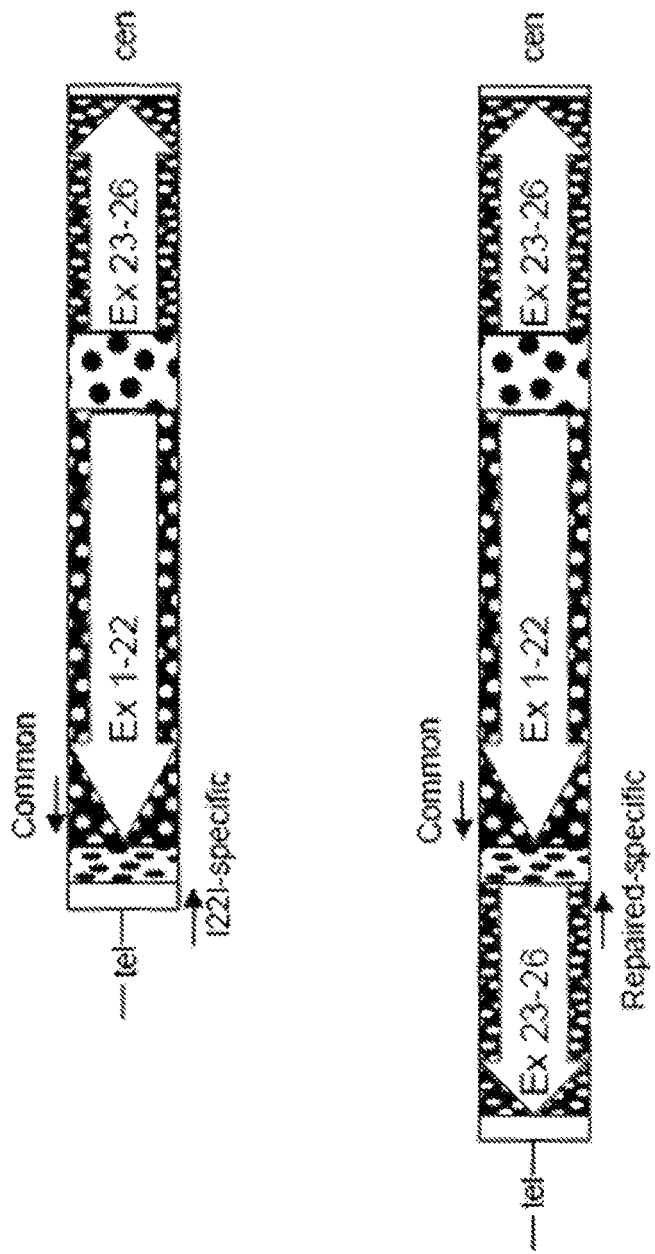
FIG. 8 shows PCR primer design to confirm correct integration of exons 23-26 to repair the human intron-22 (I22)-inverted F8 locus, $F8_{I22I}$.

The TALEN gene repair method described above inserts F8 exons 23-26 immediately downstream (telomeric) to F8 exons 1-22 to encode a FVIII protein. Genomic DNA, spliced mRNA, and protein sequences differ among normal, repaired, and unrepaired cells (see FIG. 5). Gene repair is verified in genomic DNA through the use of PCR. Specific PCR primers are designed to amplify across the homologous recombination target sequence in unrepaired and repaired cells. A common primer is placed toward the end of exon-22. An I22I-specific primer is placed in the sequence telomeric to exon-22 in the I22I-inverted cells. A Repaired-specific primer is placed in the inserted exon 23-26 sequence. Primer design is shown in FIG. 8. Separate sets of primers are designed for human and canine sequences.

Characterization of the genomic DNA at the repaired F8 loci, as well as the mRNAs and expression products synthesized by, the cells described above, before and after electroporation are performed.

A quantitative RT-PCR test that specifically detects and quantifies the mRNA transcripts from normal and I22I cells is used. The quantitative RT-PCR test uses three separate primer sets: one set to detect exons 1-22, one set to detect exons 23-26, and one set that spans the exon-22/exon-23 junction. mRNA is purified from cells before and after transfection. The existing primer design to probe mRNA from the human cells is used. Primers against canine sequences are designed using the same strategy and then the mRNA from the canine cells is probed using these new primers. An increased signal from the exon-22/exon-23 junction reaction in repaired cells, relative to unrepaired cells should be observed.

Monoclonal antibody ESH8, which is specific for the C2-domain of the FVIII protein, is be used. NIH3T3 cells were transfected with expression constructs encoding full-length and I22I F8 genes and then assayed by flow cytometry. Signal from the ESH8 antibody was high in cells transfected with the full-length construct but virtually absent in cells transfected with the I22I construct. The ESH8 antibody is used to test transfected cells. There should be an increased signal in repaired cells relative to unrepaired cells. Secreted FVIII levels, as measured by ELISA, are dramatically lower in I22I cells relative to normal cells. Whole-cell lysates and supernates from transfected cells are obtained and tested for FVIII concentration by ELISA. There should be an increase in FVIII concentration in the supernates from repaired cells relative to unrepaired cells.

In another example, canine blood outgrowth endothelial cells (cBOECs) and canine iPSCs derived from canine adipose tissue can be transfected with TALENs that target the F8I22I canine gene and a plasmid repair vehicle that carries exons 23-26 of cF8. TALENs are expected to make DSBs in the F8I22I DNA at the target site to allow "homologous recombination and repair" of the canine F8 I22I gene by insertion of exons 23-26 of the canine F8. The TALENS are designed to cleave and yield a DSB at only a single site within the canine genome, located within canine F8 I22, (~0.3 kb) downstream of the 3'-end of exon-22. The donor plasmid contains the sequence of canine F8 exons 23-26 flanked by the 3'-end of canine F8 intron-22 and all of canine F8 exon-22 as the left homologous sequence and the 5'-end of canine F8 intron-23 as the right homologous sequence to provide an adequate length of genomic DNA for efficient homologous recombination at the target site.

Feasibility of deriving canine iPSCs is well established. An mRNA transcript that enables expression of the so called "Yamanaka" genes coding for transcription factors OCT4, SOX2, KLF4 and C-MYC to induce iPSCs from canine adipose derived stem cells (hADSCs). iPSCs have been transfected using Nucleofector. For transfection, Qiagen's Polyfect transfection reagents can be used with TALENs for many cell types, including BOECs. Transfection methods can be assessed using commercial reagents and transfected cells can be analyzed by fluorescent microscopy to obtain an estimate of transfection efficiency, while viability can be determined by Trypan Blue dye exclusion. The transfection method that gives the best balance of high transfection efficiency and preservation of cell health can be used.

Prior to commencing transfection with the TALENS and repair plasmid, the cleavage activity of the TALENs against the target site can be analyzed. This can be done by monitoring TALEN induced mutagenesis (Non-Homologous End Joining Repair) via a T7 Endonuclease assay. To assess potential risk of unintended genomic modification induced by the selected repair method, off-site activity is analyzed following transfection. In silico identification based on homologous regions within the genome can be used to identify the top 20 alternative target sites containing up to two mismatches per target half-site. PCR primers can be synthesized for the top 20 alternative sites and Surveyor Nuclease (Cel-I) assays (Tranagenomics, Inc.) can be performed for each potential off-target site.

Transfection for expression and secretion of FVIII can be assessed in the various cell types before and after transfection. Genomic DNA is isolated from cells before and after transfection. Purified genomic DNA is used as template for PCR. Primers are designed for amplification from a FVIII I22I-specific primer only in unrepaired cells, and amplification from the repaired-specific primer only in repaired cells. RT-PCR can specifically detect and quantify the mRNA hF8 transcripts from normal and I22I cells. The quantitative RT-PCR test uses three separate primer sets: one set to detect exons 1-22, one set to detect exons 23-26, and one set that spans the exon-22/exon-23 junction. mRNA is purified from cells before and after transfection, with an increased signal from the exon-22/exon-23 junction reaction in repaired cells, relative to unrepaired cells. Flow-cytometry based assays may also be used for FVIII protein in peripheral blood mononuclear cells (PBMCs).

iPSCs derived from canine adipose tissue engineered can be conditioned to secrete FVIII to hepatocyte-like tissue. Canine iPSCs are conditioned toward hepatocyte like cells using a three step protocol as described by Chen et al. that incorporates hepatocyte growth factor (HGF) in the endodermal induction step (Chen Y F, Tseng C Y, Wang H W, Kuo H C, Yang V W, Lee O K. Rapid generation of mature hepatocyte-like cells from human induced pluripotent stem cells by an efficient three-step protocol. Hepatology. 2012 April; 55(4): 1193-203).

Subpopulations of cBOECs are segregated and expanded and then characterized for the expression of endothelial markers, such as Matrix Metalloproteinases (MMPs), and cell-adhesion molecules (JAM-B, JAM-C, Claudin 3, and Claudin 5) using RT-PCR. Detailed RT-PCR methods, including primers for detecting expression of mRNA transcripts of the cell-adhesion molecules of interest and detailed immunohistochemistry methods to detect the proteins of interest, including a list of high affinity antibodies have been published by Geraud et al. (Géraud C, et al. Unique cell type-specific junctional complexes in vascular endothelium of human and rat liver sinusoids. PLoS One. 2012; 7(4):e34206). Antibodies that detect JAM-B, JAM-C, Claudin 3, and Claudin 5 may be purchased from LifeSpan Biosciences (www.lsbio.com).

One subpopulation of co-cultured cBOECs can be prepared and segregated early (before ~4 passages of outgrowth). Later segregation of the subpopulation can occur after ~10 passages. After 1 week of co-culture, two cBOECs subpopulations can be compared for expression and secretion of FVIII, and suitability for engraftment in the canine liver. Co-culturing of hepatocytes can be done with several cell types including human umbilical vein endothelial cells (HUVECs). cBOECs can be used as surrogates for HUVECS in this system. Once the repaired cBOECs (with the repaired FVIII gene) are obtained, the cells can be used to induce immune tolerance in canines with high titer-antibodies to FVIII.

Example 2: Protocol for Factor VIII Gene Repair in Humans

Obtaining a Blood Sample

A protocol for gene repair of the F8 gene in blood outgrowth endothelial cells (BOECs) is described in the following example. First, a blood sample is obtained, with 50-100 mL of patient blood samples obtained by venipuncture and collection into commercially-available, medical-grade collecting devices that contain anticoagulants reagents, following standard medical guidelines for phlebotomy. Anticoagulant reagents that are used include heparin, sodium citrate, and/or ethylenediaminetetraacetic acid (EDTA). Following blood collection, all steps proceed with standard clinical practices for aseptic technique.

Isolating Appropriate Cell Populations from Blood Sample

Procedures for isolating and growing blood outgrowth endothelial cells (BOECs) have been described in detail by Hebbel and colleagues (Lin, Y., Weisdorf, D. J., Solovey, A. & Hebbel, R. P. Origins of circulating endothelial cells and endothelial outgrowth from blood. *J Clin Invest* 105, 71-77 (2000)). Peripheral blood mononuclear cells (PBMCs) are purified from whole blood samples by differential centrifugation using density media-based separation reagents. Examples of such separation reagents include Histopaque-1077, Ficoll-Paque, Ficoll-Hypaque, and Percoll. From these PBMCs multiple cell populations can be isolated, including BOECs. PBMCs are resuspended in EGM-2 medium without further cell subpopulation enrichment procedures and placed into 1 well of a 6-well plate coated with type I collagen. This mixture is incubated at 37° C. in a humidified environment with 5% $CO_2$. Culture medium is changed daily. After 24 hours, unattached cells and debris are removed by washing with medium. This procedure leaves about 20 attached endothelial cells plus 100-200 other mononuclear cells. These non-endothelial mononuclear cells die within the first 2-3 weeks of culture.

Cell Culture for Growing Target Cell Population

BOECs cells are established in culture for 4 weeks with daily medium changes but with no passaging. The first passaging occurs at 4 weeks, after approximately a 100-fold expansion. In the next step, 0.025% trypsin is used for passaging cells and tissue culture plates coated with collagen-I as substrate. Following this initial 4-week establishment of the cells in culture, the BOECs are passaged again 4 days later (day 32) and 4 days after that (day 36), after which time the cells should number 1 million cells or more.

In Vitro Gene Repair

In order to affect gene repair in BOECs, cells are transfected with 0.1-10 micrograms per million cells of each plasmid encoding left and right TALENs and 0.1-10 micrograms per million cells of the repair vehicle plasmid. Transfection is done by electroporation, liposome-mediated transfection, polycation-mediated transfection, commercially available proprietary reagents for transfection, or other transfection methods using standard protocols. Following transfection, BOECs are cultured as described above for three days.

Selection of Gene-Repaired Clones

Using the method of limiting serial dilution, the BOECs are dispensed into clonal subcultures, and grown as described above. Cells are examined daily to determine which subcultures contain single clones. Upon growth of the subcultures to a density of >100 cells per subculture, the cells are trypsinized, re-suspended in medium, and a $\frac{1}{10}$ volume of the cells is used for colony PCR. The remaining $\frac{9}{10}$ of the cells are returned to culture. Using primers that detect productively repaired F8 genes, each $\frac{1}{10}$ volume of colonies are screened by PCR for productive gene repair. Colonies that exhibit productive gene repair are further cultured to increase cell numbers. Using the top 20 predicted potential off-site targets of the TALENs, each of the colonies selected for further culturing is screened for possible deleterious off-site mutations. The colonies exhibiting the least number of off-site mutations are chosen for further culturing.

Preparation of Cells for Re-Introduction into Patients by Conditioning and/or Outgrowth Prior to re-introducing the cells into patients, the BOECs are grown in culture to increase the cell numbers. In addition to continuing cell culture in the manner described above, other methods can be used to condition the cells to increase the likelihood of successful engraftment of the BOECs in the liver sinusoidal bed of the recipient patient. These other methods include: 1) co-culturing the BOECs in direct contact with hepatocytes, wherein the hepatocytes are either autologous patient-derived cells, or cells from another donor; 2) co-culturing the BOECs in conditioned medium taken from separate cultures of hepatocytes, wherein the hepatocytes that yield this conditioned medium are either autologous patient-derived cells, or cells from another donor, or 3) culturing the BOECs as spheroids in the absence of other cell types.

Co-culturing endothelial cells with hepatocytes is described further in the primary scientific literature (e.g. Kim, Y. & Rajagopalan, P. 3D hepatic cultures simultaneously maintain primary hepatocyte and liver sinusoidal endothelial cell phenotypes. *PLoS ONE* 5, e15456 (2010)). Culturing endothelial cells as spheroids is also described in the scientific literature (e.g. Korff. T. & Augustin, H. G. Tensional forces in fibrillar extracellular matrices control directional capillary sprouting. *J Cell Sci* 112 (Pt 19), 3249-3258 (1999)). Upon growing the colonies of cells to a total cell number of at least 1 billion cells, the number of cells needed for injection (>50 million cells) into the patient are separated from the remainder of the cells and used in the following step for injection into patients. The remainder of the cells are aliqouted and banked using standard cell banking procedures.

Injection of Gene-Repaired BOECs into Patients

BOECs that have been chosen for injection into patients are resuspended in sterile saline at a dose and concentration that is appropriate for the weight and age of the patient. Injection of the cell sample is performed in either the portal vein or other intravenous route of the patient, using standard clinical practices for intravenous injection.

Throughout this application, various publications are referenced. The disclosures of these publications in their entireties are hereby incorporated by reference into this application, to the extent allowed by law.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

What is claimed is:

1. An in vitro or ex vivo method of repairing a mutated F8 gene in an endothelial or hepatocyte cell of a hemophilia A subject comprising:
providing an endothelial or hepatocyte cell of the subject comprising an inversion mutation in the mutated F8 gene;
introducing into the cell an isolated nucleic acid encoding a nuclease that targets the inversion mutation in the mutated F8 gene and creates a double stranded break in the mutated F8 gene; and a donor sequence comprising (i) a nucleic acid encoding a truncated FVIII polypeptide or (ii) a native F8 3' splice acceptor site operably linked to a nucleic acid encoding a truncated FVIII polypeptide,
wherein the donor sequence is flanked by nucleic acid sequences homologous to the nucleic acid sequences upstream and downstream of the double stranded break in the F8 gene; and
obtaining a repaired endothelial or hepatocyte cell that comprises a repaired inversion mutation of the mutated F8 gene of the subject.

2. The method of claim 1, wherein the repaired endothelial or hepatocyte cell of the subject comprising the corrected F8 gene is administered directly to the subject.

3. The method of claim 1, wherein the isolated nucleic acids are administered ex vivo to endothelial or hepatocyte cells isolated from the subject.

4. The method of claim 1, wherein the nuclease is a zinc finger nuclease (ZFN), Transcription Activator-Like Effector Nuclease (TALEN), or a CRISPR (Clustered Regularly Interspaced Short Palindromic Repeats)-associated (Cas) nuclease.

5. The method of claim 1, wherein the nuclease targets intron 22 of the F8 gene.

6. The method of claim 1, wherein the nuclease targets intron 1 of the F8 gene.

7. The method of claim 1, wherein the nuclease targets the exon 22/intron 22 junction.

8. The method of claim 1, wherein the nuclease targets the exon 1/intron 1 junction.

9. The method of claim 1, wherein the subject's F8 mutation is an intron 22 inversion.

10. The method of claim 1, wherein the subject's F8 mutation is a point mutation or a deletion.

11. The method of claim 1, wherein the cells are endothelial cells.

12. The method of claim 1, wherein the cells are blood outgrowth endothelial cells (BOECs) or liver sinusoidal endothelial cells (LSECs).

13. The method of claim 12, wherein the BOECs are co-cultured with hepatocytes or LSECs, or both.

14. The method of claim 12, wherein the BOECs are co-cultured with induced pluripotent stem cells.

* * * * *